United States Patent [19]

See et al.

[11] Patent Number: 5,123,951
[45] Date of Patent: Jun. 23, 1992

[54] SYNERGISTIC PLANT GROWTH REGULATOR COMPOSITIONS

[75] Inventors: Raymond M. See, Franklinton; Charles D. Fritz, Raleigh; David T. Manning, Cary; Thomas N. Wheeler, Raleigh; Anson R. Cooke, Durham, all of N.C.

[73] Assignee: Rhone-Poulenc Nederland B.V., Amstelveen, Netherlands

[21] Appl. No.: 17,150

[22] Filed: Mar. 4, 1987

Related U.S. Application Data

[63] Continuation-in-part of Ser. No. 846,392, Mar. 31, 1986, abandoned.

[51] Int. Cl.$^5$ .................... A01N 37/22; A01N 57/12
[52] U.S. Cl. .................................. 71/86; 71/98; 71/103; 71/105; 71/115; 71/77; 71/69
[58] Field of Search .......................... 71/115, 86, 111

[56] References Cited

U.S. PATENT DOCUMENTS

| | | | |
|---|---|---|---|
| 569,425 | 10/1896 | Piutti | 562/455 |
| 2,304,820 | 12/1942 | Hanford et al. | 260/471 |
| 2,494,801 | 1/1950 | Fisher | 260/288 |
| 2,504,896 | 4/1950 | Snyder et al. | 260/471 |
| 2,523,470 | 9/1950 | Kropa et al. | 252/8.1 |
| 2,742,502 | 4/1956 | Crowe | 260/562 |
| 3,016,295 | 1/1962 | Davidson et al. | 71/2.7 |
| 3,072,473 | 1/1963 | Harris | 71/2.6 |
| 3,095,352 | 6/1963 | Uhlenbroek et al. | 167/30 |
| 3,254,108 | 5/1966 | Maggiulli et al. | 260/465 |
| 3,418,345 | 12/1968 | Baker | 260/404.5 |
| 3,452,086 | 6/1969 | Montzka | 260/519 |
| 3,544,587 | 12/1970 | Brown | 260/326.3 |
| 3,624,130 | 11/1971 | Klemm et al. | 260/471 |
| 3,658,892 | 4/1972 | Martin et al. | 260/518 A |
| 3,803,221 | 4/1974 | Ackerman | 260/518 A |
| 3,860,572 | 1/1975 | Peter et al. | 260/207 |
| 3,876,678 | 4/1975 | Pilgram et al. | 260/456 R |
| 3,879,188 | 4/1975 | Fritz et al. | 71/86 |
| 3,885,951 | 5/1975 | Hofer et al. | 71/103 |
| 3,927,062 | 12/1975 | Pilgram et al. | 260/456 NS |
| 3,939,204 | 2/1976 | Buttermann | 260/518 A |
| 4,014,679 | 3/1977 | Perronet et al. | 71/118 |
| 4,021,224 | 5/1977 | Pallos et al. | 71/88 |
| 4,031,064 | 6/1977 | Schnee et al. | 260/67.6 R |
| 4,042,620 | 8/1977 | Laforest et al. | 260/518 R |
| 4,154,952 | 5/1979 | Schultz | 560/96 |
| 4,230,484 | 10/1980 | Batch et al. | 71/111 |
| 4,240,819 | 12/1980 | Fritz et al. | 71/76 |
| 4,276,078 | 6/1981 | Pallos et al. | 71/88 |
| 4,332,612 | 6/1982 | Brown | 71/95 |
| 4,352,689 | 10/1982 | Fritz et al. | 71/86 |
| 4,359,334 | 11/1982 | Brown | 71/95 |
| 4,367,344 | 1/1983 | Gallenkamp | 560/115 |
| 4,374,661 | 2/1983 | Fritz et al. | 71/86 |
| 4,401,454 | 8/1983 | Fritz et al. | 71/76 |
| 4,504,413 | 3/1985 | Khanna | 260/112 R |
| 4,556,409 | 12/1985 | Fayter, Jr. et al. | 71/76 |
| 4,570,014 | 2/1986 | Schroder et al. | 560/124 |
| 4,588,833 | 3/1986 | Kadelka et al. | 560/145 |
| 4,736,056 | 4/1988 | Smith et al. | 560/43 |

FOREIGN PATENT DOCUMENTS

| | | |
|---|---|---|
| 741252 | 8/1966 | Canada . |
| 49-116019 | 11/1974 | Japan . |
| 57-171904 | 10/1982 | Japan . |
| 39803 | 3/1984 | Japan . |
| 166651 | 8/1985 | Japan . |
| 1086326 | 11/1967 | United Kingdom . |
| 1162727 | 8/1969 | United Kingdom . |

OTHER PUBLICATIONS

Shindo, N. et al., Meiji Daigaku Noogaku bu Kenkyu Hokoku, vol. 63, pp. 41–58.
Baruffini, A. et al., Il Farmaco, Anno. XXII, N. 10, pp. 769–780 (Oct. 1967).
Boyd, R. N. et al. J. Amer. Chem. Soc., vol. 75, pp. 2762–2763 (1953).
Mikami, N. et al., J. Pesticide Sci. 4, pp. 165–174 (1979).
Najer, H. et al., Bull. Soc. Chim. Fr., vol. 7, pp. 2118–2120 (1965).
Mittal, A. K. et al., J. Ind. Chem. Soc. 59, (5), pp. 711–712 and 373–374 (1982).
Skinner, C. C. et al., J. Agr. Food Chem., vol. 21, No. 6, 1057–1060 (1973).
Sargent, D. R. et al., J. Agr. Food Chem. vol. 21, No. 6, pp. 1061–1065 (1973).
Abeles, Frederick B. *Ethylene In Plant Biology* Academic Press, New York & London, 1973.
The Agro Chemicals Handbook, Royal Society of Chemistry, England 1983.
Zirvi, et al., Il Farmaco Ed. Sc., vol. 32, fasc 7, Anno XXXI N.7.
Shindo, et al., Meiji Daigaku Nogakubu Kenkyu Hokoku 1985, (70) 83–90 (CAS 105:129320v).
Kuster, et al., Z. Physiol. Chem. 145, 45–52, 1925 (CAS 19:2808).
Black, et al., Aust. J. Chem. 1983, 36(6), 1133–40 (CAS 99:224044z).
Stewart, et al., J. Org. Chem. 30, 1951–55 (1965).
Kirby, et al., J. Chem. Soc., Perkin 2(14), 1753–61 (1976).
Michel, et al., Helv. Chim. Acta., 48(8), 1973–83 (1965).

*Primary Examiner*—Richard L. Raymond
*Assistant Examiner*—Brian G. Bembenick
*Attorney, Agent, or Firm*—Morgan & Finnegan

[57] ABSTRACT

This invention relates to synergistic plant growth regulator compositions containing (1) an ethylene response or ethylene-type response inducing agent and (11) a malonic acid derivative compound. This invention also relates to the use of said compositions for inducing synergistic plant growth regulating responses or ethylene responses or ethylene-type responses.

72 Claims, No Drawings

SYNERGISTIC PLANT GROWTH REGULATOR COMPOSITIONS

This application is a continuation-in-part of U.S. application Ser. No. 843,392, filed Mar. 31, 1986 (abandoned).

BRIEF SUMMARY OF THE INVENTION

1. Technical Field

This invention relates to synergistic plant growth regulator compositions and to the use of said compositions for inducing plant growth regulating responses or ethylene responses or ethylene-type responses.

2. Background of the Invention

Plant growth regulating responses involving the inducement of an ethylene response or ethylene-type response have been known for some time in the art and include, for example, increasing yields, abscission of foliage and fruit, increasing flowering and fruiting, prevention of lodging, disease resistance and other responses.

Ethylene response or ethylene-type response inducing agents which have been used to achieve certain of these plant growth regulating responses include, for example, the following: certain phosphonic acid compounds as described in U.S. Pat. Nos. 3,879,188, 4,240,819, 4,352,869, 4,374,661 and 4,401,454; certain 2-haloethanesulphinic acid compounds as described in U.S. Pat. No. 3,885,951; certain beta-chloro- and beta-bromoethanesulfinic acids and esters as described in U.S. Pat. No. 3,927,062; mixtures of a N-heterocyclic amide and a haloalkyl silane as described in U.S. Pat. No. 4,332,612; mixtures of a N-heterocyclic amide and a 2-haloethylsulfinate as described in U.S. Pat. No. 4,359,334; and gaseous ethylene as described by Parihar, N. S., Hormonal Control of Plant Growth, pp. 69-79 (1964).

Certain malonic acid derivative compounds have been described in the art as capable of providing plant growth regulating responses. U.S. Pat. No. 3,072,473 describes N-arylmalonamic acids and their esters and salts, N, N'-diarylmalonamides, N-alkyl-N-arylmalonamic acids and their esters and salts, and N, N'-dialkyl-N, N'-diarylmalonamides which may be useful as plant growth regulants and herbicides. Japanese Patent 84 39,803 (1984) describes malonic acid anilide derivative compounds which may be useful as plant growth regulators. The plant growth regulating properties of substituted malonyl monoanilides are described by Shindo, N. and Kato, M., Meiji Daigaku Noogaku-bu Kenkyu Hokoku, Vol. 63, pp. 41-58 (1984).

However, plant growth regulating compositions containing (1) an ethylene response or ethylene-type response inducing agent and (2) a malonic acid derivative compound, which compositions provide synergistic plant growth regulating responses as described herein, have not been disclosed in the art.

Accordingly, it is an object of this invention to provide novel synergistic plant growth regulating compositions. It is another object of this invention to provide a method for the use of the novel plant growth regulating compositions to achieve synergistic plant growth regulating responses. These and other objects will readily become apparent to those skilled in the art in light of the teachings herein set forth.

DISCLOSURE OF THE INVENTION

This invention relates to synergistic plant growth regulator compositions and to the inducement of a synergistic plant growth regulating response to an ethylene response or an ethylene-type response through the application of a synergistic plant growth regulator composition at the plant site.

In particular, this invention relates to synergistic plant growth regulator compositions containing (i) an ethylene response or ethylene-type response inducing agent and (ii) a malonic acid derivative compound having the formula:

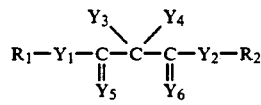

wherein $R_1$, $R_2$, $Y_1$, $Y_3$, $Y_4$, $Y_5$ and $Y_6$ are as defined hereinafter, and in which the amount of compound (ii) used with agent (i) results in a mixture having a greater plant growth regulating effect than the sum total plant growth regulating effect of agent (i) and compound (ii) used alone.

This invention further relates to a method for regulating plant growth by applying to the plant a synergistic plant growth regulator composition containing (i) an ethylene response or ethylene-type response inducing agent and (ii) a malonic acid derivative compound having the formula:

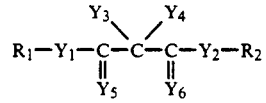

wherein $R_1$, $R_2$, $Y_1$, $Y_2$, $Y_3$, $Y_4$, and $Y_5$ and $Y_6$ are as defined hereinafter, and in which the amount of compound (ii) used with agent (i) results in a mixture having a greater plant growth regulating effect than the sum total plant growth regulating effect of agent (i) and compound (ii) used alone.

DETAILED DESCRIPTION

As indicated above, this invention relates to synergistic plant growth regulator compositions and to a method for inducing synergistic plant growth regulating responses by applying a synergistic plant growth regulator composition at the plant site. More particularly, this invention relates to plant growth regulator compositions comprising (i) an ethylene response or ethylene-type response inducing agent and (ii) a malonic acid derivative compound having the formula:

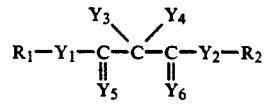

wherein:

$R_1$ and $R_2$ are independently a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents (Z) are the same or different and are one or more hydrogen, halogen, alkylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

—X, =X, —X=R₃, =X—R₃, —X—R₃,

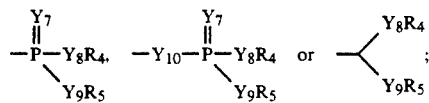

or

R₁ and R₂ are independently hydrogen or derivative salts, or a substituted heteroatom or substituted carbon atom, or a substituted or unsubstituted, branched or straight chain containing two or more carbon atoms or heteroatoms in any combination in which the permissible substituents (Z) are the same or different and are one or more hydrogen, halogen, alkylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyuloxy, polyfluoroalkanol, cyanoalkylamino, semiocarbazonomethyl, alkoxycarobnylhydrazonomethyl, alkoxyiminomethyl, unsubstituted or substituted aryloximinomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylamiosulfonyl, arylaminosulfonyl, carboxyalkyoxy, carboxylalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene, $-X$, $=X$, $-X=R_3$, $=X-R_3$, $-X-R_3$,

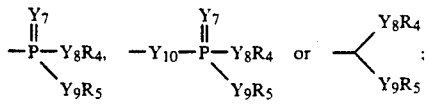

Y₁ and Y₂ are independently a substituted or unsubstituted heteroatom in which the permissible substituents (Z) are the same or different and are one or more hydrogen, halogen, alkylcarbonyl, alkylcarbonylalkyl, formyl,alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene, $-X$, $=X$, $-X=R_3$, $=X-R_3$, $-X-R_3$,

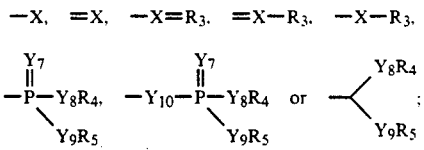

Y₃ and Y₄ are independently hydrogen, or a substituted or unsubstituted heteroatom or substituted carbon atom, or a substituted or unsubstituted, branched or straight chain containing two or more carbon atoms or heteroatoms in nay combination, or halogen, alkylcarbonyl, formyl, alkylcarbonylalkyl, alkoxycarbonylalkyl, alkoxycarbonylalkylthio, polyhaloalkenylthio, thiocyano, propargylthio, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, hydrazino, azo, aminocarbonyl, alkylaminocarbonyl, azido, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino,

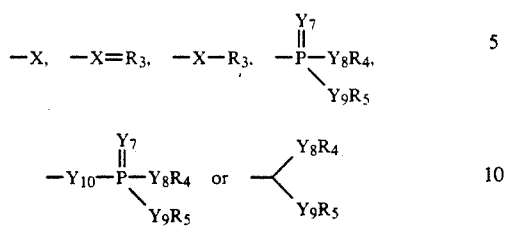

in which the permissible substituents (Z) are the same or different and are one or more hydrogen, halogen, alkylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

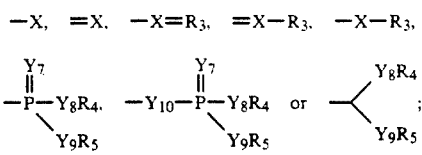

or $Y_3$ and $Y_4$ taken together are oxo, thiono, diazo, $=X$ or $=X-R_3$, or substituted or unsubstituted alkylidene, alkylimino, hydrazono, dialkylsulfonium, dialkyloxosulfonium, semicarbazono, hydroxyimino, alkoxyimino or aryloxyimino in which the permissible substituents (Z) are the same or different and are one or more hydrogen, halogen, alkylcarbonyl, formyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

—X, =X, —X=R$_3$, =X—R$_3$, —X—R$_3$,

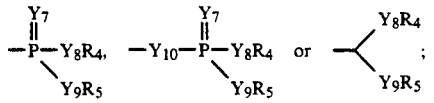

or

Y$_3$ and Y$_4$ may be linked together to form a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents (Z) are the same or different and ar one or more hydrogen, halogen, alkylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

—X, =X, —X=R$_3$, =X—R$_3$, —X—R$_3$,

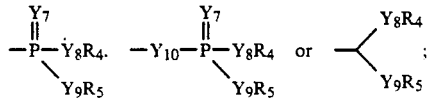

and Y$_5$ and Y$_6$ are independently oxygen or sulfur: wherein:

X is a covalent single bond or double bond, a substituted or unsubstituted heteroatom or substituted carbon atom, or a substituted or unsubstituted, branched or straight chain containing two or more carbon atoms or heteroatoms in any combination in which the permissible substituents (Z) are the same or different and are one or more hydrogen, halogen, alkylcarbonyl, formyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

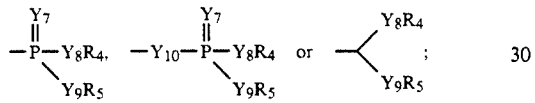

$R_3$ is a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents (Z) are the same or different and are one or more hydrogen, halogen, alkylcarbonyl, formyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, or di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

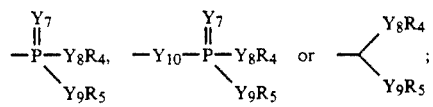

or $R_3$ is a substituted heteroatom or substituted carbon atom, or a substituted or unsubstituted, branched or straight chain containing two or more carbon atoms or heteroatoms in any combination in which the permissible substituents (Z) are the same or different and are one or more hydrogen, halogen, alkylcarbonyl, formyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkyoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

—X, =X, —X=R₃, =X—R₃, —X—R₃,

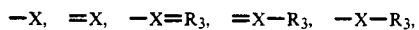
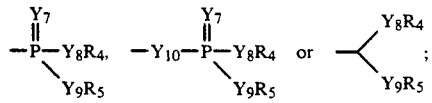

Y₇ and Y₁₀ are independently oxygen or sulfur;
Y₈ and Y₉ are independently oxygen, sulfur, amino or a covalent single bond; and
R₄ and R₅ are independently hydrogen or substituted or unsubstituted alkyl, alkenyl, alkynyl, polyhaloalkyl, phenyl or benzyl in which the permissible substituents (Z) are the same or different and are one or more hydrogen, halogen, alkylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloacyl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkylsulfuranylidene, dialkyloxosulfuranylidene,

—X, =X, —X=R₃, =X—R₃, —X—R₃,

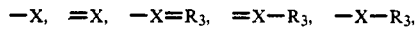
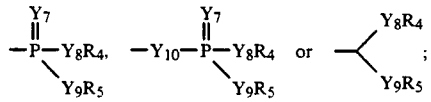

in which the amount of compound (ii) used with agent (i) results in a mixture having a greater plant growth regulating effect than the sum total plant growth regulating effect of agent (i) and compound (ii) used alone.

The alkyl-containing moieties in formula 1 may contain from about 1 to about 100 carbon atoms or greater, preferably from about 1 to about 30 carbon atoms, and more preferably from about 1 to about 20 carbon atoms. The polysaccharide moiety may contain up to about 50 carbon atoms. It is appreciated that all compounds encompassed within formula 1 are compounds having no unfilled bonding positions. In regard to the malonic acid derivative compounds used in the synergistic plant growth regulator compositions of this invention, it is preferred that of $R_1Y_1$ and $R_2Y_2$ one, but not both, by aryl—NH—.

As used herein, hydrogen or derivative salts refer to hydrogen or any appropriate derivative salt substituents which may be substituted therefor. Illustrative derivative salt substituents include, for example, ammonium, alkylammonium, polyalkylammonium, hydroxyalkylammonium, poly(hydroxyalkyl)ammonium, alkali metals, alkaline earth metals and the like including mixtures thereof.

Monocyclic ring systems encompassed by $R_1$, $R_2$ and $R_3$ in formula 1 may be represented by generalized formula 2 as follows:

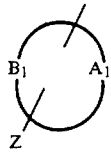

wherein $B_1$ represents a saturated or unsaturated carbon atom and $A_1$ represents a ring-forming chain of atoms which together with $B_1$ forms a cyclic system containing from 0 to 3 double bonds or from 0 to 2 triple bonds. $A_1$ may contain entirely from 2 to 12 carbon atoms, may contain a combination of from 1 to 11 carbon atoms and from 1 to 4 heteroatoms which may be selected independently from N, O, S, P or other heteroatoms, or may contain 4 ring-forming heteroatoms alone.

Monocyclic ring systems encompassed by $Y_3$ and $Y_4$ linked together in formula 1 may include any monocyclic ring system of $R_1$, $R_2$ and $R_3$ appropriately positioned in formula 1.

Ring-forming heteroatoms may in some cases bear oxygen atoms as in aromatic N-oxides and ring systems containing the sulfinyl, sulfonyl, selenoxide and phosphine oxide moieties.

Selected carbon atoms contained in cycles formed by $B_1$ and $A_1$ containing at least 3 ring-forming atoms may bear carbonyl, thiocarbonyl, substituted or unsubstituted imino groups or substituted or unsubstituted methylidene groups.

The group designated as Z represents one or more substituents selected independently from among the group of substituents defined for Z herein.

Illustrative monocyclic ring structures which are encompassed by $R_1$, $R_2$ and $R_3$ in formula 1 include the following:

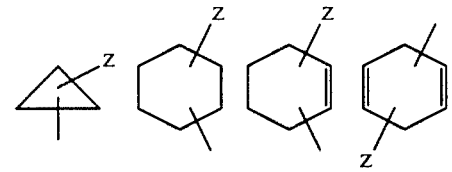

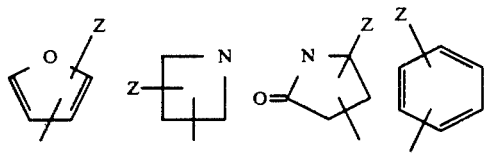

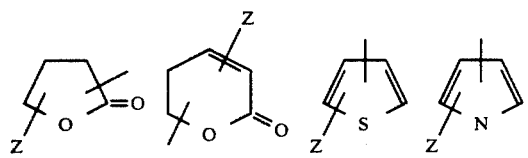

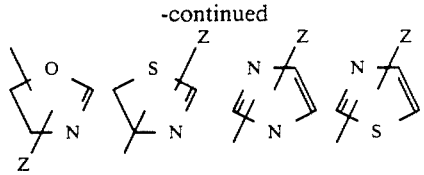

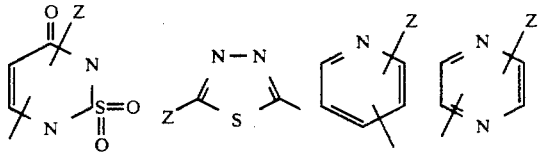

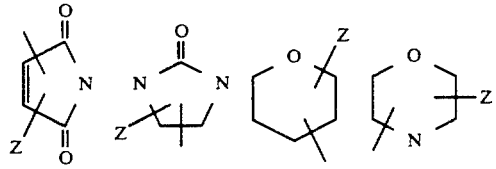

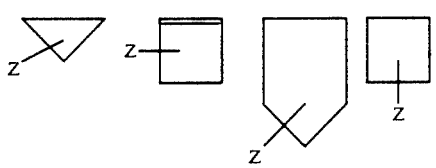

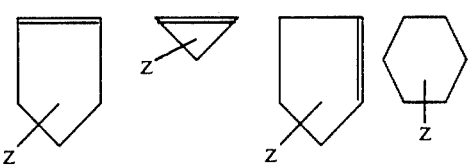

wherein Z is as defined herein.

Bicyclic ring systems encompassed by $R_1$, $R_2$ and $R_3$ in formula 1 may be represented by generalized formulae 3 and 4 as follows:

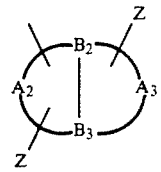

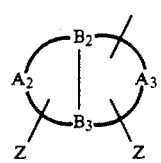

wherein $B_2$ and $B_3$ may be independently a saturated or unsaturated carbon atom or a saturated nitrogen atom, $A_2$ and $A_3$ independently represent the ring-forming chains of atoms described below and Z represents one or more substituents selected independently from among the group of substituents defined for Z herein. Combinations of $A_2$ and $A_3$ may contain in combination with $B_2$ or $B_3$ from 0 to 5 double bonds. $A_2$ and $A_3$, independent of $B_2$ and $B_3$, may contain entirely from 1 to 11 carbon atoms, may contain a combination of 1 to 3 heteroatoms which may be selected independently from among N, O, S, P or other heteroatoms together with from 1 to 10 carbon atoms or may contain from 1-3 ring-forming heteroatoms alone.

Ring-forming heteroatoms may in some cases bear oxygen atoms, as in aromatic N-oxides and ring systems containing the sulfinyl, sulfonyl, selenoxide and phosphine oxide groups. Selected carbon atoms contained in $A_2$ and $A_3$ may bear carbonyl, thiocarbonyl, substituted or unsubstituted imino groups or substituted or unsubstituted methylidene groups.

Bicyclic ring systems encompassed by $Y_3$ and $Y_4$ linked together in formula 1 may include any bicyclic ring system of $R_1$, $R_2$ and $R_3$ appropriately positioned in formula 1.

In regard to structures encompassed within formulae 3 and 4, it is noted as follows:

(a) When $B_2$ and $B_3$ are both nitrogen, the groups $A_2$ and $A_3$ should each contain no fewer than three ring atoms;

(b) When $B_2$ but not $B_3$ is nitrogen, either of $A_2$ or $A_3$ should contain at least three ring atoms and the other at least two ring atoms;

(c) When either of groups $A_2$ or $A_3$ contains fewer than three ring atoms, the other should contain at least three ring atoms and the bridgehead atoms should be saturated;

(d) When the group $A_2$ or $A_3$ contains a carbon atom bearing a carbonyl, thiocarbonyl, imino or methylidene group, it should together with $B_2$ and $B_3$ form a cycle having at least four members;

(e) When a annular double bond is exocyclic to either of the two rings represented in structures 3 and 4, it should be contained in a ring containing at least five members and be exocyclic to a ring containing at least five members; and (f) When a group $A_2$ or $A_3$ is joined to the bridgehead atoms $B_2$ and $B_3$ by 2 double bonds, the group $A_2$ or $A_3$ is understood to contain one double bond and the bridgehead atoms are considered to be unsaturated.

It is recognized that bicyclic ring systems defined for $R_1$, $R_2$, $R_3$ and $Y_3$ and $Y_4$ linked together may be spirocyclic ring systems and are not limited to the fused bicyclic structures of formulae 3 and 4. Spirocyclic ring systems may be saturated or unsaturated carbocyclic or heterocyclic and may be independently substituted by one or more substituents Z as defined herein.

Illustrative bicyclic ring structures which are encompassed by $R_1$, $R_2$ and $R_3$ in formula 1 included the following:

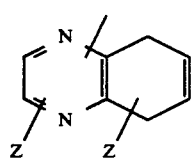

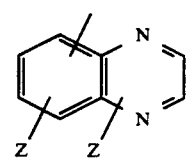

-continued

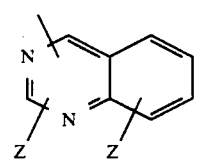

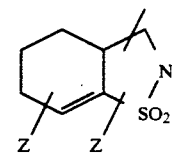

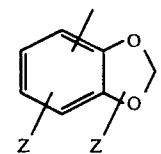

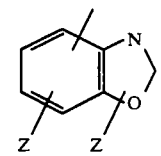

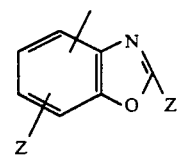

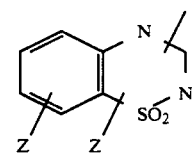

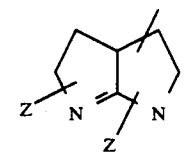

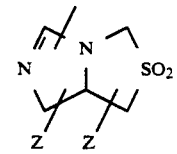

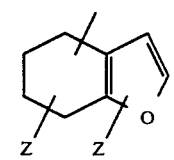

19
-continued
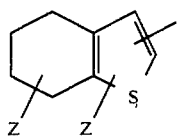
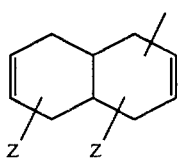
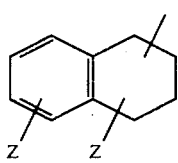
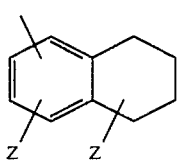
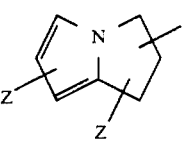
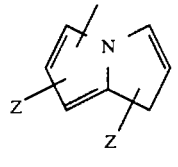
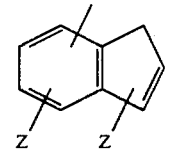
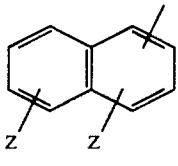
20
-continued
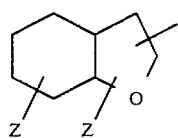
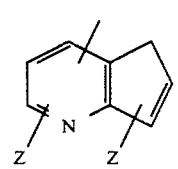
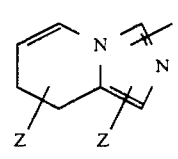
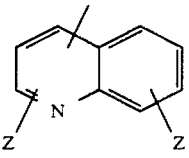
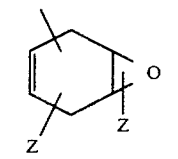
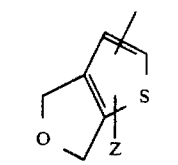
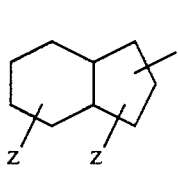
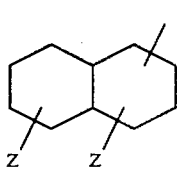
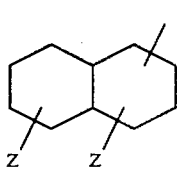

21
-continued
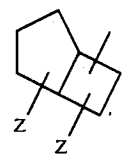
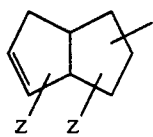
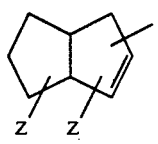
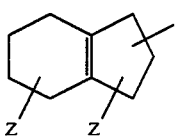
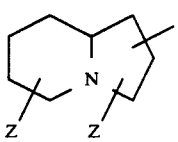
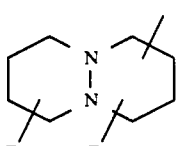
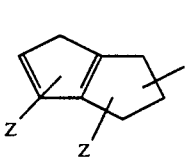
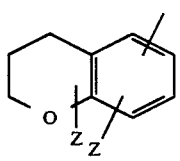
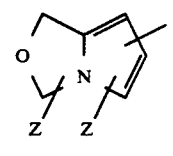
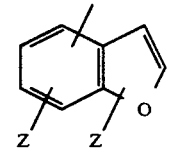
22
-continued
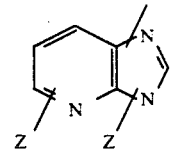
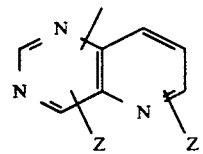
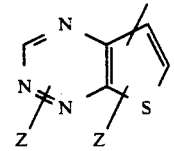
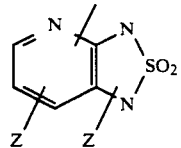
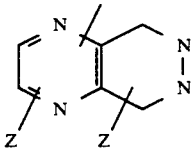
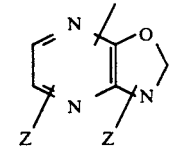
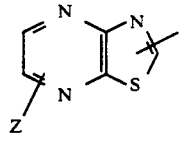
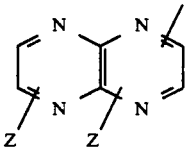
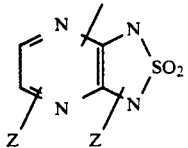

-continued
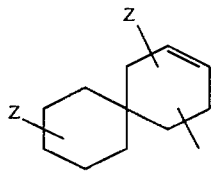
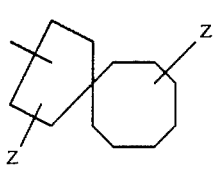
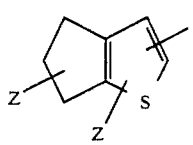
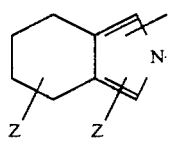
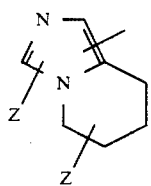
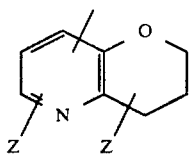
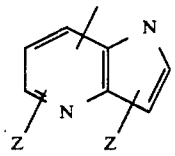
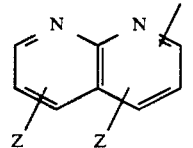
-continued
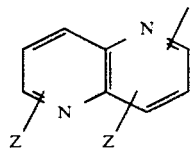
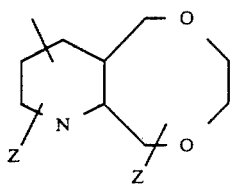
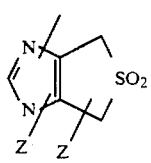
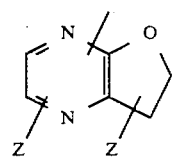
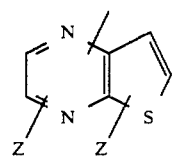
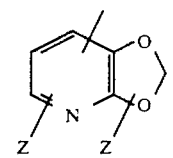
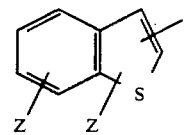
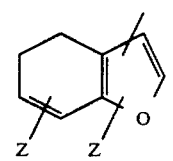
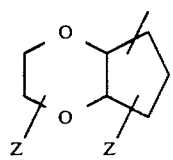

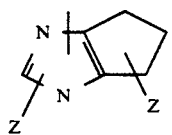

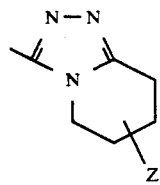

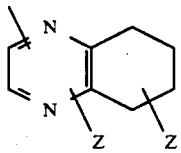

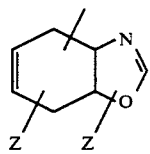

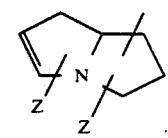

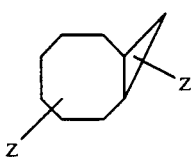

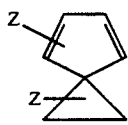

Polycyclic ring systems, i.e., greater than 2 rings, encompassed by $R_1$, $R_2$ and $R_3$ in formula 1 may be represented by generalized formulae 5, 6, 7 and 8 as follows:

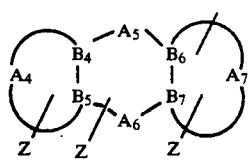

(5)

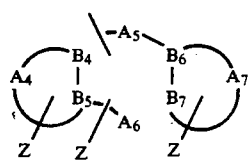

(6)

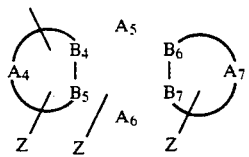

(7)

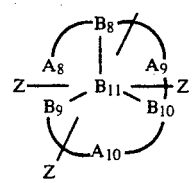

(8)

wherein $B_4$, $B_5$, $B_6$ and $B_7$ may be independently a saturated or unsaturated carbon atom or a saturated nitrogen atom, and $A_4$, $A_5$, $A_6$ and $A_7$ independently represent ring forming chains of atoms which may contain together with one or the other (but not both) of their two associated bridgehead atoms, from 0-2 double bonds. The groups Z represent one or more substituents selected independently from among the group of substituents defined for Z herein.

The ring-forming elements of $A_4$, $A_5$, $A_6$ and $A_7$ independent of $B_4$, $B_5$, $B_6$ and $B_7$ may contain from 1-11 carbon atoms, may contain a combination of from 1-10 carbon atoms and from 1-3 heteroatoms which may be selected independently from among N, O, S, P or other heteroatoms, or may contain from 1-3 heteroatoms alone. Ring-forming heteroatoms may in some cases bear oxygen atoms as in aromatic N-oxides and ring systems containing the sulfinyl, sulfonyl, selenoxide and phosphine oxide groups. The group $A_6$ may at times be defined as a bond. Selected carbon atoms contained in $A_4$, $A_5$, $A_6$ and $A_7$ may bear one or more carbonyl, thiocarbonyl or substituted or unsubstituted imino groups.

On structure 8 the groups $B_8$, $B_9$ and $B_{10}$ represent independently a saturated or unsaturated carbon atom or a saturated nitrogen atom. The group $B_{11}$ may represent a saturated or unsaturated carbon atom or a nitrogen or phosphorous atom. The groups $A_8$, $A_9$ and $A_{10}$ represent ring-forming chains of atoms which may contain together with 1 or the groups $B_8$, $B_9$, $B_{10}$ and $B_{11}$ from 0-2 double bonds.

The ring-forming elements of groups $A_8$, $A_9$ and $A_{10}$ independent of groups $B_8$, $B_9$, $B_{10}$ and $B_{11}$ may contain from 2-10 carbon atoms, may contain from 1-10 carbon atoms in combination with 1-3 heteroatoms which may be selected independently from among N, O, S, P or other heteroatoms, or may contain from 2-3 heteroatoms alone. Ring-forming heteroatoms may in some cases bear oxygen atoms as in aromatic N-oxides and in ring systems containing the sulfinyl, sulfonyl, selenoxide and phosphine oxide groups. Selected carbon atoms contained in groups $A_8$, $A_9$ and $A_{10}$ may bear one or more carbonyl, thiocarbonyl or substituted or unsubstituted imino groups.

It is recognized that polycyclic ring systems defined for $R_1$, $R_2$, $R_3$ and $Y_3$ and $Y_4$ linked together may be spirocyclic ring systems and are not limited to the fused polycyclic structures of formulae 5, 6, 7 and 8. Spirocyclic ring systems may be saturated or unsaturated, carbocyclic or heterocyclic and may be independently substituted by one or more substituents Z as defined herein.

Polycyclic ring systems encompassed by $Y_3$ and $Y_4$ linked together in formula 1 may include any polycyclic ring system of $R_1$, $R_2$ and $R_3$ appropriately positioned in formula 1.

Illustrative polycyclic ring structures which are encompassed by $R_1$, $R_2$ and $R_3$ in formula 1 include the following:

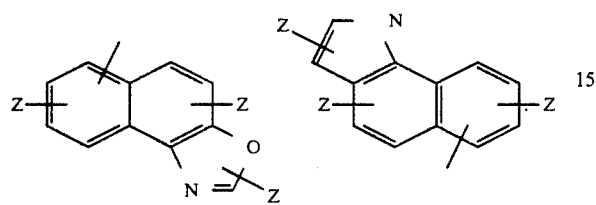

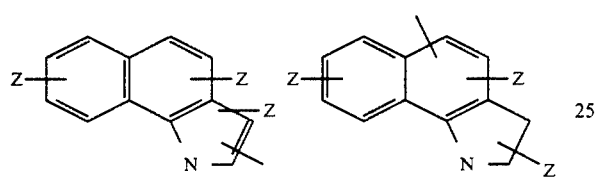

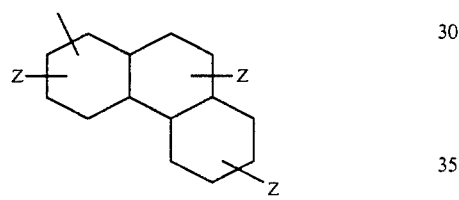

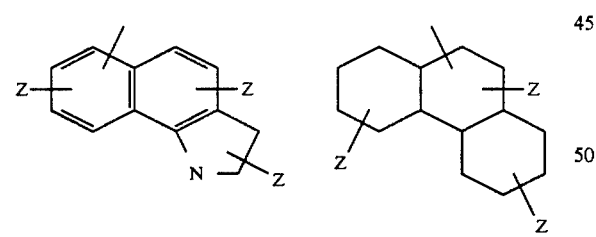

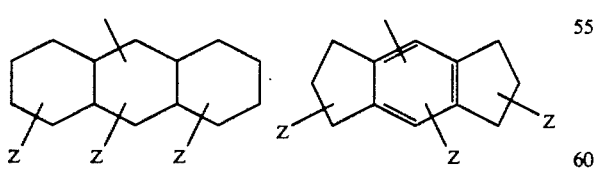

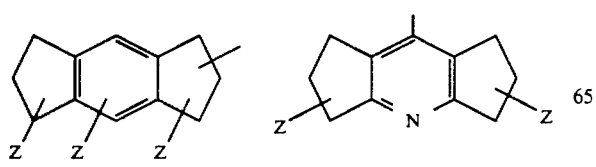

-continued

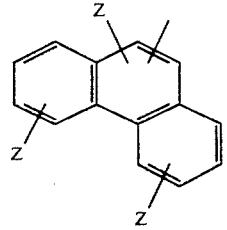

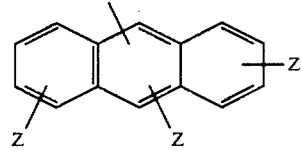

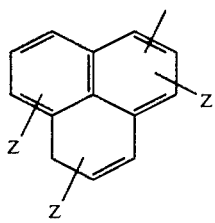

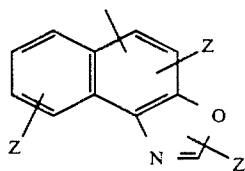

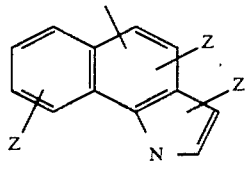

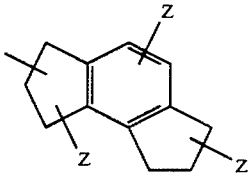

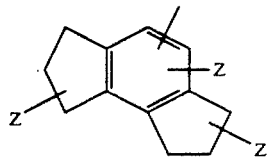

-continued

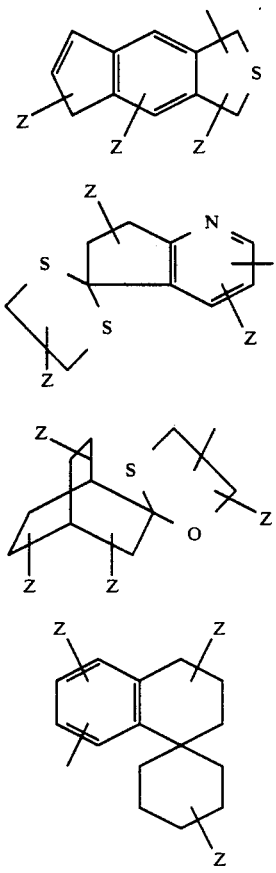

Bridge bicyclic structures encompassed by $R_1$, $R_2$ and $R_3$ in formula 1 may be represented by generalized formulae 9, 10, and 11 as follows:

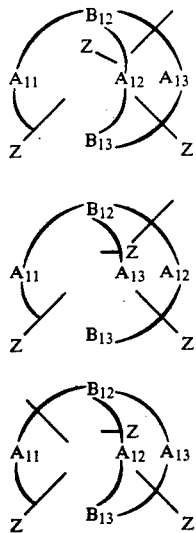

9

10

11 wherein $B_{12}$ and $B_{13}$ may be independently a saturated carbon atom optionally substituted by Z or a nitrogen atom, and the groups $A_{11}$, $A_{12}$ and $A_{13}$ independently represent ring-forming chains of atoms which may contain, independently of $B_{12}$ and $B_{13}$, from 0-2 double bonds. The groups Z represent one or more substituents selected independently from among the groups of substituents defined for Z herein.

The ring-forming elements of $A_{11}$, $A_{12}$ and $A_{13}$, independent of $B_{12}$ and $B_{13}$, may contain entirely from 1-11 carbon atoms, may contain a combination of from 1-10 carbon atoms and from 1-3 heteroatoms which may be selected independently from among N, O, S, P or other heteroatoms, or may contain from 1-3 heteroatoms alone with the proviso that when one of the groups $A_{11}$, $A_{12}$ and $A_{13}$ is a single heteroatoms, the other two groups should contain two or more ring-forming atoms. A second proviso is that when one or both of the groups $B_{12}$ and $B_{13}$ is nitrogen, the groups $A_{11}$, $A_{12}$ and $A_{13}$ should contain at least two saturated ring-forming atoms.

Ring-forming heteroatoms may in some cases bear oxygen atoms as in the sulfinyl, sulfonyl, selenoxide and phosphine oxide moieties. Selected carbon atoms contained in $A_{11}$, $A_{12}$ and $A_{13}$ may bear one or more carbonyl, thiocarbonyl or substituted or unsubstituted imino groups.

Bridged bicyclic structures encompassed by $Y_3$ and $Y_4$ linked together in formula 1 may include any bicyclic bridged system of $R_1$, $R_2$ and $R_3$ appropriately positioned in formula 1.

Illustrative bridged bicyclic structures which are encompassed by $R_1$, $R_2$ and $R_3$ in formula 1 include the following:

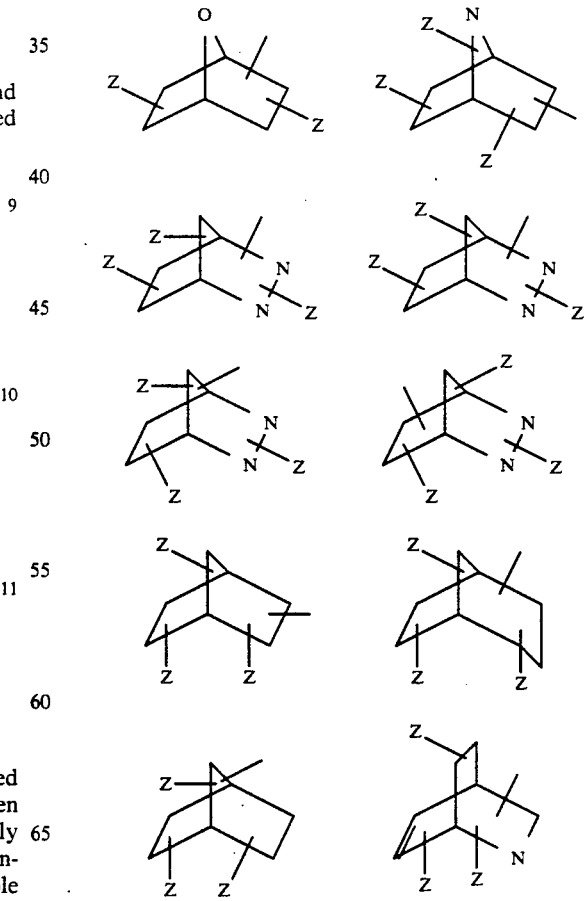

-continued
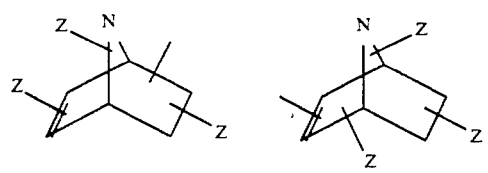
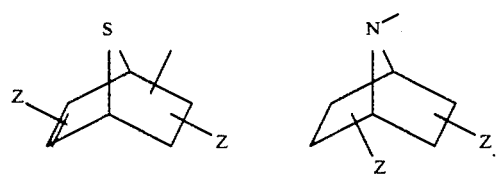
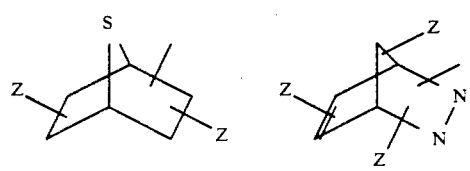
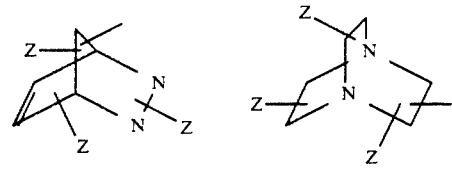
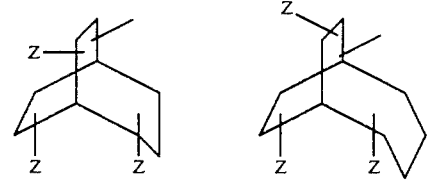
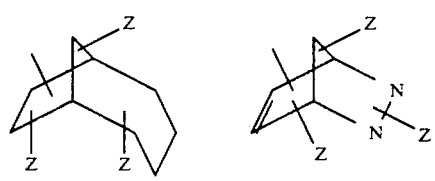
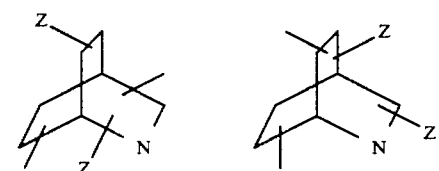
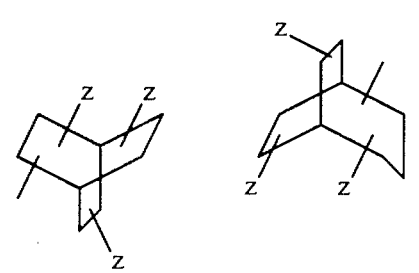
-continued
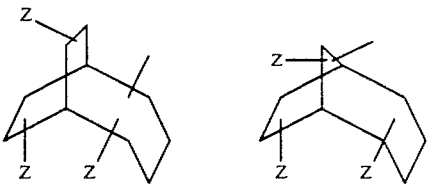
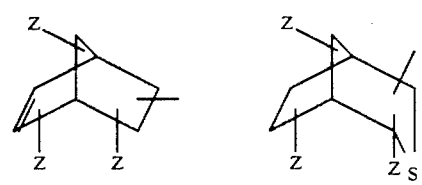
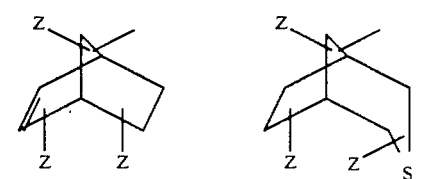
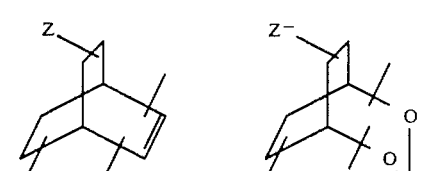
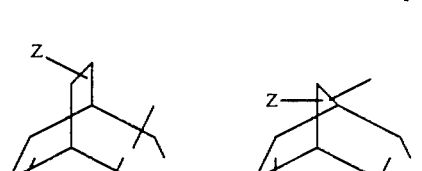
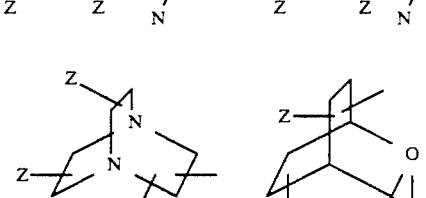
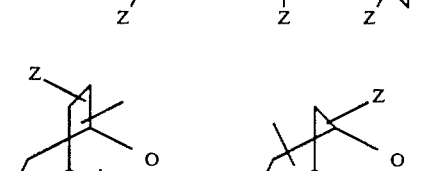
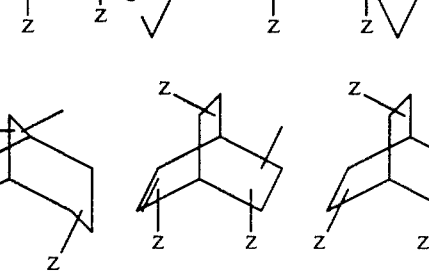

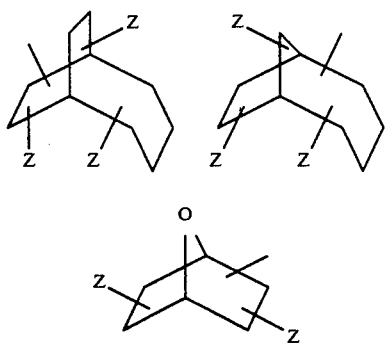

It is readily apparent that formula 1 encompasses a wide variety of malonic acid derivative compounds. Illustrative malonic acid derivative compounds within the scope of formula 1 which may be used in the synergistic plant growth regulator compositions of this invention are included in Tables 1 through 11 below.

TABLE 1

Representative Malonic Acid Derivative Compounds $$R'_7-\overset{O}{\underset{\|}{C}}-CH_2-\overset{O}{\underset{\|}{C}}-NH-\text{C}_6H_4-Z'_8$$

| $Z'_8$ | $R'_7$ |
|---|---|
| 3-F-5-Cl | $OC_2H_5$ |
| 3-F-5-Cl | $OCH_3$ |
| 3-F-5-Cl | OH |
| 3-F-5-Br | $OC_2H_5$ |
| 3-F-5-Br | ONa |
| 3-$CF_3$-5-Cl | $OCH_3$ |
| 3-$CF_3$-5-Cl | $ONH_4$ |
| 3-$CF_3$-5-Br | $OC_2H_5$ |
| 3-$CF_3$-5-Br | $NH_2$ |
| 3-$CF_3$-5-Br | OH |
| 3-F-4-Cl | $OC_2H_5$ |
| 3-F-4-Cl | $OCH_3$ |
| 3-F-4-Cl | OK |
| 3-F-4-Br | OH |
| 3-F-4-Br | $OCH_3$ |
| 3-F-4-Br | O-n-$C_3H_7$ |
| 2-F-4,5-$Cl_2$ | OH |
| 2-F-4,5-$Cl_2$ | $OC_2H_5$ |
| 2-F-4-Cl-5-Br | OH |
| 2-F-4-Cl-5-Br | $OCH_3$ |
| 2-F-4-Br-5-Cl | OH |
| 2-F-4-Br-5-Cl | $OC_2H_5$ |
| 2-F-4,5-$Br_2$ | OH |
| 2-F-4,5-$Br_2$ | $OCH_3$ |
| 2-F-4,5-$Br_2$ | $ONH_4$ |
| 2,4-$Cl_2$-5-F | OH |
| 2,4-$Cl_2$-5-F | $OC_2H_5$ |
| 2-Cl-4-Br-5-F | $OCH_3$ |
| 2-Cl-4-Br-5-F | O-n-$C_3H_7$ |
| 2,4-$Br_2$-5-F | OH |
| 2,4-$Br_2$-5-F | $OCH_3$ |
| 2-Br-4-Cl-5-F | OH |
| 2-Br-4-Cl-5-F | $OC_2H_5$ |
| 2-$CH_3$-4-Cl-5-F | OH |
| 2-$CH_3$-4-Cl-5-F | $OC_2H_5$ |
| 2-$CH_3$-4-Cl-5-F | ONa |
| 2-$CH_3$-4-Br-5-F | OH |
| 2-$CH_3$-4-Br-5-F | O-n-$C_4H_9$ |
| 2-$CH_3$-4-Br-5-F | OK |
| 2-Cl-4-$CF_3$O | $OCH_3$ |
| 2-$CF_3$O-4-Br | $OC_2H_5$ |
| 2-$CH_3$-4-$CF_3CF_2$O— | O-n-$C_3H_7$ |
| 2-$CH_3$-4-I | $OCH_3$ |
| 2-F-4-I | $OC_2H_5$ |
| 2-$CH_3$O-3,5-$Br_2$ | ONa |
| 3-Br-4-Cl | $OC_2H_5$ |

TABLE 1-continued

Representative Malonic Acid Derivative Compounds $$R'_7-\overset{O}{\underset{\|}{C}}-CH_2-\overset{O}{\underset{\|}{C}}-NH-\text{C}_6H_4-Z'_8$$

| $Z'_8$ | $R'_7$ |
|---|---|
| 2,4-$Cl_2$ | $NHCH_3$ |

TABLE 2

Representative Malonic Acid Derivative Compounds $$R'_8-\overset{O}{\underset{\|}{C}}-CH_2-\overset{O}{\underset{\|}{C}}-NH-\text{C}_6H_4-Z'_9$$

| $R'_8$ | $Z'_9$ |
|---|---|
| $OCH_2CH_2OH$ | 2-$CH_3$-4-Br |
| $OCH_2CH_2OH$ | 2-F-4-Br |
| $OCH_2CH_2OH$ | 3,4-$Cl_2$ |
| $OCH(CH_3)CO_2C_2H_5$ | 2-$CH_3$-4-Br |
| $OCH(CH_3)CO_2C_2H_5$ | 4-Cl |
| $OCH_2CH_2N(CH_3)_2$ | 2,4-$Br_2$ |
| $SCH_3$ | 2,4,5-$Cl_3$ |
| S—$C_6H_5$ | 3,5-$Br_2$ |
| S—$C_3H_7$ | 2,4-$Cl_2$ |
| $OCH_2CO_2C_2H_5$ | 3-F-5-Br |
| $SCH_2CO_2C_2H_5$ | 2-$CH_3$-4-Br |
| $SCH_2CO_2C_2H_5$ | 2-$CH_3$-4-Br-5-Cl |
| $OCH_2CH_2SCH_3$ | 2-F-4-Br |
| $OCH_2CH_2SO_2CH_3$ | 3,5-$Cl_2$ |
| $OCH_2CH_2SO_2CH_3$ | 3,5-$Br_2$ |
| $OCH_2\overset{O}{\underset{\|}{C}}CH_3$ | 3-Br-5-Cl |
| $OCH_2\overset{O}{\underset{\|}{C}}CH_3$ | 2,4-$Cl_2$ |
| $OCH(CH_3)C\equiv N$ | 2-$CH_3$-4-Br |
| $OCH(CH_3)C\equiv N$ | 4-Br |
| $O-N=CHCH_3$ | 4-Cl |
| $O-N=C(CH_3)_2$ | 3,4-$Cl_2$ |
| $O-N=C(CH_3)(SCH_3)$ | 2,4-$Cl_2$ |
| $O-N=C(CH_3)(SCH_3)$ | 2-$CH_3$-4-Cl |
| $OCH_2CH_2NHCO_2CH_3$ | 2-$CH_3$-4-Br |
| $OCH_2CH_2O-\overset{O}{\underset{\|}{C}}-NHC_2H_5$ | 4-Cl |
| $OCH_2\overset{OC_2H_5}{\underset{\|}{\underset{O}{P}}}OC_2H_5$ | 2-F-4-$CF_3$ |
| $OCH_2CH_2\overset{OCH_3}{\underset{\|}{\underset{O}{P}}}OCH_3$ | 2,4-$Cl_2$ |

TABLE 2-continued

Representative Malonic Acid Derivative Compounds $$R'_8-\overset{O}{\overset{\|}{C}}-CH_2-\overset{O}{\overset{\|}{C}}-NH-\underset{}{\text{C}_6H_4}-Z'_9$$

| R'$_8$ | Z'$_9$ |
|---|---|
| SCH$_2$P(=O)(OCH$_3$)(OCH$_3$) | 3,4-Cl$_2$ |
| OCH$_2$CONH$_2$ | 3,5 (CF$_3$)$_2$ |
| SCH$_2$CH$_2$P(=O)(OC$_2$H$_5$)(OC$_2$H$_5$) | 3-Br-5-Cl |
| SCH$_2$CH$_2$P(=O)(OC$_6$H$_5$)(OC$_6$H$_5$) | 3-Cl-5-CF$_3$ |
| OCH$_2$CH$_2$SCH$_2$CH$_2$OH | 3-Br-5-CF$_3$ |
| OCH$_2$CH$_2$SO$_2$CH$_2$CH$_2$OH | 3-F-4-Br |
| OCH$_2$C≡N | 4-I |
| OCH$_2$CH$_2$C≡N | 2,4-Cl$_2$ |
| O—C(CH$_3$)$_2$C≡N | 4-Cl |
| OCH$_2$CH$_2$OCH$_3$ | 3-F-5-Cl |
| OCH$_2$CO$_2$C$_2$H$_5$ | 3-F-4-Cl |
| OCH$_2$CH$_2$N(thiomorpholinyl) | 2-F-4,5-Cl$_2$ |
| OCH(CH$_3$)CH$_2$SC$_2$H$_5$ | 2-F-4-Cl-5-Br |
| OCH$_2$COCH$_3$ | 2-F-4-Br-5-Cl |
| OCH$_2$C≡N | 2-F-4,5-Br$_2$ |
| O—N=C(CH$_3$)—CO$_2$C$_2$H$_5$ | 2,4-Cl$_2$-5-F |
| O—CH$_2$SO$_2$NH$_2$ | 2-Cl-4-Br-5-F |
| O—CH$_2$SO$_2$NHCH$_3$ | 2,4 Br$_2$-5-F |
| O—CH$_2$SO$_2$N(C$_2$H$_5$)$_2$ | 2-Br-4-Cl-5-F |
| S—CH$_2$CH$_2$SCH$_3$ | 2-CH$_3$-4-Cl-5-F |
| S—CH$_2$CO$_2$C$_3$H$_7$ | 2-CH$_3$-4-Br-5-F |
| OCH$_2$CH$_2$OC$_2$H$_5$ | 2-F-4-CF$_3$O |
| OCH$_2$CH$_2$SCH$_3$ | 2-F-4-I |
| OCH(CH$_3$)CO$_2$C$_2$H$_5$ | 3-Br-4-Cl |
| SC$_6$H$_5$ | 2-CF$_3$O-4-F |
| NHCH$_2$CH$_2$OH | 2-CH$_3$-4-Br |
| NHCH$_2$CH$_2$OH | 3-F-4-Cl |
| NHCH$_2$CN | 3,5-Cl$_2$ |
| NHCH$_2$CO$_2$CO$_2$C$_2$H$_5$ | 2-CH$_3$-4-Br |
| NHCH$_2$CO$_2$C$_2$H$_5$ | 2-F-4-Br |
| NHCH$_2$CN | 2,4-Br$_2$ |

TABLE 3

Representative Malonic Acid Derivative Compounds $$R'_9-\overset{Y'_4}{\underset{\overset{\|}{O}}{C}}-\overset{Y'_5}{C}-\overset{}{\underset{\overset{\|}{O}}{C}}-NH-\underset{}{\text{C}_6H_4}-Z'_{10}$$

| Y'$_4$ | Y'$_5$ | Z'$_{10}$ | R'$_9$ |
|---|---|---|---|
| Cl | Cl | 2-CH$_3$-4-Br | OC$_2$H$_5$ |
| Cl | H | 4-Cl | OC$_2$H$_5$ |
| Br | Br | 2,4-Cl$_2$ | OC$_2$H$_5$ |
| Br | H | 3,5-Br$_2$ | OC$_2$H$_5$ |
| Cl | Br | 3,4-Cl$_2$ | OCH$_3$ |
| CH$_3$ | Cl | 3,5-Cl$_2$ | OH |
| F | F | 2,4-Br$_2$ | OC$_2$H$_5$ |
| F | F | 2-F-4-Br | OC$_2$H$_5$ |

TABLE 3-continued

Representative Malonic Acid Derivative Compounds

| Y'$_4$ | Y'$_5$ | Z'$_{10}$ | R'$_9$ |
|---|---|---|---|
| CH$_3$O— | H | 2-F-4-Cl | O-n-C$_3$H$_7$ |
| CH$_3$O— | CH$_3$O— | 3-Cl-5-Br | OCH$_2$CH$_2$OCH$_3$ |
| F | H | 3,4-Br$_2$ | SCH$_2$CO$_2$C$_2$H$_5$ |
| O$_2$N— | H | 2-Cl-4-Br | OCH$_3$ |
| O$_2$N— | H | 2-Cl-4-Br | OCH(CH$_3$)C≡N |
| O$_2$N— | O$_2$N— | 2-CH$_3$-4-Br | SC$_2$H$_5$ |
| O$_2$N— | CH$_3$ | 2,4-Br$_2$ | ON=C(CH$_3$)$_2$ |
| CF$_3$ | H | 3,4-Br$_2$ | OC$_2$H$_5$ |
| CF$_3$ | CH$_3$ | 4-Cl | O-n-C$_3$H$_7$ |
| (CH$_3$)$_2$N | H | 2,4-Cl$_2$ | OC$_2$H$_5$ |
| CH$_2$=CH— | H | 3,5-Br$_2$ | OH |
| N≡C— | H | 2-CH$_3$-4-Br | OC$_2$H$_5$ |
| N≡C— | H | 2,4-Cl$_2$ | OCH$_3$ |
| N≡C— | CH$_3$ | 3-F-4-Br | OCH$_2$CONH$_2$ |
| O$_2$N— | Cl | 2,4,5-Cl$_3$ | OCH$_2$CH$_2$OH |
| N≡C— | Br | 3-Br-5-F | OCH$_2$CH$_2$SCH$_3$ |
| HCONH— | H | 3,5-(CF$_3$)$_2$ | OC$_2$H$_5$ |
| HC≡C— | H | 2,5-Cl$_2$ | SC$_6$H$_5$ |
| C$_2$H$_5$ | F | 3-Cl-5-CF$_3$ | OCH$_2$COCH$_3$ |
| CH$_3$O— | CH$_3$ | 4-Br | OCH$_3$ |
| cyclopropyl | H | 4-Cl | OC$_2$H$_5$ |
| cyclopropyl | CH$_3$ | 2-CF$_3$-4-Cl | OH |
| HO— | HO— | 2-CH$_3$-4-Br | OC$_2$H$_5$ |
| CH$_3$ | H | 2-Cl-4-CF$_3$O | SC$_6$H$_5$ |
| CH$_3$ | CH$_3$ | 2-CF$_3$O-4-F | OCH$_3$ |
| CH$_3$ | Br | 2-CH$_3$-4-CF$_3$CF$_2$O | O-n-C$_3$H$_7$ |
| CH$_3$ | C$_2$H$_5$ | 2-CH$_3$-4-I | OH |
| C$_2$H$_5$ | Br | 3-Br-4-Cl | OC$_2$H$_5$ |
| CH$_3$O | CH$_3$ | 2-F-4-I | ONa |
| HOCH$_2$— | HOCH$_2$ | 2,4-Cl$_2$ | OCH$_3$ |
| CH$_3$CO— | H | 4-Br | OC$_2$H$_5$ |
| CH$_3$CO— | CH$_3$ | 2-Cl-4-Br | OCH$_3$ |
| —CHO | Br | 2-CH$_3$-4-Cl | SCH$_3$ |
| —CHO | Cl | 3,4-Br$_2$ | OC$_2$H$_5$ |
| (C$_2$H$_5$O)$_2$CH— | Cl | 4-Cl | OCH$_3$ |
| (CH$_3$O)$_2$CH— | Br | 2-CH$_3$4-Br | O-n-C$_3$H$_7$ |
| H$_2$NC(=S)— | CH$_3$ | 2,4-Cl$_2$ | OCH$_3$ |
| CH$_3$CONH— | H | 2-CH$_3$-4-Br | SC$_2$H$_5$ |
| HCONH— | H | 2-F-4-Br | SC$_6$H$_5$ |
| HCl.H$_2$N— | H | 2-C$_2$H$_5$-4-Cl | OCH$_3$ |
| —O—CH$_2$—O— | | 2-CH$_3$-4-Br | SCH$_2$CH$_2$OCH$_3$ |
| —S—CH$_2$CH$_2$S— | | 2-CH$_3$-4-Br | OC$_2$H$_5$ |
| CH$_3$O | H | 3,5-Cl$_2$ | OC$_2$H$_5$ |
| CH$_3$O | H | 3,5-Br$_2$ | OC$_2$H$_5$ |
| CH$_3$O | H | 3-Br-5-Cl | O-n-C$_3$H$_7$ |
| CH$_3$O | H | 3-Br-5-F | O-t-C$_4$H$_9$ |
| C$_2$H$_5$OCO | CH$_3$ | 4-Cl | OCH$_3$ |
| CH$_3$S | CH$_3$ | 3,5-Cl$_2$ | OC$_2$H$_5$ |
| HO | H | 3,5-Cl$_2$ | O-n-C$_3$H$_7$ |
| CF$_3$O | H | 3,5-Cl$_2$ | OC$_2$H$_5$ |
| CF$_3$O | F | 3,5-Br$_2$ | OCH$_3$ |
| CH$_3$SO | CH$_3$ | 2-F-4-Br | O-n-C$_3$H$_7$ |
| CH$_3$SO$_2$ | H | 2-CH$_3$-4-Br | OC$_2$H$_5$ |
| CH$_3$SO$_2$ | CH$_3$ | 3,5-Cl$_2$ | OC$_2$H$_5$ |
| C=N— | H | 2-CH$_3$-4-Br | OC$_2$H$_5$ |
| CH$_3$S | H | 2-CH$_3$-4-Br | OC$_2$H$_5$ |

TABLE 4

Representative Malonic Acid Derivative Compounds

[Structure: cyclobutane ring with Y'9, Y'7, Y'10, Y'8 substituents, R'10-C(O)-C-C(O)-N(Y'6)-phenyl-Z'11]

| Y'7 | Y'8 | Y'9 | Y'10 | Y'6 | R'10=R''10Y'41 | Z'11 |
|---|---|---|---|---|---|---|
| H | H | H | H | H | OH | 2-C$_2$H$_5$-4-Cl |
| H | H | H | H | H | OCH$_3$ | 2-C$_2$H$_5$-4-Cl |
| H | H | H | H | H | OH | 2-C$_2$H$_5$-4-Br |
| H | H | H | H | H | OC$_2$H$_5$ | 2-C$_2$H$_5$-4-Br |
| H | H | H | H | CH$_3$ | OH | 4-Cl |
| H | H | H | H | CH$_3$ | ONa | 4-Br |
| H | H | H | H | CH$_3$ | OH | 3,4-Cl$_2$ |
| H | H | H | H | CH$_3$ | OC$_2$H$_5$ | 2-Cl-4-Br |
| H | H | H | H | CH$_3$ | OH | 2-F-4-Br |
| H | H | H | H | H | OH | 3-F-4-Cl |
| H | H | H | H | H | OCH$_3$ | 3-F-4-Br |
| H | H | H | H | H | NH$_2$ | 2-CH$_3$-4-Br |
| H | H | H | H | H | ONH$_4$ | 2-CH$_3$-4-Br |
| H | H | CH$_3$ | H | H | OH | 2-F-4-Cl |
| Cl | Cl | CH$_3$ | H | H | OH | 2-CH$_3$-4-Cl |
| H | H | H | H | H | OH | 4-OCF$_3$ |
| H | H | H | H | H | OH | 2-Cl-4-OCF$_3$ |
| H | H | CH$_3$ | CH$_3$ | H | OC$_2$H$_5$ | 2,4-Cl$_2$ |
| CH$_3$ | CH$_3$ | CH$_3$ | CH$_3$ | H | ONa | 2-CH$_3$-4-Br |
| CH$_3$ | H | H | H | H | OH | 4-Cl |
| CH$_3$ | CH$_3$ | H | H | H | ONH$_4$ | 2-C$_2$H$_5$-4-Cl |
| Cl | H | H | H | H | OH | 2-F-4-Br |
| Cl | Cl | H | H | H | OCH$_3$ | 2,4-Br$_2$ |
| Cl | Cl | CH$_3$ | CH$_3$ | H | OH | 4-Cl |
| H | H | H | H | H | OH | 2-CH$_3$O-4,5-Cl$_2$ |
| H | H | H | H | H | OH | 2-CH$_3$O-3,5-Cl$_2$ |
| H | H | H | H | H | ONa | 2-CF$_3$-4-Cl |
| H | H | H | H | H | OCH$_3$ | 2-CF$_3$O-4-CF$_3$ |
| H | H | H | H | H | OK | 2-F-4-I |
| H | H | H | H | H | OH | 3-Br-4-Cl |
| C$_2$H$_5$ | H | H | H | H | OH | 2-CH$_3$-4-Br |
| H | H | CH$_3$ | CH$_3$ | H | OC$_2$H$_5$ | 2,4-Cl$_2$ |
| CH$_3$ | CH$_3$ | CH$_3$ | CH$_3$ | H | ONa | 2,CH$_3$-4-Br |
| Cl | Cl | CH$_3$ | CH$_3$ | H | OH | 4 Cl |
| F | F | H | H | H | OH | 4-CF$_3$ |
| H | H | F | F | H | OC$_2$H$_5$ | 2-CH$_3$-4-Br |

TABLE 5

Representative Malonic Acid Derivative Compounds

[Structure: cyclopentane ring with Y'14, Y'13, Y'15, Y'11, Y'16, Y'12 substituents, R'11-C(O)-C-C(O)-NH-phenyl-Z'12]

| Y'11 | Y'12 | Y'13 | Y'14 | Y'15 | Y'16 | R'11 | Z'12 |
|---|---|---|---|---|---|---|---|
| H | H | H | H | H | H | OC$_2$H$_5$ | 2,4-Cl$_2$ |
| H | H | H | H | H | H | OH | 2,4-Cl$_2$ |
| H | H | H | H | H | H | OC$_2$H$_5$ | 3,4-Cl$_2$ |
| H | H | H | H | H | H | OH | 3,4-Cl$_2$ |
| H | H | H | H | H | H | OC$_2$H$_5$ | 4-Cl |
| H | H | H | H | H | H | OH | 4-Cl |
| H | H | H | H | H | H | OCH$_3$ | 2-F-4-Cl |
| H | H | H | H | H | H | ONa | 2-F-4-Br |
| H | H | H | H | H | H | ONH$_4$ | 2-Cl-4-Br |
| H | H | H | H | H | H | OCH$_3$ | 2-Br-4-Cl |
| H | H | H | H | H | H | OK | 4-Br |
| H | H | H | H | H | H | OH | 2-CF$_3$-4-Br |
| CH$_3$ | CH$_3$ | H | H | H | H | OH | 2-CH$_3$-4-Br |
| H | H | CH$_3$ | CH$_3$ | H | H | OCH$_3$ | 4-Cl |
| CH$_3$ | H | CH$_3$ | H | H | H | ONa | 4-Br |
| CH$_3$ | CH$_3$ | CH$_3$ | CH$_3$ | H | H | NH$_2$ | 2,4-Br$_2$ |
| Cl | Cl | H | H | H | H | OH | 3,4-Cl$_2$ |
| H | H | Cl | Cl | H | H | OCH$_3$ | 2-C$_2$H$_5$-4-Br |
| CH$_3$ | H | H | H | Cl | Cl | ONH$_4$ | 4-Cl |
| Cl | H | H | H | Cl | H | OC$_2$H$_5$ | 3-F-4-Cl |
| Cl | Cl | CH$_3$ | H | Cl | H | OH | 3,4-Br$_2$ |
| CH$_3$ | Cl | H | H | H | H | OCH$_3$ | 2-CH$_3$-4-Cl |
| CH$_3$ | CH$_3$ | CH$_3$ | Cl | H | H | ONa | 3,4-Cl$_2$ |
| H | H | H | H | H | H | OH | 3-Br-4-Cl |
| H | H | H | H | H | H | ONa | 2-CH$_3$O-4,5-Cl$_2$ |
| H | H | H | H | H | H | OH | 2-CH$_3$O-3,5-Cl$_2$ |
| H | H | H | H | H | H | OCH$_3$ | 2-CF$_3$-4-Br |
| H | H | H | H | H | H | OK | 2-CF$_3$O-4-Cl |
| H | H | H | H | H | H | OH | 2-C$_2$H$_5$-4-I |

TABLE 6

Representative Malonic Acid Derivative Compounds

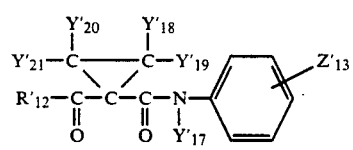

| Y'18 | Y'19 | Y'20 | Y'21 | Y'17 | Z'13 | R'12=R''12Y'43 |
|---|---|---|---|---|---|---|
| H | H | H | H | H | 2-CH$_3$-4-Br | OCH$_2$CH$_2$OCH$_3$ |
| H | H | H | H | H | 2-CH$_3$-4-Br | OCH$_2$CH$_2$OH |
| H | H | H | H | H | 4-Cl | OCH$_2$CH$_2$SO$_2$CH$_3$ |
| H | H | H | H | H | 2-Cl-4-Br | OCH$_2$COCH$_3$ |
| H | H | H | H | H | 2-F-4-Br | OCH(CH$_3$)C≡N |
| H | H | H | H | H | 2-CH$_3$-4-Br | OCH$_2$CH$_2$SO$_2$CH$_2$OH |
| H | H | H | H | CH$_3$ | 3,4-Br$_2$ | OCH$_2$CH$_2$OH |
| CH$_3$ | CH$_3$ | CH$_3$ | H | H | 4-Br | O—N=CHCH$_3$ |
| Cl | Cl | CH$_3$ | H | H | 2,4-Cl$_2$ | OCH$_2$CONH$_2$ |
| H | H | CH$_3$ | CH$_3$ | CH$_3$ | 4-Cl | SCH$_3$ |
| CH$_3$ | H | CH$_3$ | CH$_3$ | H | 3-F-4-Cl | SCH$_2$CO$_2$CH$_3$ |
| Cl | Cl | CH$_3$ | CH$_3$ | H | 2-CF$_3$-4-Br | OCH$_2$CH$_2$OH |
| H | H | H | H | H | 2,4-Br$_2$ | OCH$_2$CH$_2$OCH$_2$CH$_2$OH |
| H | H | H | H | H | 3-Br-4-Cl | SC$_6$H$_5$ |
| H | H | H | H | H | 2-CF$_3$O-4-F | OCH$_2$CH$_2$OH |
| H | H | H | H | H | 2-CF$_3$-4-I | OCH$_2$COCH$_3$ |

TABLE 7

Representative Malonic Acid Derivative Compounds

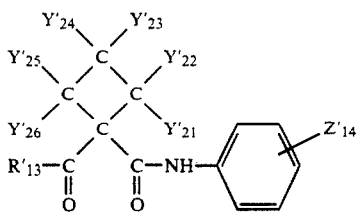

| Y'21 | Y'22 | Y'23 | Y'24 | Y'25 | Y'26 | Z'14 | R'13 |
|---|---|---|---|---|---|---|---|
| H | H | H | H | H | H | 2-CH3-4-Br | OCH2CH2OCH3 |
| H | H | H | H | H | H | 2-CH3-4-Br | OCH2CH2SO2CH2CH2OH |
| H | H | H | H | H | H | 2,4-Br2 | OCH2CH2OCH2CH2OH |
| H | H | H | H | H | H | 3,4-Cl2 | SCH2CO2C2H5 |
| CH3 | CH3 | H | H | H | H | 2-F-4-Br | O—N= CHCH3 |
| H | H | CH3 | CH3 | H | H | 2-CH3-4-Cl | O—N=C(CH3)(SCH3) |
| Cl | Cl | H | H | H | H | 2-CF3-4-Br | OCH2CONH2 |
| H | H | Cl | Cl | H | H | 4-Cl | OCH2C≡N |
| H | H | H | H | Cl | Cl | 4-Br | SCH2P(OC2H5)2 (=O) |
| CH3 | Cl | H | H | H | H | 3-F-4-Cl | OCH2CH2NHCO2C2H5 |
| CH3 | H | Cl | Cl | H | H | 2,4-Cl2 | OCH2COCH3 |
| H | H | H | H | H | H | 2-CF3-4-CF3O | OCH2CH2CONH2 |
| H | H | H | H | H | H | 2-C2H5-4-I | OCH2CH2OH |
| H | H | H | H | H | H | 2-Br-4-CF3 | SCH2CH2OCH3 |

TABLE 8

Representative Malonic Acid Derivative Compounds

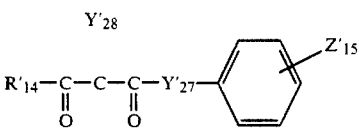

| Y'28 | Y'27 | R'14 | Z'15 |
|---|---|---|---|
| —CH2CH2— | S | OH | 2,4-Cl2 |
| —CH2CH2— | O | OH | 2,4-Br2 |
| —CH2CH2— | O | OH | 2-Br-4-C6H5O— |
| —CH2CH2— | S | OCH3 | 3,5-Cl2 |
| —CH2CH2— | S | NH2 | 2-F-4-Cl |
| —CH(CH3)CH2— | O | O⁻Na⁺ | 2,5-Cl2 |
| —CH2CCl2— | S | NHCH3 | 2-CH3O-4,5-Cl2 |
| —CH2C(CH3)2— | O | NHCH2CH2OH | 4(4-ClC6H4O)— |
| —CH2CH2CH2— | S | OC2H5 | 2,4-Cl2 |
| —CH2CH2CH2— | S | OCH3 | 3,5-Br2 |
| —CH2CH2CH2— | O | NH2 | 2-Cl-4-Br |
| —CH2CH2CH2— | O | OCH2CH2OH | 2-CH3-4,5-Br2 |
| —CH2CH2CH2— | S | OCH3 | 2,4,5-Cl3 |
| —CH2CH2CH2— | S | O-n-C3H7 | 2-Br-5-C6H5O |
| —CH2CH2CH2CH2— | O | OC2H5 | 3,4-Cl2 |
| —CH2CH2CH2CH2— | S | OC2H5 | 2,4-Cl2 |
| —CH2CH2CH2CH2— | O | NH2 | 2-Br-4-CN |
| —CH2CH2CH2CH2— | O | OC2H5 | 4-C6H5O |
| —CH2CH2CH2CH2— | S | OH | 3,5-Cl2 |
| —CH2CH2CH2CH2— | O | NHCH2CH2OCH3 | 4-Cl |
| —CH2CH2— | O | SC6H5 | 3,4-Br2 |
| —CH2CH2— | O | SCH2CH2OH | 3-Br-5-Cl |
| —CH2CH2CH2— | O | SCH3 | 2-CF3-4-Br |
| —CH2CH2— | S | OCH3 | 3,5-(CF3)2 |

TABLE 9

Representative Malonic Acid Derivative Compounds (cont.)

| Y'30 | Y'31 | Y'29 | R'15 | Z'16 |
|---|---|---|---|---|
| H | H | O | OC2H5 | 3,5-Cl2 |
| H | H | S | OC2H5 | 2,4-Cl2 |
| H | H | S | O-n-C3H7 | 2,4-Br2 |
| H | H | O | OCH3 | 2-Cl-4-C6H5O— |
| CH3 | CH3 | O | OH | 4 C6H5O— |
| CH3 | Br | S | OCH3 | 2-Cl-4-Br |
| N≡C— | H | O | OC2H5 | 3,5-Br2 |
| N≡C— | CH3 | S | OC2H5 | 2,4-Cl |
| C2H5 | H | O | NHCH3 | 2-F-4-Cl |
| CH3O— | H | O | NH2 | 2,4,5-Cl3 |
| CH3O | CH3O | S | OC2H5 | 2-Cl-4-Br |
| N≡C— | Br | O | OCH3 | 2,4-Cl2 |
| O2N | CH3 | S | SC6H5 | 4-Br |
| CH3O— | CH3 | O | SCH2CH2OC2H5 | 2-Br-4-CN |

TABLE 10

Representative Malonic Acid Derivative Compounds

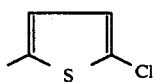

| Y'33 | Y'34 | Y'32 | R'16 | Z'17 |
|---|---|---|---|---|
| H | H | NH | $OC_2H_5$ | 2-$CH_3$-4-Br |
| H | H | NH | $OC_2H_5$ | 2-F-4-Br |
| H | H | NH | $OC_2H_5$ | 2-F-4-Cl |
| H | H | NH | $OC_2H_5$ | 3,5-$Cl_2$ |
| H | H | NH | OH | 3,4-$Br_2$ |
| H | H | NH | $OCH_3$ | 2,4,5-$Cl_3$ |
| $CH_3$ | H | NH | $OC_2H_5$ | ·2-$CH_3$-4-Br |
| $CH_3$ | H | NH | $OCH_3$ | 3,5-$Br_2$ |
| $CH_3$ | H | NH | $SCH_2CH_2OCH_3$ | 4-Cl |
| $CH_3$ | H | $N(CH_3)$ | $OCH_2CH_2OH$ | 3-F-4-Br |
| $CH_3$ | H | O | $NH_2$ | 3,4-$Cl_2$ |
| $CH_3$ | H | S | $OCH_3$ | 2,4-$Cl_2$ |
| $CH_3$ | H | NH | OH | 2-$CH_3$-4-Br-5-Cl |
| $CH_3$ | H | NH | $OC_2H_5$ | 2-$CH_3O$-4,5-$Cl_2$ |
| $CH_3$ | $CH_3$ | NH | $OC_2H_5$ | 4-Cl |
| $CH_3$ | $CH_3$ | NH | $OC_2H_5$ | 2,4-$Cl_2$ |
| $CH_3$ | $CH_3$ | NH | $OC_2H_5$ | 3,4-$Br_2$ |
| $CH_3$ | $CH_3$ | NH | $OC_2H_5$ | 3-Cl-5-Br |
| $CH_3$ | $CH_3$ | NH | OH | 3,5-$(CF_3)_2$ |
| $CH_3$ | $CH_3$ | NH | OH | 2-$CF_3$-4-Br |
| $CH_3$ | $CH_3$ | NH | $OCH_3$ | 3-$CF_3$-5-Cl |
| $CH_3$ | $CH_3$ | O | $OC_2H_5$ | 2-Cl-4-$C_6H_5O$ |
| $CH_3$ | $CH_3$ | S | $OCH_3$ | 2,4-$Cl_2$ |
| $CH_3$ | $CH_3$ | S | OH | 3,5-$Cl_2$ |
| H | H | O | $OCH_2CN$ | 3,4-$Br_2$ |
| H | H | S | $OCH_2CH_2OCH_3$ | 2-Br-4-CN |
| $C_2H_5$ | H | NH | $OC_2H_5$ | 2-$CH_3$-4-Br |
| $C_2H_5$ | H | NH | $OCH_3$ | 2,4-$Br_2$ |
| Cl | Cl | NH | $OC_2H_5$ | 2-$CH_3$-4-Br |
| Br | Br | NH | $OC_2H_5$ | 4-Cl |
| $CH_3S-$ | $CH_3S-$ | NH | $OCH_3$ | 3,4-$Cl_2$ |
| $CH_3O$ | $CH_3O$ | NH | $OCH_3$ | 2-F-4-Cl |
| $CH_3CCl_2-$ | H | NH | $S$-$n$-$C_3H_7$ | 3,5-$Br_2$ |
| $-S-CH_2CH_2-S-$ | | NH | $OCH_3$ | 3,5-$Cl_2$ |
| $-S-CH_2CH_2-NH-$ | | NH | $SC_6H_5$ | 2,4-$Br_2$ |
| $C_2H_5$ | H | NH | $OCH_3$ | 2,4-$Br_2$ |
| Cl | Cl | NH | $OC2H_5$ | 2-$CH_3$-4-Br |

TABLE 11

Representative Malonic Acid Derivative Compounds

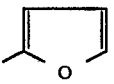

| Y36' | Y37' | Y35' | R18' | R17' |
|---|---|---|---|---|
| H | H | NH | $OC_2H_5$ | 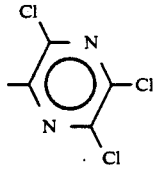 |
| H | H | NH | $OC_2H_5$ | |
| H | H | NH | $O$-$n$-$C_3H_7$ | |

TABLE 11-continued

Representative Malonic Acid Derivative Compounds $$R_{18}'-\underset{\underset{O}{\|}}{C}-\underset{\underset{Y_{37}'}{|}}{\overset{Y_{36}'}{|}}-\underset{\underset{O}{\|}}{C}-Y_{35}'-R_{17}'$$

| $Y_{36}'$ | $Y_{37}'$ | $Y_{35}'$ | $R_{18}'$ | $R_{17}'$ |
|---|---|---|---|---|
| H | H | NH | $OCH_3$ | pyridazine-Cl |
| H | H | NH | $OC_2H_5$ | triazine-Cl,Cl |
| $CH_3$ | H | NH | $O$-n-$C_3H_7$ | pyridine-CN,Cl |
| $C_2H_5$ | $C_2H_5$ | O | $SC_6H_5$ | pyridine-Cl,Cl |
| $CH_3$ | Br | S | $NHC_2H_5$ | pyridine-Cl,Cl |
| $N\equiv C$ | $CH_3$ | S | $SCH_2CH_2OCH_3$ | pyridine-$OC_6H_5$ |
| $N\equiv C$ | Cl | $N(CH_3)$ | $OCH_2CH=CH_2$ | pyridazine-O-phenyl-Cl |

It is appreciated that the particular compounds listed in Tables 1 through 11 hereinabove are illustrative of malonic acid derivative compounds which a can be used in the synergistic plant growth regulator compositions of this invention. The synergistic plant growth regulator compositions of this invention are not to be construed as being limited only to these particular compounds; but rather, the compositions of this invention include those malonic acid derivative compounds encompassed within formula 1 hereinabove.

The novel malonic acid derivative compounds of this invention can be depicted by the following formulae:

$$R_6-Y_{12}-\underset{\underset{O}{\|}}{C}-CH_2-\underset{\underset{O}{\|}}{C}-Y_{11}-\text{phenyl}(Z_1)_n \quad (i)$$

wherein:

$Z_1$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy, alkenyl or $—CH=CHCH=CH—$;

n is a value of from 0 to 5;

$Y_{11}$ is O, S or $NR_7$ wherein $R_7$ is hydrogen or alkyl;

$Y_{12}$ is O, S, NH or N (alkyl); and $R_6$ is ammonium, alkylammonium, polyalkylammonium, hydroxyalkylammonium, poly(hydroxyalkyl)ammonium, an alkali metal or alkaline earth metal or substituted or unsubstituted hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryloxy-alkyl, alkylsulfonylalkyl, alkylsulfinylalkyl, acylalklyl, aroylalkl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonloxyalkyl, alkoxycarbonylthioalkyl, aminosulfonylalkyl, alkylaminosulfonylalkyl or dialkylaminosulfonylalkyl;

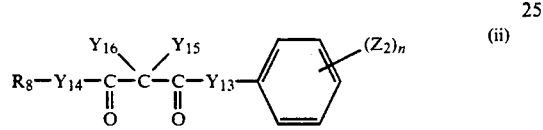

wherein:

$Z_2$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy, alkenyl or —CH=CHCH=CH—;

n is a value of from 0 to 5;

$Y_{13}$ is O, S or $NR_9$ wherein $R_9$ is hydrogen or alkyl;

$Y_{14}$ is O, S, NH or N (alkyl);

$Y_{15}$ and $Y_{16}$ are independently hydrogen, alkyl, halogen, alkoxy, alkylthio, alkenyl, alkynyl, cycloalkyl, isocyano, alkylsulfonyl, alkylsulfinyl, alkylamino, dialkylamino, alkoxycarbonyl, polyhaloalkoxy, hydroxy, cyano, nitro, formyl, amino, alkylcarbonyl, dialkoxyalkyl, alkylcarbonylamino, formylamino, hydroxyalkyl, haloalkyl or polyhaloalkyl, $Y_{15}$ and $Y_{16}$ may be linked together to form a substituted or unsubstituted heterocyclic ring system selected from a monocyclic aromatic or nonaromatic ring system, a bicyclic aromatic or nonaromatic ring system, a polycyclic aromatic or nonaromatic ring system and a bridged ring system which may be saturated or unsaturated; and $R_8$ is hydrogen, ammonium, alkylammonium, polyalkylammonium, hydroxyalkylammonium, poly(hydroxyalkyl)ammonium, an alkali metal or alkaline earth metal or substituted or unsubstituted alkyl, hydroxyalkyl, alkoxyalkyl, alkoxycarbonylakyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylaklyl, aroylalkyl, dialkoxyphosphinylalkyl, diaryloxyphosphinylalkyl, hydroxyalkylthioalkyl, hydroxyalkylsulfonylalkyl, alkoxyalklylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonyloxy-alkyl, alkoxycarbonylthioalkyl, aminosulfonylalkyl, alkylaminosulfonylalkyl or dialkylaminosulfonylalkyl;

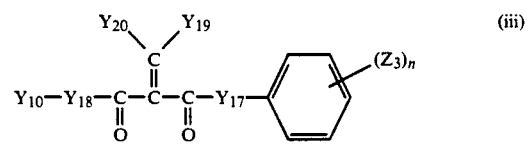

wherein:

$Z_3$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl aroyl, alkoxycarbonyl, alkoxycarbonylalkyl, acylamino, sulfonylamino, alkylsulfonylamino, acyloxy, alkenyl or —CH=CHCH=CH—;

n is a value of from 0 to 5;

$Y_{17}$ is O, S or $NR_{11}$ wherein $R_{11}$ is hydrogen or alkyl;

$Y_{18}$ is O or S;

$Y_{19}$ and $Y_{20}$ are independently hydrogen, alkyl, alkoxy, alkylthio, halogen, haloalkyl or polyhaloalkyl; or $Y_{19}$ and $Y_{20}$ may be linked together to form a substituted or unsubstituted, carboxyclic or heterocyclic ring system selected from a monocyclic aromatic or nonaromatic ring system, a bicyclic aromatic or nonaromatic ring system, a polycyclic aromatic or nonaromatic rig system and a bridged ring system which may be saturated or unsaturated; and $R_{10}$ is hydrogen, ammonium, alkylammonium polyalkylammonium, hydroxyalkylammonium, poly(hydroxyalkyl)ammonium, an alkali metal or alkaline earth metal or substituted or unsubstituted alkyl, hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryoxyalkyl, alkylsulfonyalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonyloxyalkyl, alkoxycarbonylthioalkyl, aminosulfonylalkyl, alkylaminosulfonylalkyl or dialkylaminosulfonylalkyl; and

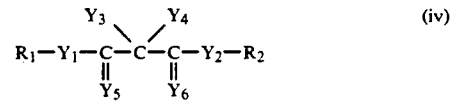

wherein:
R$_1$ and R$_2$ are independently a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated; or R$_1$ and R$_2$ are independently hydrogen or derivative salts, or a substituted heteroatom or substituted carbon atom, or a substituted or unsubstituted, branches or straight chain containing two or more carbon atoms or heteroatoms in any combination;

Y$_1$ and Y$_2$ are independently a substituted or unsubstituted heteroatom;

Y$_3$ and Y$_4$ are linked together to form a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated; and Y$_5$ and Y$_6$ are independently oxygen or sulfur;

in which the permissible substituents (Z) for formulae (i) through (iv) above are the same or different and are one or more hydrogen, halogen, aklylcarbonyl, alkylcarbonylalkyl, formyl, alkoxycarbonylalkyl, alkoxycarbonylalkylthio, polyhaloalkenylthio, thiocyano, propargylthio, hydroxyimino, alkoxyimino, trialkyl-silyloxy, aryldialkylsilyloxy, triarylsilyloxy, form-amidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, arylsulfonyl, haloalkylsulfinyl, haloalkylsulfonyl, haloalkenyloxy, haloalkynyloxy, haloalkynylthio, haloalkenylsulfonyl, polyhaloalkenylsulfonyl, isocyano, aryloxysulfonyl, propargyloxy, aroyl, haloaycl, polyhaloacyl, aryloxycarbonyl, aminosulfonyl, alkylaminosulfonyl, dialkylaminosulfonyl, arylaminosulfonyl, carboxyalkoxy, carboxyalkylthio, alkoxycarbonylakoxy, acyloxy, haloacycloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloacylamino, alkoxycarbonyloxy, arylsulfonylamino, aminocarbonyloxy, cyanato, isocyanato, isothiocyano, cycloalkylamino, trialkylammonium, arylamino, aryl(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkyloxosulfonium, —X, =X, —X=R$_3$, =X—R$_3$,

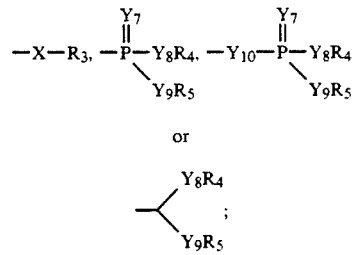

or wherein:
X is a covalent single bond or double bond, a substituted or unsubstituted heteroatom or substituted carbon atom, or a substituted or unsubstituted, branched or straight chain containing two or more carbon atoms or heteroatoms in any combination;

R$_3$ is a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated; or R$_3$ is a substituted heteroatom or substituted carbon atom, or a substituted or unsubstituted, branched or straight chain containing two or more carbon atoms or heteroatoms in any combination;

Y$_7$ and Y$_{10}$ are independently oxygen or sulfur;

Y$_8$ and Y$_9$ are independently oxygen, sulfur, amino or a covalent single bond; and R$_4$ and R$_5$ are independently hydrogen or substituted or unsubstituted alkyl, alkenyl, alkynyl, polyhaloalkyl, phenyl or benzyl; in which the permissible substituents (Z) are the same or different and are one or more hydrogen, halogen, alkylcarbonyl, alkylcarbonylalkyl, formyl, alkoxycarbonylakyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, formamidino, alkylsulfamido, dialkylsulfamido, alkoxysulfonyl, polyhaloalkoxysulfonyl, hydroxy, amino, azido, azo, aminocarbonyl, alkylaminocarbonyl, hydrazino, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkylenyloxy, polyhaloalkynyl, polyhaloalkynyloxy, polyfluoroalkanol, cyanoalkylamino, semicarbazonomethyl, alkoxycarbonylhydra-zonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, haloalkyl, haloalkenyl, haloalkynyl, alkoxyalkyl, aryloxy, aralkoxy, arylthio, aralkylthio, alkylthioalkyl, arylthioalkyl, arylsulfinyl, aryl-sulfonyl, haloalkylsulfinyl, haloalkylsulfonyl, haloalkenyloxy, haloalkynyloxy, haloalkynylthio, haloalkenylsulfonyl, polyhaloalkyenylsulfonyl, isocyano, aryloxysulfonyl, propargyloxy, aroyl, haloacyl, polyhaloayl, aryloxycarbonyl, aminosulfonyl, alkylaminosulfonyl, dialkylaminosulfonyl, arylaminosulfonyl, carboxyalkoxy, carboxyalkylthio, alkoxycarbonylalkoxy, acyloxy, haloacyloxy, polyhaloacyloxy, aroyloxy, alkylsulfonyloxy, alkenylsulfonyloxy, arylsulfonyloxy, haloalkylsulfonyloxy, polyhaloalkylsulfonyloxy, aroylamino, haloayclamino, alkoxycarbonyloxy, arylsulfonylamino, aminocarbonyloxy, cyanato, isocyanato, isothiocyano, cycloalkylamino, trialkylammonium, arylamino, aryl-(alkyl)amino, aralkylamino, alkoxyalkylphosphinyl, alkoxyalkylphosphinothioyl, alkylhydroxyphosphinyl, dialkoxyphosphino, hydroxyamino, alkoxyamino, aryloxyamino, aryloxyimino, oxo, thiono, diazo, alkylidene, alkylimino, hydrazono, semicarbazono, dialkylsulfonium, dialkyloxosulfonium, —X, =X, —X=R$_3$, =X—R$_3$,

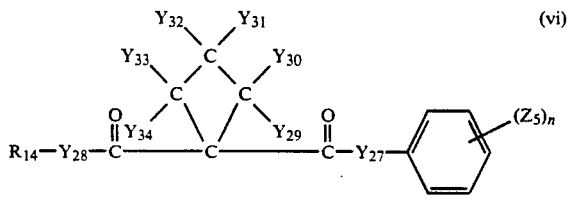

or

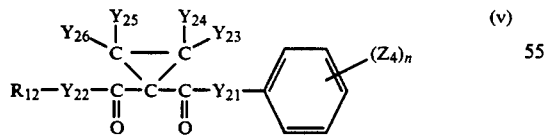

Novel malonic acid derivative compounds within the scope of formula (iv) above can be depicted by the following formulae;

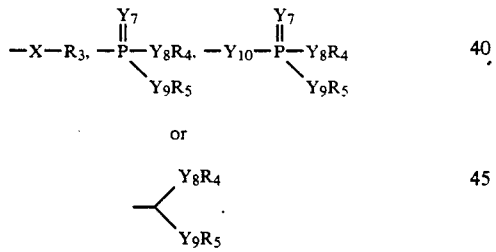

wherein:
Z$_4$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonyl-amino, acyloxy, alkenyl or —CH=CHCH=CH—;

n is a value of from 0 to 5;
Y$_{21}$ is O, S or NR$_{13}$ wherein R$_{13}$ is hydrogen or alkyl;
Y$_{22}$ is O, S, NH or N (alkyl);
Y$_{23}$, Y$_{24}$, Y$_{25}$ and Y$_{26}$ are independently hydrogen, alkyl or halogen; and
R$_{12}$ is hydrogen, ammonium, alkylammonium, polyalkylammonium, hydroxyalkylammonium, poly(hydroxyalkyl)ammonium, an alkali metal or alkaline earth metal or substituted or unsubstituted alkyl, hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylalkyl, aroylalkyl, dialkoxyphos-phinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalklyene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, alkoxycarbonylthioalkyl, aminosulfonylalkyl, alkylaminosulfonylalkyl or dialkylaminosulfonylalkyl;

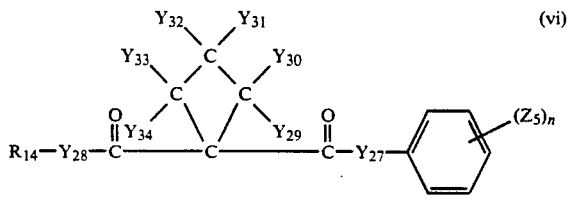

wherein:
Z$_5$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkyl,-sulfonylamino, acyloxy, alkenyl or —CH=CHCH=CH—;
n is a value of from 0 to 5;
Y$_{27}$ is O, S or NR$_{15}$ wherein R$_{15}$ is hydrogen or alkyl;
Y$_{28}$ is O S, NH or N (alkyl);
Y$_{29}$, Y$_{30}$, Y$_{31}$, Y$_{32}$, Y$_{33}$ and Y$_3$ are independently hydrogen, alkyl or halogen; and
R$_{14}$ is hydrogen, ammonium, alkylammonium, polyalkylammonium, hydroxyalkylammonium, poly(hydroxyalkyl)ammonium, an alkali metal or alkaline earth metal or substituted or unsubstituted alkyl, hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonyloxyalkyl, alkoxycarbonylthioalkyl, aminosulfonylalkyl, alkylaminosulfonylalkyl or dialklaminosulfonylalkyl;

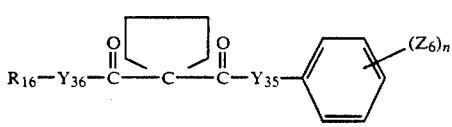
(vii)

wherein:

$Z_6$ is independently substituted or unsubstituted halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonyl-amino, acyloxy, alkenyl or —CH=CHCH=CH—;

n is a value of from 0 to 5;

$Y_{35}$ is O, S or $NR_{17}$ wherein $R_{17}$ is hydrogen or alkyl;

$Y_{36}$ is O or S; and $R_{16}$ is hydrogen, ammonium, alkylammonium, polyalkylammonium, hydroxyalkylammonium, poly(hydroxyalkyl)ammonium, an alkali metal or alkaline earth metal or substituted or unsubstituted alkyl, hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonyloxyalkyl, alkoxycarbonylthioalkyl, amino-sulfonylalkyl, alkylaminosulfonylalkyl or dialkylaminosulfonylalkyl; in which the permissible substituents for formulae (v) through (vii) are as described for Z above for formulae (i) through (iv).

More specifically, the cyclopropanomalonic acid derivative compounds of formula (V) above are alternatively depicted by the corresponding generic formulae for representative compounds contained in Tables 4 and 6 above as follows:

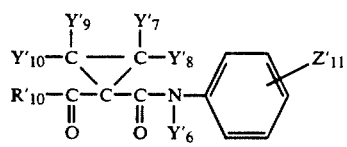
(from Table 4)

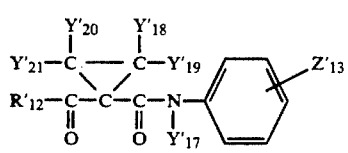
(from Table 6)

wherein:

$Z'_{11}$ and $Z'_{13}$ have the same definitions as $(Z_4)_n$ in formula (V);

$Y'_6$ and $Y'_{17}$ have the same definitions are $R_{13}$ in formula (V);

$Y'_7$ to $Y'_{10}$ and $Y'_{18}$ to $Y'_{21}$ have the same definitions as $Y_{23}$ to $Y_{25}$ in formula (V); and $Y'_{10}$ is $R''_{10}Y'_{41}$ and $R'_{12}$ is $R''_{12}Y'_{43}$, in which $Y'_{41}$ and $Y'_{43}$ are O, S, NH or N(alkyl) and $R''_{10}$ and $R''_{12}$ are hydrogen, a derivative salt or an unsubstituted or substituted lower alkyl; and more specifically, $R''_{10}$ and $R''_{12}$ have the same definitions as $R_{12}$ in formula (V).

The malonic acid derivative compounds encompassed within formula 1 and the intermediate compounds used in the preparation thereof can be prepared by conventional methods known in the art and many may be available from various supplies. The novel malonic acid derivative compounds of formulae (i) through (Vii) above which may used in the method of this invention may be prepared by reacting appropriate starting ingredients in accordance with conventional procedures described in the art as illustrated below.

The novel malonic acid derivative compounds of formula (i) can be prepared by the following general reaction scheme:

Scheme I

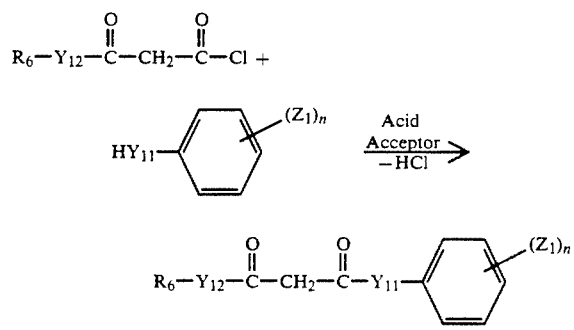

wherein $Z_1$, n, $Y_{11}$, $Y_{12}$ and $R_6$ are as defined hereinabove. Reactions of this general type for preparing malonic acid derivative compounds of formula (i) including process conditions are described for example by Richter, G. H., Textbook of Organic Chemistry, Third Edition, John Wiley and Sons, New York, p. 486. In the Schotten-Baumann procedure described therein, cold aqueous sodium hydroxide is illustrated as the acid acceptor.

The novel malonic acid derivative compounds of formula (ii) can be prepared by the following general reaction scheme:

Scheme II

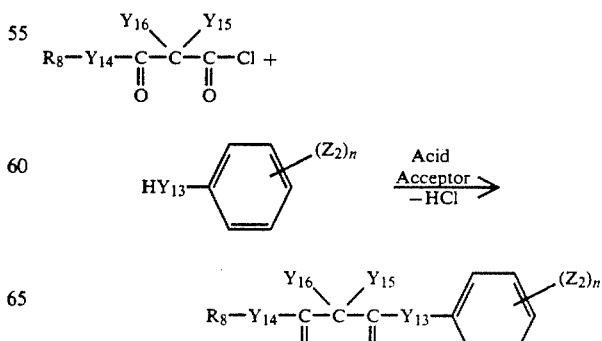

wherein $Z_2$, n, $Y_{13}$, $Y_{14}$, $Y_{15}$, $Y_{16}$ and $R_8$ are as defined hereinabove. Reactions of this general type for preparing malonic acid derivative compounds of formula (ii) including process conditions are described for example by Richter, G. H., supra, according to the known Schotten-Baumann procedure.

The novel malonic acid derivative compounds of formula (iii) can be prepared by the following general reaction scheme:

Scheme III

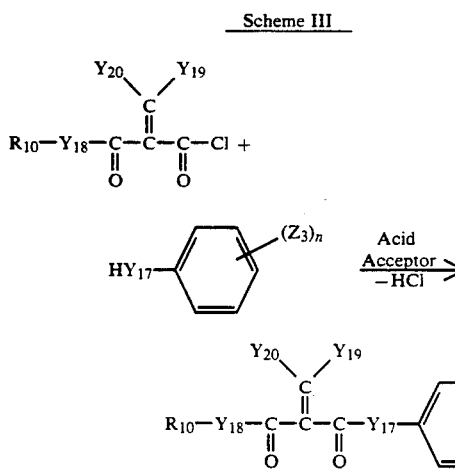

wherein $Z_3$, n, $Y_{17}$, $Y_{18}$, $Y_{19}$, $Y_{20}$ and $R_{10}$ are as defined hereinabove. Reactions of this general type for preparing malonic acid derivative compounds of formula (iii) including process conditions are described for example by Richter, G. H., supra, according to the known Schotten-Baumann procedure.

The novel malonic acid derivative compounds of formula (iv) can be prepared by the following general reaction scheme:

Scheme IV

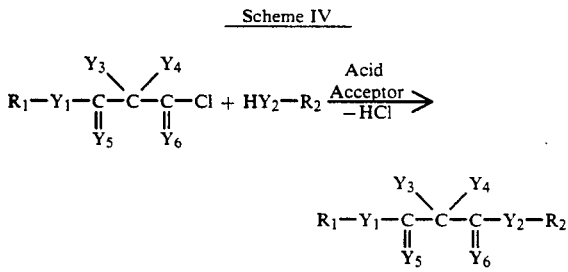

wherein $R_1$, $R_2$, $Y_1$, $Y_2$, $Y_3$, $Y_4$, $Y_5$ and $Y_6$ are as defined hereinabove. Reactions of this general type for preparing malonic acid derivative compounds of formula (iv) including process conditions are described for example by Richter, G. H., supra, according to the known Schotten-Baumann procedure.

The novel malonic acid derivative compounds of formula (v) can be prepared by the following general reaction scheme:

Scheme V

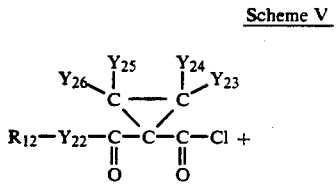

-continued
Scheme V

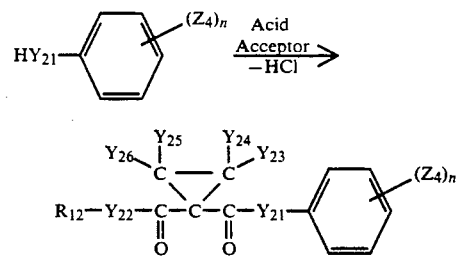

wherein $Z_4$, n, $Y_{21}$, $Y_{22}$, $Y_{23}$, $Y_{24}$, $Y_{25}$, $Y_{26}$ and $R_{12}$ are as defined hereinabove. Reactions of this general type for preparing malonic acid derivative compounds of formula (v) including process conditions are described for example by Richter, G. H., supra, according to the known Schotten-Baumann procedure.

The novel malonic acid derivative compounds of formula (vi) can be prepared by the following general reaction scheme:

Scheme VI

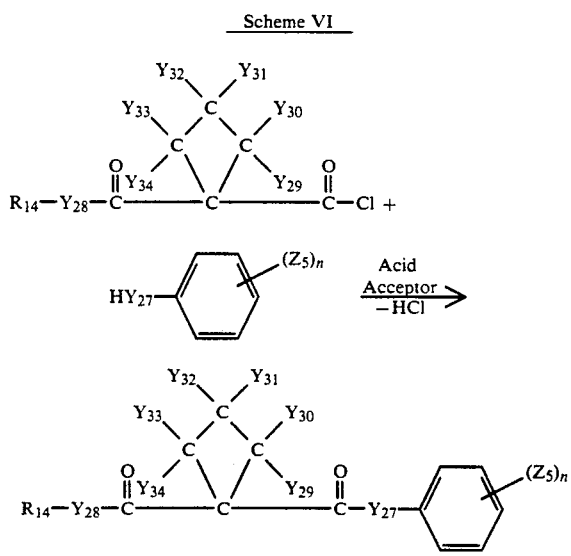

wherein $Z_5$, n, $Y_{27}$, $Y_{28}$, $Y_{29}$, $Y_{30}$, $Y_{31}$, $Y_{32}$, $Y_{33}$, $Y_{34}$ and $R_{14}$ are as defined hereinabove. Reactions of this general type for preparing malonic acid derivative compounds of formula (vi) including process conditions are described for example by Richter, G. H., supra, according to the known Schotten-Baumann procedure.

The novel malonic acid derivative compounds of formula (vii) can be prepared by the following general reaction scheme:

Scheme VII

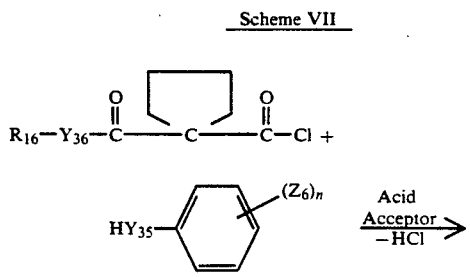

-continued
Scheme VII

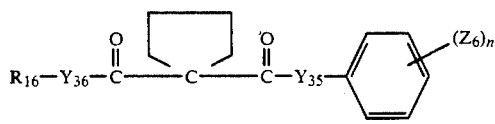

wherein $Z_{6n}$, $Y_{35}$, $Y_{36}$ and $R_{16}$ are as defined hereinabove. Reactions of this general type for preparing malonic acid derivative compounds of formula (vii) including process conditions are described for example by Richter, G. H., supra, according to the known Schotten-Baumann procedure.

The malonic acid derivative compounds encompassed with formula 1 and intermediate compounds used in the preparation thereof can be prepared by reacting appropriate starting ingredients in accordance with conventional methods known in the art, and many may be available from various suppliers. Novel malonic acid derivative compounds encompassed within formula 1 which can be used in the synergistic plant growth regulator compositions of this invention are described in copending U.S. Pat. application Ser. No. 06/846,435, filed Mar. 31, 1986, now abandoned, and also U.S. Pat. application Ser. No. 06/846,670 filed Mar. 31, 1986, now abandoned, both of which are incorporated herein by reference. These novel malonic acid derivative compounds can be prepared by reacting appropriate starting ingredients in accordance with conventional methods known in the art.

Illustrative procedures which can be employed in preparing malonic acid derivative compounds encompassed within formula 1 and intermediate compounds use din the preparation thereof are described, for example, in the following: Richter, G. H., Textbook of Organic Chemistry, Third Edition, John Wiley and Sons, New York, p. 486; Breslow, D. S. et al., Jour. Amer. Chem. Soc. 66, 1286-1288 (1944); Svendsen, A. and Boll., P. M., Journ. Org. Chem. 40, 1927-193 (1975); Sen, A. K. and Sengupta. P., J. Ind. Chem. Soc. 46, (9), 857-859 (1969); Thiers, R. and Van Dormael, A., Bull. Soc. Chim. Belg. 61, 245-252 (1952); Brown, R. F. C., Austral. Jour. Of Chem. 8, 121-124 (1955); U.S. Pat. No. 3,951,996; United Kingdom Patent 1,374,900; Chiriac, C. I., Revue Romaine de Chimie 25, (3), 403-405 (1980); Weiner, M., Org. Syn. Coll., Vol. II, 279-282 (1950). Sixth Printing, John Wiley & Sons, New York; Block, Jr., Paul, Orgn. Syn. Coll. Vol. V, 381-383 (1973), John Wiley and Sons, New York; Reliquet, F. et al., Phos. and Sulfur 24, 279-289 (1985); Palmer, C. S. and McWherter, P. W., Org. Syn. Coll. Vol. I, 245-246 (1951), Second Edition, John Wiley and Sons, New York; Staudinger, H. and Becker, H., Berichte 50, 1016-1024 (1917); Purrington, S. T. and Jones, W. A., J. Org. Chem. 48, 761-762 (9183); Kitazume, T. et al., Chem. Letters (1984) 1811-1814; Wolff, I. A. et al., Synthesis (1984), 732-734; Zambito, A. J. and Howe, E.E.., Org. Syn. Coll. Vol. V, 373-375 (173), John Wiley and Sons, New York; and Hartung, W. H. et al., Org. Syn. Coll. Vol. V, 376-378, John Wiley and Sons, New York.

Still other illustrating procedures which can be employed in preparing malonic acid derivative compounds encompassed within formula 1 and intermediate compounds used in the preparation thereof are described, for example, in the following: Rathke, M. W. and Cowan, P. J., J. Org. Chem. 50, 2622-2624 (1985); Fones, W. S., Org. Syn. Coll. Vol. IV, 293 (1963), John Wiley and Sons, New York; Gompper, R. and Topfl., W., Chem. Ber. 95, 2861-2870 (1962); Gompper, R. and Kunz, R., Chem. Ber. 99, 2900-2904 (1966); Ono, N. et al., J. Org. Chem. 50, 2807-2809 (1985); U.S. Pat. No. 4,154,952; Blanekship, C. and Paquette, L. A., Synth, Comm. 14, (11), 983-987 (1984); Baldwin, J. E. et al., Tet. Lett. 26, (4), 481-484 (1985); Kawabata, N. et al., Bull. Chem. Soc. Jpn. 55, (8), 2687-2688 (1982); Bodanszky, M. and Du Vignaud, V., J. Am. Chem. Soc. 81, 5688-5691 (1959); Neelakantan, S. et al., Tetrahederon 21, 3531-3536 (1965); U.S. Pat. No. 4,020,099; Japan Patent Application 148,726 (1979); Fuson, R. C., Advanced Organic Chemistry, p. 202 (1950), John wiley and Sons, New York; Duty, R. C., Anal. Chem. 49, (6), 743-746 (1977); Korner, G., Contradi, Atti acad. Lincei 22, I, 823-836 (C.A. 8, 73 (1914)); Schimelpfenig, C. W. ,J. Chem. Soc. Perk. Trans. I, 1977 (10), 1129-1131; Kim, Y. S. et al., Taehan Hwahak Hoechi 18, (4), 278-288 (1974); German Patent No. 2,449,285; U.S. Pat. No. 3,962,336; and U.S. Pat. No. 3,992,189.

A variety of ethylene response or ethylene-type response inducing agents can be used in the synergistic plant growth regulator compositions of this invention. Illustrative of an ethylene response or ethylene-type response inducing agent is a compound having the formula:

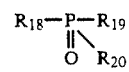

wherein:
$R_{18}$ is haloethyl; and
$R_{19}$ and $R_{20}$ are selected from:
1. A chlorine atom and a hydroxy group;
2. The group —$OR_{21}$ and the group —O—$CH_2R_{27}$ were each $R_{21}$ is one member of the group of unsubstituted aryl, substituted aryl and a heterocyclic group;
3. The group —$OR_{21}$ and the group —O—$CH_2R_{21}$ were each $R_{21}$ is a different member of the group of hydrogen, unsubstituted alkyl, substituted alkyl, unsubstituted cyclalkyl, substituted cycloalkyl, unsubstituted aryl, substituted aryl, a heterocyclic group, alkene and alkylne, provided that when one $R_{21}$ is selected from unsubstituted alkyl, substituted alkyl, alkene and alkyne, the other $R_{21}$ is selected from unsubstituted aryl, substituted aryl and a heterocyclic group;
4. Together $R_{19}$ and $R_{20}$ represent the group

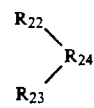

($R_{22}$ and $R_{23}$ are each connected to the phosphorus atom by a separate single bond) where one of $R_{22}$ and $R_{23}$ is —O— and the other is selected from the group of —O—; —$OCH_2$; —CO—O— and CONH; and $R_{24}$ represents a cyclic group selected from benzene, substituted benzene, a heterocyclic ring and a substituted heterocyclic ring;
5. One of $R_{19}$ and $R_{20}$ is —$OR_{25}$ and the other is

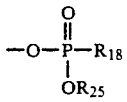

wherein each $R_{25}$ is the same or different and is selected from hydrogen, unsubstituted alkyl, substituted alkyl, unsubstituted aryl, substituted aryl and a heterocyclic group, and wherein $R_{18}$ is as defined hereinbefore;

in which the permissible substituents are as defined for Z hereinabove.

U.S. Pat. Nos. 3,879,188, 4,240,819, 4,352,869, 4,374,661 and 4,401,454 describe the phosphonic acid derivative compounds of formula 12 and the plant growth regulating properties thereof. These patents are incorporated herein by reference.

With reference to formula 12 compounds utilized in the synergistic plant growth regulator compositions of this invention, preferred groups for substituent $R_{18}$ are haloethyl, for example, 2-chloroethyl, 2-bromoethyl and 2-iodoethyl. Preferred half-esters of the phosphonic acid moiety include the 2-chloroethyl mon-ester and the o-hydroxyphenyl mono-ester. Preferred diesters include the diphenyl and the bis(2-oxo-1-pyrrolidinylmethyl)esters and as mixed esters, the 2-hydroxyphenyl ester with an alkyl or alkenyl or aryl radical, for example, ethyl, isopropyl, propynyl, butyl, octyl, hexadecyl or phenyl radicals. Aryl groups are preferably monocyclic, and bi- or polycyclic aryl groups may be used provided a group to render them soluble (e.g., a sulphonate group), is present thereon.

Preferred cyclic esters include those formed with pyrocatechol or mono- or polyhalopyrocatechol derivatives, for example, 4-chloropyrocatechol or tetrachloropyrocatechol; with salicyclic acid, with saligen; and with 2,3-pyridinediol. Another preferred derivative is the acid chloride.

The preferred phosphonic acid derivative to be used in the synergistic plant growth regulator compositions of this invention is 2-chloroethylphosphonic acid (ethephon) or its immediate derivatives.

As previously stated, the phosphonic acid compounds of formula 12 usable in the synergistic plant growth regulator compositions of this invention fall within the general formula:

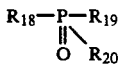

wherein $R_{18}$, $R_{19}$ and $R_{20}$ are as defined hereinabove.

Specific phosphonic acid derivative compounds usable in the synergistic compositions for regulating plant growth include:

1. The bis(acid chloride) of 2-chloroethylphosphonic acid.
2. The pyrocatechol cyclic ester of 2-chloroethylphosphonic acid.
3. The 4-chloropyrocatecol cyclic ester of 2-chloroethylphosphonic acid.
4. The mixed ethyl and 2-hydroxyphenyl diester of 2-chloroethylphosphonic acid.
5. The mixed butyl and 2-hydroxyphenyl diester of 2-choroethylphosphonic acid.
6. The mixed propynyl and 2-hydroxyphenyl diester of 2-chloroethylphosphonic acid.
7. The 2-chloroethyl monoester of 2-chloroethylphosphonic acid.
8. 2-bromethylphosphonic acid.
9. The bis(phenyl)ester of 2-chloroethylphosphonic acid.
10. The tetrachloropyrocatechol cyclic ester of 2-chloroethylphosphonic acid.
11. 2-iodoethylphosphonic acid.
12. The saligen cyclic ester of 2-chloroethylphosphonic acid.
13. Salicyclic acid cyclic ester of 2-chloroethylphosphonic acid.
14. The ethyl monoester of 2-bromoethylphosphonic acid.
15. The butyl monoester of 2-iodoethylphosphonic acid.
16. the 3-hydroxyphenyl monoester of 2-chloroethylphosphonic acid (which exists in polymeric form).
17. The bis(2-oxo-pyrrolidinylmethyl) ester of 2-chloroethylphosphonic acid.
18. the o-hydroxyphenyl monoester of 2-chloroethylphosphonic acid.
19. The mixed isopropyl and 2-hydroxyphenyl diester of 2-chloroethylphosphonic acid.
20. 2-fluoroethylphosphonic acid.
21. The mixed octyl and 2-hydroxyphenyl diester of 2-chloroethylphosphonic acid.
22. The mixed hexadecyl and 2-hydroxyphenyl diester of 2-chloroethylphosphonic acid.
23. The mixed tridecyl and 2-hydroxyphenyl diester of 2-chloroethylphosphonic acid.
24. The anhydride of 2-chloroethylphosphonic acid.
25. 2-chloroethylphosphonic acid.
26. The mixed butyl and 2-hydroxyphenyl diester of 2-chloroethylphosphonic acid.
27. The 2-bromoethyl) monoester of 2-bromoethylphosphonic acid.

Other useful phosphonic acid derivative compounds within formula 12 are salicyclic acid cyclic ester of phosphonamidic acid, the mixed phenyl and 2-hydroxyphenyl diester of 2-chloroethyldichlorophosphine, the bis (pentachlorophenyl) ester of 2-chloroethylphosphonic acid; 2-chloropropylphosphonic acid, 2-phenylthioethylphosphonic acid, the 2,3-pyridinedio cyclic ester of 2-chloroethylphosphonic acid, 2-chloroethylthiophosphonic acid, (2-bromo, 2-fluoro and 2-iodo) and 2-chloroethyl-2,3-dibromo-4-hydroxy-2-butenyl ester polymer. Salts of the phosphonic derivatives of this invention may be used. Examples of such salts include the sodium, aluminum, zinc, potassium and lithium salts.

Other illustrative ethylene response or ethylene-type response inducing agents which can be used in the synergistic plant growth regulator compositions of this invention include, for example, the following; certain 2-halogethanesulphinic acid compounds described in U.S. Pat. No. 3,885,951 and French Patent 2,128,660; certain beta-chloro- and beta-bromethanesulfinic acids and esters as described in U.S. Pat. Nos. 3,927,062 and 3,876,678; mixtures of a N-heterocyclic amide and a haloalkyl silane as described in U.S. Pat. No. 4,332,612; mixtures of a N-heterocyclic amide and a 2-haloethylsulfinate as described in U.S. Pat. No. 4,359,334. These agents can be prepared by conventional methods known in the art and many may be available from various suppliers.

Still other illustrative ethylene response or ethylene-type response including agents include gaseous ethylene and 1-amino-1-cyclopropane-carboxylic acid (ACC) which is capable of breaking down into ethylene in plant tissue.

The synergistic plant growth regulator compositions of this invention can display a wide variety of plant growth regulating properties or ethylene responses or ethylene-type responses, depending upon the concentration used, the formulation employed and the type of plant species treated. While the compositions may be regarded as achieving an ethylene response or an ethylene-type response, the present invention is not necessarily limited thereto since it is recognized that certain growth regulating responses achieved through the practice of the present invention may not be regarded as being technically traditional or known or to be discovered ethylene responses or even ethylene-type responses. Hence, it is preferred to regard the results achieved in the practice of the present invention as growth regulating responses.

In view of the foregoing, it can be seen that the term "method for regulation plant growth" or the term "growth regulation process" or the use of the words "growth regulation" or "plant growth regulator" or other terms using the word "regulate" as used in the specification and in the claims mean a variety of plant responses which attempt to improve some characteristic of the plant as distinguished from herbicidal action, the intention of which is to destroy a plant. For this reason, the synergistic plant growth regulator compositions of this invention are used in amounts which are non-phytotoxic with respect to the plant being treated.

Nevertheless, the synergistic plant growth regulator compositions of this invention can sometimes be used in a herbicidal context, for instance, to stimulate the growth of dormant rhiszomes in order to make such rhizomes more susceptible to a herbicide. However, even here the compositions are not themselves in any practical sense herbicides since they promote the growth of the unwanted plant or otherwise make it very susceptible to a true herbicide. Thus, the present invention can be carried out in conjunction with or in the presence of the other compound so mixtures which are herbicides.

By virtue of the practice of the present invention, a wide variety of plant growth responses, generally ethylene responses or ethylene-type responses can be achieved, including the following:

1. Increasing yields;
2. Auxin activity;
3. Inhibition of terminal growth, control of apical dominance, increase in branching and increase in tillering.
10. Changing biochemical compositions of plant;
5. Abscission of foliage, flowers and fruit or stimulation of separation of abscission zone;
6. Hastening ripening and color promotion in fruit and leaves;
7. Increasing flowering and fruiting and causing flower induction;
8. Abortion or inhibition of flowering and seed development;
9. Prevention of lodging;
10. Stimulation of seen germination and breaking of dormancy;
11. Resistance to freeze injury;
12. Hormone or epinasty effects;
13. Interactions with other growth regulators;
14. Interactions with herbicides; and
15. Disease resistance.

It is intended that as used in the appended claims the term "method for regulating plant growth" or "method for inducing an ethylene response" or "method of inducing an ethylene-type response" means the achievement of any of the aforementioned fifteen categories of response as well as any other modification of plant, seed, fruit, vegetable (whether the fruit or vegetable is unharvested or have been harvested) so long as the net result is to increase growth or benefit any property of the plant, seed, fruit or vegetable as distinguished from herbicidal action (unless the present invention is practiced in conjunction with or in the presence of a herbicide). The term "fruit" as used herein and in the appended claims is to be understood as meaning anything of economic value that is produced by the plant.

Certain preliminary details connected with the foregoing fifteen categories should make for a better appreciation of the invention.

1. Increasing Yields:

The synergistic plant growth regulator compositions are capable of increasing yields of many plants, including, but not limited to small grains, particularly oats (*Avena sativa*), wheat (*Triticum aestivum*), and barley (*Hordeum spp.*); and of increasing yields of other types of plants, such as beans and of cotton (*Gossypium hirsutum*);

2. Auxin Activity:

When applied, for instance, as a lanolin paste, to one side of a decapitated sunflower hypocotyl, the synergistic plant growth regulator compositions are capable of inducing bending of the hypocotyl away from the side of the application; they are also capable of inducing sprouting of underground rhizomes of monocotyledonous and dicotyledonous plants; of causing cell proliferation; and of inducing rooting, as illustrated by the production of large numbers of root primordia over the entire stem length of tomato plants (*Lycopersicon esculentum*) after these have been sprayed with an aqueous solution thereof—this type of response makes it possible to root cuttings either when taken from treated plants or after treatment of their cut ends.

3. Inhibition of Terminal Growth, Control of Apical Dominance, Increase in Branching, and Increase in Tillering:

These types of plant growth response can be produced on a variety of plant species when they are treated with synergistic plant growth regulator compositions including privet (*Liqustrum ovalifolium*), blueberry (*Vaccinum corymbosum*), azalea (*Rhododendron obtusum*), soybean (*Glycine max.*), snapbeans (*Phaseolus vulgaris*), tomatoes (*Lycopersicon esculentum*), alligator weed (*Alternanthua philoxerides*) and monoctyledons such as rice (*Oryza sativa*), johnsongrass (*Sorghum halepense*) and wild oats (*Avena fatua*). Thus type of response can also be of value in the control of roadside grasses. It has been suggested that the removal of the lead but (e.g., by pinching) should allow growth of axillary buds; but it is generally found that on removal of the lead bud, one of the axillary buds takes over the activity and dominance of the lead bud. The use of the synergistic plant growth regulator compositions, however, usually retards the activity of the lead bud for a while but then later restores the lead bud to normal growth, with production of normal flowers and normal fruit; and thus one avoids the permanent loss of buds inevitably associated with pinching. However, some plant species may respond differently when treated with synergistic plant growth regulator compositions for control of apical dominance—growth inhibition may extend to include not only the lead bud but also lateral buds along the stem. Examples of such plants are tobacco (*Nicotiana tabacum*) and chrysanthemum (*Chrysanthemum sp.*)—this type of response is useful for preventing sucker growth from lateral buds on tobacco.

4. Changing Biochemical Composition of Plant:

The synergistic plant growth regulator compositions are capable of measurably increasing the leaf area relative to the stem area in many plants, and the increased ratio of leaves to stem results in an increase in total protein on a per plant basis, and modification of the protein, carbohydrate, fat, nicotine and sugar within the treated plant. The synergistic plant growth regulator compositions are also capable of increasing latex flow in rubber tress to give a yield increase in dry rubber content.

5. Abscission of Foliage, Flowers and Fruit or Stimulation of Separation of Abscission Zone:

The synergistic plant growth regulator compositions may accelerate abscission of mature foliage on both perennial and annual plant species. They can be, for instance, quite active as defoliants on cotton and inhibit regrowth, and defoliation properties may also be observed in other plant species, such as roses, apples, citrus, and nursery stock, once the leaves have attained a mature state. Abscission of flowers and/or fruit following application of the synergistic plant growth regulator compositions may be observed on a variety of plant species, including applies (*Malus domestica*), pears (*Pyrus communis*), cherries (*Prunus avium*), pecans (*Carba illinoensis*), grapes (*Vitis vnifera*), olives (*Olea europaea*), coffer (*Coffea arabica*), and snapbeans (*Phaseolus vulgris*)—these abscission responses can be used to regulate flower production and as an aid in harvesting fruit. Stimulation of separation of abscission zone may be observed, for example, in boll opening of cotton or in shuck split of nuts such as walnuts, pecans and the like.

6. Hastening Ripening and Color Promotion in Fruit and Leaves;

The synergistic plant growth regulator compositions are capable of hastening the ripening of fruit (picked or unpicked) from a number of plant species, such as apples (*Malus domestica*), pears (*Pyrus communis*), cherries (*Prunus avium*), tomatoes (*Lycopersicon esculentum*), bananas and pineapples (*Ananas comosus*); and of removing the green color from harvestable leaves such as tobacco (*Nicotiana tabacum*) and regreened citrus such as oranges (*Citrus sinensis*) and lemons (*Citrus limon*).

7. Increasing Flowering and Fruiting and Causing Flower Induction:

Suitably applied, the syneristic plant growth regulator compositions are be capable of increasing flowering and fruiting and causing flower induction in a number of economic crops, such as soybeans (*Glycine max.*), snapbeans (*Phaseolus vulgaris*), kidney beans (*Phaseolus vulgaris*), zinnias (*Zinnia elegans*), pineapples and mangos.

8. Abortion or Inhibition of Flowering and Seed Development:

Suitably applied, the synergistic plant growth regulator compositions may inhibit flowering and/or abort seed development, for example, in johnsongrass (*Sorghum halepense*).

9. Prevention of Lodging:

Application of the synergistic plant growth regulator compositions may induce rigor resulting in firmer and stronger plants capable of resisting natural tendencies towards lodging. This effect may be observed on a number of plant species, such as, for example, wheat (*Triticum aestivum*), barley (*Hordeum vulgare*), and pea (*Pisum sativum*).

10. Stimulation of Seed Germination and Breaking of Dormancy:

The synergistic plant growth regulator compositions may stimulate the germination of, for instance, lettuce seed and to terminate the dormancy of tubers, such as seed potatoes.

11. Resistance to Freeze Injury:

The synergistic plant growth regulator compositions may increase the hardiness of various plant species, such as, for example, lima beans (*Phaseolus limensis*).

12. Hormone or Epinasty Effects:

The synergistic plant growth regulator compositions may produce hormone or epinasty effects upon various plants, including, notably tomatoes (*Lycopersicon esculentum*).

13. Interactions with other Growth Regulators:

The synergistic plant growth regulator compositions may, of course, be used in conjunction with other plant growth regulators, such as maleic hydrazide, N-dimethylaminosuccinamic acid, gibberellic acid and naphthaleneacetic acid, and interact therewith producing synergistic or antagonistic responses in various plants.

14. Interactions with Herbicides:

While the synergistic plant growth regulator compositions have essentially no phytotoxic activity of their own, they may be used in their capacity as plant growth regulators in conjunction with herbicides, for instance, with aminotriazole in the herbicidal control of Johnson grass (*Sorghum halepense*).

15. Disease Resistance:

Disease resistance makes tissue resistant to invasion by plant pathogens by influencing the enzyme and plant processes which regulate growth and natural disease immunity.

The proportional amount of the ethylene response or ethylene-type response inducing agent, i.e., agent (i), and the malonic acid derivative compound, i.e., compound (ii), in the synergistic plant growth regulator compositions of this invention is such that the amount of compound (ii) used with agent (i) results in a mixture having a greater plant growth regulating effect than the sum total plant growth regulating effect of agent (i) and compound (ii) used alone. The amount of agent (i) and compound (ii) can vary over a wide range depending on the particular agent and compound employed, the particular crop to be treated, the particular plant growth regulating effect desired, environmental and climatic conditions, and the like. The weight proportion of agent (i) to compound (ii) can be, for example, from about 0.1:1000 to about 1000:0.1 respectively. Preferably, the weight proportion of agent (i) to compound (ii) can be from about 1:500 to about 500:1. The amount of synergistic plant growth regulator composition should preferably be non-phytotoxic with respect to the plant being treated.

The synergistic plant growth regulator compositions of this invention can be prepared by conventional mixing methods and may be employed according to a variety of conventional methods known to those skilled in the art. Either combination (mix) or sequential application methods can be used according to this invention.

However, in sequential application methods, compound (ii) is generally applied prior to agent (i) to achieve a synergistic plant growth regulating response. Compositions containing agent (i) and compound (ii) as the active ingredient will usually comprise a carrier and/or diluent, either liquid or solid. As used herein, the active ingredient refers to the combination of agent (i) and compound (ii).

Suitable liquid diluents or carriers include water, petroleum distillates, or other liquid carriers with or without surface active agents. Liquid concentrates can be prepared by dissolving one of these compounds with a nonphytotoxic solvent such as acetone, xylene, nitrogenzene, cyclohexanone or dimethyl formamide and dispersing the active ingredients in water with the aid of suitable surface active emulsifying and dispersing agents.

The choice of dispersing and emulsifying agents and the amount employed are dictated by the nature of the composition and the ability of the agent to facilitate the dispersion of the active ingredient. Generally, it is desirable to use as little of the agent as is possible, consistent with the desired dispersion of the active ingredient in the spray so that rain does not re-emulsify the active ingredient after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust compositions, the active ingredient is dispersed in and on an appropriately divided solid carrier such as clay, talc, bentonite, diatomaceous earth, fuller's earth, and the like. In the formulation of the wettable powders, the aforementioned dispersing agents as well as lignosulfonates can be included.

The required amount of the active ingredient contemplated herein can be applied per acre treated in from 1 to 200 gallons or more of liquid carrier and/or diluent or in from about 5 to 500 pounds of inert solid carrier and/or diluent. The concentration in the liquid concentrate will usually vary from about 5 to 95 percent by weight and in the solid formulations from about 0.5 to about 90 percent by weight. Satisfactory sprays or dusts for general use contain from about 0.001 to about 100 pounds of active ingredient per acre, preferably from about 0.01 to about 15 pounds of active ingredient per acre, and more preferably from about 0.1 to about 5 pounds of active ingredient per acre.

Formulations useful in the conduct of this invention can also contain other optional ingredients such as stabilizers or other biologically active compounds, insofar as they do not impair of reduce the activity of the active ingredient and do not harm the plant being treated. Other biologically active compounds include, for example, one or more insecticidal, herbicidal, fungicidal, nematicidal, miticidal, plant growth regulators or other known compounds. Such combinations may be used for the known or other purpose of each ingredient and may provide a synergistic effect.

Although the preferred method of application of the synergistic plant growth regulator compositions is directed to the foliage and stems of plants, such compositions may be applied to the soil in which the plants are growing, and that such compositions may be root-absorbed to a sufficient extent so as to result in plant growth regulator responses in accordance with the teachings of this invention.

The synergistic plant growth regulator compositions of this invention are preferably applied to growing plants as set forth in many of the examples in this specification. However, under certain circumstances, the compositions used may be active in seed treatment, for instance, lettuce seeds and oat seeds, or root dipping.

The synergistic plant growth regulator compositions are preferably applied to plants and crops under average or normal growing conditions. The synergistic plant growth regulator compositions of this invention can be applied during the plant vegetation growth phase or the plant reproductive growth phase to obtain the desired plant growth regulator effects.

As used herein, plants refer in general to any agronomic or horticultural crops, ornamentals and turfgrasses. Illustrative of plants which can be treated by the synergistic plant growth regulator compositions of this invention include, for example, corn, cotton, sweet potatoes, white potatoes, alfalfa, wheat, rye, rice, barley, oats, sorghum, dry beans, soybeans, sugar beets, sunflowers, tobacco, tomatoes, canola, deciduous fruit, citrus fruit, tea, coffee, olives, pineapple, cocoa, banana, sugar cane, oil palm, herbaceous bedding plants, woody shrubs turfgrasses, ornamental plants, evergreens, trees, flowers, and the like. As used herein, crops refer in general to any of the illustrative aronomic or horticultural crops above.

The synergistic plant growth regulator compositions contemplated herein are effective for inducing a variety of plant growth regulating responses. Such compositions have a high margin of safety in that when used in sufficient amount to provide a plant growth regulating effect, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable plant growth regulating characteristic of the active ingredient or impart undesirable characteristics, for instance, phytotoxicity, to the active ingredients. Mixtures of the active composition can be employed if desired as well as combinations of the active composition with other biologically active compounds or ingredients as indicated above.

The following examples are illustrative of the present invention.

EXAMPLE I

Preparation of ethyl 3-[(4-fluorophenyl)amino]-3-oxopropanoate

Into a nitrogen-purged, air-stirred reaction flask was charged 4.44 grams (0.04 mol) of 4-fluoroaniline, 4.05 grams (0.04 mole) of triethylamine and 200 milliliters of tetrahydrofuran solvent. A 6.02 gram (0.04 mol) portion of ethyl malonyl chloride was then added rapidly by a dropping funnel to the mixture with good stirring at room temperature followed by a few milliliters of tetrahydrofuran as a rinse. The temperature of the stirred mixture rose to 42° C. and a white precipitate of triethylamine hydrochloride separate therefrom. The mixture was then stirred at ambient temperature for about 2 hours and the triethylamine hydrochloride filtered off, washed with solvent and dried to give 5.2 grams (0.04 mole). The filtrate was freed of solvent on a rotary evaporator and the resulting purple solid dissolved in methylene chloride, which solution was washed in succession with 2N HCl (3×75 milliliters), and water (2×75 milliliters), and then dried over magnesium sulfate and solvent vacuum stripped to give a crude solid product. Recrystallization from ethyl acetate-cyclohexane followed by flash column chromatography gave 3.47 grams (0.015 mole) of ethyl 3-[(4-fluorophenyl)amino]-3-oxopropanoate having a melting point of 68° C-71° C.

Elemental analysis of the product indicated the following: Analysis: $C_{11}H_{12}FNO_3$: Calculated: C, 58.66; H. 5.37; N, 6.22. Found: C, 58.61; H, 5.35; N, 6.36.

This compound is referred to hereinafter as Compound 1.

EXAMPLE II

In a manner similar to that employed in Example I, other compounds were prepared. The structures and analytical data for Compounds 2 through 76 are set forth in Table A below.

TABLE A

Representative Malonic Acid Derivative Compounds

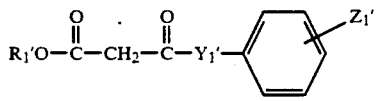

| Compound No. | Substituents | | | Elemental Analysis | | | | | | Melting Point °C. |
|---|---|---|---|---|---|---|---|---|---|---|
| | | | | Calculated | | | Found | | | |
| | $R_1'$ | $Z_1'$ | $Y_1'$ | C | H | N | C | H | N | |
| 2 | $C_2H_5$ | 4-Cl | $N(CH_3)$ | 56.36 | 5.52 | 5.48 | 56.25 | 5.53 | 5.21 | 49–52 |
| 3 | $C_2H_5$ | 4-CN | NH | 62.06 | 5.21 | 12.07 | 61.68 | 5.09 | 11.99 | 101–103 |
| 4 | $C_2H_5$ | 4-$C_2H_5$CO | NH | 63.86 | 6.51 | 5.32 | 63.79 | 6.57 | 5.34 | 67–70 |
| 5 | $C_2H_5$ | 3,5-$Cl_2$ | NH | 47.85 | 4.02 | 5.07 | 47.86 | 4.14 | 5.08 | 67–69 |
| 6 | $C_2H_5$ | 3-$CF_3$-4-Br | NH | 40.70 | 3.13 | 3.96 | 40.69 | 3.24 | 3.97 | 69–72 |
| 7 | $C_2H_5$ | 2-F-4-Cl-5-P(=O)(OCH$_2$CH$_3$)$_2$ | NH | 45.52 | 5.09 | 3.54 | 45.41 | 5.26 | 3.56 | 97–98 |
| 8 | $C_2H_5$ | 2,6-$(CH_3)_2$-4-Br | NH | 49.69 | 5.13 | 4.46 | 49.63 | 5.67 | 4.96 | 143–145 |
| 9 | $C_2H_5$ | 3-$CH_3$-4-Br | NH | 48.01 | 4.70 | 4.67 | 49.25 | 5.24 | 4.65 | 62–65 |
| 10 | $C_2H_5$ | 3-$CF_3$ | NH | 52.36 | 4.36 | 5.09 | 51.98 | 4.53 | 5.22 | 71–72.5 |
| 11 | $C_2H_5$ | 3-Cl | NH | 54.67 | 5.01 | 5.80 | 53.96 | 5.33 | 5.86 | Oil |
| 12 | $C_2H_5$ | 3,4-$Cl_2$ | O | 47.68 | 3.64 | — | 46.63 | 3.86 | — | Oil |
| 13 | $C_2H_5$ | 2,4-$(CH_3)_2$ | NH | 66.36 | 7.28 | 5.95 | 66.52 | 7.00 | 5.76 | 98–99 |
| 14 | $C_2H_5$ | 3,4-$(CH_3)_2$ | NH | 66.36 | 7.28 | 5.95 | 66.29 | 7.26 | 5.90 | 68–70 |
| 15 | $C_2H_5$ | 2-Cl-4-F | NH | 50.88 | 4.27 | 5.39 | 50.52 | 4.18 | 5.19 | 68–71 |
| 16 | $C_2H_5$ | 2-Cl | NH | 54.67 | 5.01 | 5.80 | 54.58 | 5.11 | 5.72 | 54–57 |
| 17 | $C_2H_5$ | 4-$CH_3$ | NH | NMR(CDCl$_3$): δ 1.17–1.39(t, 3H), 2.33(s, 3H), 3.45(s, 2H), 4.07–4.42(q, 2H), 6.99–7.57(m, 4H), 8.9–9.3(br, s, H) ppm. | | | | | | 80–83 |
| 18 | $C_2H_5$ | 2,6-$(CH_3)_2$ | NH | NMR(CDCl$_3$): δ 1.15–1.46(t, 3H), 2.23(s, 6H), 2.50(s, 2H), 4.07–4.50(q, 2H), 7.10(s, 3H), 8.37–8.78(br s, H) ppm. | | | | | | 97–100 |
| 19 | $C_2H_5$ | 2-$CF_3$-4-Cl | NH | 46.54 | 3.58 | 4.52 | 46.68 | 3.71 | 4.47 | 58.5–61 |
| 20 | $C_2H_5$ | 2,3-$Cl_2$ | NH | 47.85 | 4.02 | 5.07 | 47.84 | 4.05 | 5.07 | 72–75 |
| 21 | $C_2H_5$ | 2,5-$Cl_2$ | NH | 47.85 | 4.02 | 5.07 | 47.98 | 3.99 | 4.93 | 66–68 |
| 22 | $C_2H_5$ | 3,5-$Br_2$ | NH | 36.19 | 3.04 | 3.84 | 36.59 | 3.17 | 3.71 | 95–97 |
| 23 | $C_2H_5$ | 2-$CH_3$-5-Cl | NH | 56.37 | 5.52 | 5.48 | 56.76 | 5.72 | 5.26 | 96–98 |
| 24 | $C_2H_5$ | 3,4,5-$Cl_3$ | NH | 42.54 | 3.25 | 4.51 | 42.95 | 3.16 | 4.28 | 111–113 |
| 25 | $C_2H_5$ | 2-$CH_3$-4-Cl | NH | 56.37 | 5.52 | 5.48 | 56.00 | 5.67 | 5.21 | 103–104 |
| 26 | $C_2H_5$ | 2,4-$Cl_2$ | NH | 47.85 | 4.02 | 5.07 | 47.91 | 4.05 | 4.79 | 78–79 |
| 27 | $C_2H_5$ | 4-$CH_3$S— | NH | 56.89 | 5.97 | 5.53 | 56.75 | 5.90 | 5.48 | 73–75 |
| 28 | $C_2H_5$ | 3,5-$(CF_3)_2$ | NH | 45.49 | 3.23 | 4.08 | 45.96 | 3.23 | 4.02 | 72–75 |
| 29 | $C_2H_5$ | 2-$CH_3$O-5-Cl | NH | 53.04 | 5.19 | 5.16 | 53.65 | 5.31 | 5.14 | 86–87 |
| 30 | $C_2H_5$ | 4-I | NH | 39.66 | 3.63 | 4.20 | 39.30 | 3.68 | 4.08 | 108–110 |
| 31 | $C_2H_5$ | 4-$C_2H_5$O— | NH | 62.13 | 6.82 | 5.57 | 62.45 | 7.03 | 5.77 | 100–101 |
| 32 | $C_2H_5$ | 4-n-$C_4H_9$— | NH | 68.41 | 8.04 | 5.32 | 68.91 | 8.29 | 5.86 | Oil |
| 33 | $C_2H_5$ | 4-n-$C_6H_{13}$O— | NH | 66.42 | 8.20 | 4.56 | 67.18 | 8.35 | 4.58 | 66–68 |
| 34 | $C_2H_5$ | 4-n-$C_4H_9$O— | NH | 64.49 | 7.58 | 5.01 | 65.09 | 7.75 | 4.77 | 82–83 |
| 35 | $C_2H_5$ | 2,4,5-$Cl_3$ | NH | 42.54 | 3.25 | 4.51 | 42.40 | 3.09 | 4.39 | 104–105 |
| 36 | $C_2H_5$ | 2,4-$Br_2$ | NH | 36.19 | 3.04 | 3.84 | 36.29 | 2.93 | 3.77 | 83–85 |
| 37 | $C_2H_5$ | 2-Cl-4-Br | NH | 41.21 | 3.46 | 4.37 | 41.29 | 3.42 | 4.35 | 78–80 |
| 38 | $C_2H_5$ | 2-Br-4-Cl | NH | 41.21 | 3.46 | 4.37 | 41.59 | 3.61 | 4.55 | 81–83 |
| 39 | $C_2H_5$ | 4-$C_6H_5$CO— | NH | 69.44 | 5.51 | 4.50 | 69.75 | 5.51 | 4.48 | 87–88.5 |
| 40 | $C_2H_5$ | 3,4-$Br_2$ | NH | 36.19 | 3.04 | 3.84 | 36.27 | 3.33 | 3.68 | 64–67 |
| 41 | $C_2H_5$ | 2-F-4-Br | NH | 43.44 | 3.65 | 4.61 | 43.49 | 3.88 | 3.95 | 78.5–80 |
| 42 | $C_2H_5$ | 2-$CH_3$O-4-Cl | NH | 53.04 | 5.19 | 5.16 | 53.38 | 5.23 | 5.10 | 71–73 |
| 43 | $C_2H_5$ | 2-$CH_3$O-4,5-$Cl_2$ | NH | 47.08 | 4.28 | 4.58 | 47.31 | 4.64 | 4.59 | 95–98 |
| 44 | $C_2H_5$ | 2-$CH_3$-3,4-$Cl_2$ | NH | 49.67 | 4.52 | 4.83 | 49.86 | 4.62 | 4.69 | 90–93 |
| 45 | $C_2H_5$ | 2-F-4-Cl | NH | 50.88 | 4.27 | 5.39 | 50.90 | 4.56 | 5.21 | 66–69 |
| 46 | $C_2H_5$ | 3-Br-5-Cl | NH | 41.21 | 3.46 | 4.37 | 41.26 | 3.67 | 4.14 | 78–80 |
| 47 | n-$C_4H_9$ | 2-$CH_3$-4-Br | NH | 51.23 | 5.53 | 4.27 | 51.59 | 5.41 | 4.17 | 91–93 |
| 48 | $C_2H_5$ | 2-$CO_2$H-4-Br | NH | NMR(DMSO d$_6$): δ 1.16–1.43(t, 3H), 3.48 (s, 2H), 4.06–4.7(m, 4H), 7.5–8.7(m, 3H) ppm. | | | | | | 151–154 |
| 49 | $C_2H_5$ | 2-$CH_3$-3,5-$Cl_2$ | NH | 49.67 | 4.52 | — | 49.22 | 4.43 | — | 116–120 |
| 50 | $C_2H_5$ | 2-$CH_3$-4,5-$Cl_2$ | NH | 49.67 | 4.52 | 4.83 | 49.68 | 4.40 | 4.45 | 134–135.5 |
| 51 | $C_2H_5$ | 2-$C_2H_5$-4-Cl | NH | 57.89 | 5.98 | 5.19 | 58.26 | 6.06 | 5.24 | 98–99 |

TABLE A-continued

Representative Malonic Acid Derivative Compounds

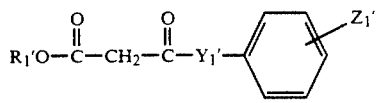

| Compound No. | Substituents | | | Elemental Analysis | | | | | | Melting Point °C. |
|---|---|---|---|---|---|---|---|---|---|---|
| | | | | Calculated | | | Found | | | |
| | $R_1'$ | $Z_1'$ | $Y_1'$ | C | H | N | C | H | N | |
| 52 | $C_2H_5$ | 2-$CH_3$-3-Cl | NH | 56.37 | 5.52 | 5.48 | 56.49 | 5.49 | 5.47 | 103–105 |
| 53 | $C_2H_5$ | 3-$NO_2$-4-Cl | NH | 46.08 | 3.87 | 9.77 | 46.52 | 4.00 | 9.43 | 81–83 |
| 54 | $C_2H_5$ | 2-$CH_3$ | NH | 65.14 | 6.83 | 6.33 | 63.60 | 6.51 | 6.12 | 68–71 |
| 55 | $C_2H_5$ | 2-$CH_3O$ | NH | 60.75 | 6.37 | 5.90 | 60.82 | 6.28 | 5.84 | 62–64 |
| 56 | $C_2H_5$ | 2,5-$(CH_3)_2$-3,4-$Cl_2$ | NH | 51.33 | 4.97 | 4.61 | 51.65 | 4.92 | 4.33 | 119–120 |
| 57 | $C_2H_5$ | 2-$CH_3O$-3,5-$Cl_2$ | NH | 47.08 | 4.28 | 4.58 | 47.10 | 4.22 | 4.61 | 90–92 |
| 58 | $C_2H_5$ | 2-$CH_3$-4-Br-5-Cl | NH | 43.07 | 3.92 | 4.19 | 41.85 | 4.31 | 3.72 | 132–135 |
| 59 | $C_2H_5$ | 4-(4-$ClC_6H_4O$) | NH | 61.18 | 4.83 | 4.20 | 61.27 | 4.94 | 4.14 | 86–87 |
| 60 | $C_2H_5$ | 3-[2-Cl-4-Cl-C₆H₃-CH(CH₃)-O-CH₂-] | NH | 58.55 | 5.16 | 3.41 | 58.91 | 5.23 | 3.29 | Oil |
| 61 | $C_2H_5$ | 4-[tetrahydronaphthyl-O-] | NH | 71.37 | 6.56 | 3.96 | 70.97 | 6.66 | 3.72 | 98–100 |
| 62 | $C_2H_5$ | 3-$C_6H_5O-$ | NH | 68.22 | 5.73 | 4.68 | 68.15 | 5.84 | 4.69 | Oil |
| 63 | $C_2H_5$ | 2,5-$Cl_2$-3-$CO_2CH_3$ | NH | 46.73 | 3.92 | 4.19 | 46.85 | 3.91 | 4.12 | Oil |
| 64 | $C_2H_5$ | 2,3-(CH=CHCH=CH) | NH | 70.02 | 5.88 | 5.44 | 70.30 | 6.00 | 5.51 | 78–80 |
| 65 | $C_2H_5$ | H | NH | 63.76 | 6.32 | 6.76 | 63.44 | 6.54 | 7.03 | Oil |
| 66 | $C_2H_5$ | 3,4-$Cl_2$ | NH | 47.85 | 4.02 | 5.07 | 47.76 | 4.09 | 5.36 | 80–83 |
| 67 | $C_2H_5$ | 4-$CF_3$ | NH | 52.37 | 4.39 | 5.09 | 52.17 | 4.56 | 5.17 | 78–79.5 |
| 68 | $C_2H_5$ | 4-$NO_2$ | NH | 52.38 | 4.80 | 11.11 | 52.20 | 4.27 | 11.14 | 98–101 |
| 69 | $C_2H_5$ | 4-Br | NH | 46.17 | 4.23 | 4.90 | 46.33 | 4.16 | 4.91 | 96–98 |
| 70 | $CH_2CH_2OCH_3$ | 2-$CH_3$-4-Br | NH | 47.29 | 4.88 | — | 47.56 | 5.02 | — | 93–95 |
| 71 | $C_2H_5$ | 2-$CO_2CH_3$-4-Br | NH | 45.37 | 4.10 | 4.07 | 45.61 | 4.07 | 4.29 | 99–100 |
| 72 | $C_2H_5$ | 2-Br-4-$CH_3$ | NH | 48.02 | 4.70 | 4.67 | 48.35 | 4.88 | 4.56 | 91–94 |
| 73 | $n-C_4H_9$ | 4-C≡N | NH | 64.60 | 6.20 | 10.76 | 64.13 | 6.29 | 10.94 | 50–53 |
| 74 | $C_2H_5$ | 3,5-$Cl_2$ | S | 45.06 | 3.44 | — | 44.81 | 3.68 | — | Oil |
| 75 | $C_2H_5$ | 2-$CH_3$-4-Br | NH | 48.02 | 4.70 | 4.67 | 48.10 | 4.85 | 4.71 | 114–116 |
| 76 | $C_2H_5$ | 2-$CH_3$-4-$CH_3O$ | NH | 62.14 | 6.83 | 5.57 | 61.47 | 6.78 | 5.30 | 109–110 |

EXAMPLE III

Preparation of ethyl 1-(2-methyl-4,5-dichlorophenylaminocarbonyl)cyclopropanecarboxylate Into a nitrogen-purged round bottom flask was charged 5.53 grams (0.03 mole) of 2-methyl-4,5-dichloroaniline, 3.18 grams (0.03 mole) of triethylamine and 190 milliliters of tetrahydrofuran solvent. With vigorous stirring, a 5.55 gram (0.03 mole) portion of ethyl 1-chlorocarbonylcyclopropanecarboxylate prepared in Example XVIII was added in one portion, after which the mixture was stirred at ambient temperature for a six-hour period. A precipitate of triethylamine hydrochloride was then filtered off and the filtrate vacuum stripped to give a light yellow solid. The solid was taken up in ether and the solution water-washed, dried over magnesium sulfate, and solvent evaporated to give a yellow powder. Recrystallization from ethyl acetate-hexane gave 4.51 grams (0.01 mole) of ethyl 1-(2-methyl-4,5-dichlorophenylaminocarbonyl)cyclopropanecarboxylate having a melting point of 105° C.–107° C.

Elemental analysis of the product indicated the following: Analysis: $C_{14}H_{15}Cl_2NO_3$: Calculated: C, 53.18; H, 4.78; N, 4.43. Found: C, 53.41; H, 4.76; N, 4.44.

This compound is referred to hereinafter as Compound 77.

EXAMPLE IV

In a manner similar to that employed in Example III, other compounds were prepared. The structures and analytical data for Compounds 78 through 96 are set forth in Table B below.

TABLE B
Representative Malonic Acid Derivative Compounds

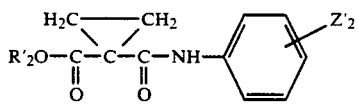

| Compound No. | Substituents R'₂ | Z'₂ | Elemental Analysis Calculated | | | Found | | | Melting Point °C. |
|---|---|---|---|---|---|---|---|---|---|
| | | | C | H | N | C | H | N | |
| 78 | C₂H₅ | 2,4,5-Cl₃ | 46.38 | 3.59 | 4.16 | 46.69 | 3.99 | 4.10 | 130–132.5 |
| 79 | C₂H₅ | 3,4-Cl₂ | 51.67 | 4.34 | 4.64 | 51.95 | 4.34 | 4.72 | 107–110 |
| 80 | C₂H₅ | 2,4-Cl₂ | 51.67 | 4.34 | 4.64 | 51.27 | 4.53 | 4.46 | 95–98 |
| 81 | C₂H₅ | 2,5-Cl₂ | 51.67 | 4.34 | 4.64 | 51.36 | 4.48 | 4.49 | 105–108 |
| 82 | C₂H₅ | 2-F-4-Cl | 54.65 | 4.59 | 4.90 | 54.92 | 4.71 | 4.85 | 94.5–96 |
| 83 | C₂H₅ | 4-Cl | 58.32 | 5.27 | 5.23 | 58.15 | 5.29 | 5.16 | 91–93 |
| 84 | C₂H₅ | 4-Br | 50.02 | 4.52 | 4.49 | 50.18 | 4.69 | 4.52 | 92.5–95 |
| 85 | C₂H₅ | 3,4-Br₂ | 39.92 | 3.35 | 3.58 | 40.18 | 3.47 | 3.60 | 128–130 |
| 86 | C₂H₅ | 3,5-Br₂ | 39.92 | 3.35 | 3.58 | 39.82 | 3.32 | 3.46 | 91–92.5 |
| 87 | C₂H₅ | 2,4-Br₂ | 39.92 | 3.35 | 3.58 | 40.02 | 3.61 | 3.77 | 102–103.5 |
| 88 | C₂H₅ | 2-Cl-4-Br | 45.04 | 3.78 | 4.04 | 45.28 | 3.98 | 3.90 | 109–110.5 |
| 89 | C₂H₅ | 2-Br-4-Cl | 45.04 | 3.78 | 4.04 | 44.89 | 4.29 | 3.80 | 95–96 |
| 90 | C₂H₅ | 3-Cl-4-Br | 45.04 | 3.78 | 4.04 | 45.16 | 4.20 | 3.79 | 113–116 |
| 91 | C₂H₅ | 2-CH₃-4-Br-5-Cl | 46.62 | 4.19 | 3.88 | 48.14 | 4.74 | 3.86 | 119–121 |
| 92 | C₂H₅ | 2-F-4-Br | 47.29 | 3.97 | 4.24 | 46.87 | 4.07 | 4.02 | 102–103 |
| 93 | C₂H₅ | H | 66.83 | 6.47 | 6.00 | 66.54 | 6.48 | 5.80 | 85–89 |
| 94 | C₂H₅ | 3,5-Cl₂ | 51.67 | 4.34 | 4.64 | 51.52 | 4.52 | 4.36 | 64–67 |
| 95 | C₂H₅ | 4-C≡N | 65.10 | 5.46 | 10.85 | 65.02 | 5.51 | 10.67 | 129–132 |
| 96 | C₂H₅ | 2-CH₃-4-Br | 51.55 | 4.94 | 4.29 | 51.72 | 4.74 | 4.31 | 89–91 |

EXAMPLE V

Preparation of 3-[(4-bromo-2-methylphenyl)amino]-3-oxopropanoic acid

A 6.0 gram (0.02 mole) portion of ethyl 3-[(4-bromo-2-methylphenyl)amino]-3-oxopropanoate prepared in Example I (Compound No. 75) was dissolved in approximately 80 milliliters of ethanol and 1.2 grams (0.03 mole) of sodium hydroxide pellets were added to the resulting mixture. The mixture was stirred for four hours and then allowed to stand overnight. The mixture was then evaporated to dryness and water added to give a yellow cloudy solution. This solution was extracted with methylene chloride and then acidified with 10% hydrochloric acid causing a white precipitate to form. The white precipitate was worked up to give 1.8 grams (0.01 mole) of 3[(4-bromo-2-methylphenyl)amino]-3-oxopropanoic acid as a white solid having a melting point of 163° C.–165° C.

Elemental analysis of the product indicated the following: Analysis: C₁₀H₁₀BrNO₃. Calculated: C, 44.14; H, 3.70; N, 5.15. Found: C, 43.90; H, 3.68; N, 5.11.

This compound is referred to hereinafter as Compound 97.

EXAMPLE VI

In a manner similar to that employed in Example V, other compounds were prepared. Compound 108 was obtained from Research Services, P.O. Box 11212, Santa Ana, Calif. 92711. Compound 109 was obtained from Dr. A. K. Mittal, 32/17 E. Patel Nagar, New Delhi 110 008, India. The structures and analytical data for Compounds 98 through 109 are set forth in Table C below.

TABLE C
Representative Malonic Acid Derivative Compounds

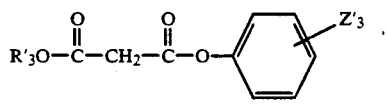

| Compound No. | Substituents R'₃ | Z'₃ | Elemental Analysis Calculated | | | Found | | | Melting Point °C. |
|---|---|---|---|---|---|---|---|---|---|
| | | | C | H | N | C | H | N | |
| 98 | H | 4-Cl | 50.60 | 3.77 | 6.56 | 50.67 | 3.80 | 6.37 | 140–141 |
| 99 | H | 2-CH₃-4-Br-5-Cl | 39.18 | 2.96 | 4.57 | 39.36 | 3.14 | 4.44 | 181–182 |
| 100 | H | 3,5-Br₂ | 32.08 | 2.09 | 4.16 | 32.34 | 2.33 | 4.04 | 164–165.5 |
| 101 | H | 2-F-4-Br | 39.15 | 2.56 | 5.07 | 39.24 | 2.42 | 4.94 | 161–162 |
| 102 | H | 2,4,5-Cl₃ | 38.26 | 2.14 | 4.96 | 38.51 | 2.12 | 4.84 | 174–174.5 |
| 103 | H | 2-Br-4-CH₃ | NMR(CDCl₃/DMSO-d₆): δ 2.27(s, 3H), 3.4(s, 2H), 6.95–8.01(m, 4H), 9.5–9.7(br s, H)ppm. | | | | | | 154–157 |
| 104 | H | 2-Br-4-Cl | 36.95 | 2.41 | 4.79 | 37.18 | 2.77 | 4.71 | 159–161 |
| 105 | H | 2-Cl-4-Br | 36.95 | 2.41 | 4.79 | 37.10 | 2.60 | 4.76 | 165.5–167 |
| 106 | H | 2,4-Br₂ | 32.08 | 2.09 | 4.16 | 32.27 | 2.23 | 4.13 | 157–159 |
| 107 | H | 3,4-Br₂ | 32.08 | 2.09 | 4.16 | 31.96 | 2.22 | 4.08 | 143–144 |
| 108 | H | 2,4-Cl₂ | NMR(CDCl₃/DMSO-d₆): δ 2.49–2.64(brs, H), 3.52(s, 2H), 7.17–8.24(m, 3H), 9.86–10.05(br s, H)ppm. | | | | | | — |

TABLE C-continued
Representative Malonic Acid Derivative Compounds

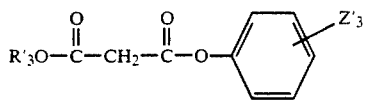

| Compound | Substituents | | Elemental Analysis | | | | | | Melting Point |
|---|---|---|---|---|---|---|---|---|---|
| | | | Calculated | | | Found | | | |
| No. | R'₃ | Z'₃ | C | H | N | C | H | N | °C. |
| 109 | H | 3-Cl-4-CH₃ | NMR(CDCl₃/DMSO-d₆): δ 2.30(s, 3H), 2.45-2.63(br s, H), 3.34(s, 2H), 7.05-7.86(m, 3H), 10.04-10.23(br s. H)ppm. | | | | | | — |

EXAMPLE VII

Preparation of 1-(2-methyl-4,5-dichlorophenylaminocarbonyl)cyclopropanecarboxylic acid A solution containing 0.34 gram (0.006 mole) of potassium hydroxide and 0.109 gram (0.006 mole) of water in 80 milliliters of ethanol was prepared in a 250 milliliter round bottom flask. With cooling to a temperature of 0° C. in an ice/NaCl bath and stirring, a solution of ethyl 1-(2-methyl-4,5-dichlorophenylaminocarbonyl)-cyclopropanecarboxylate prepared in Example III in a small volume of ethanol was added and the mixture allowed to stir with warming to room temperature over a 72 hour period. The mixture was vacuum evaporated to give a white solid residue which was dissolved in water and extracted twice with ether. The ether extracts were discarded. The water solution was acidified to a pH of 2 with 25% Hcl solution causing separation of a solid which was taken up into ether, and the acidified aqueous phase was extracted four times. The combined ether extracts were dried over magnesium sulfate and vacuum evaporated to give a white solid. This white solid was water-washed and dried in a vacuum oven to give 1.85 grams (0.006 mole) of 1-(2-methyl-4,5-dichlorophenylaminocarbonyl)cyclopropanecarboxylic acid having a melting point of 248° C.-251° C.

Elemental analysis of the product indicated the following: Analysis: $C_{12}H_{11}Cl_2NO_3$: Calculated: C, 50.02; H, 3.85; N, 4.88. Found: C, 50.51; H, 4.31; N, 4.83.

This compound is referred to hereinafter as Compound 110.

EXAMPLE VIII

In a manner similar to that employed in Example VII, other compounds were prepared. The structures and analytical data for Compounds 111 through 128 are set forth in Table D below.

TABLE D
Representative Malonic Acid Derivative Compounds

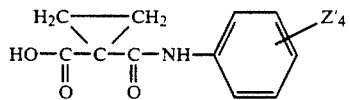

| Compound | Substituent | Elemental Analysis | | | | | | Melting Point |
|---|---|---|---|---|---|---|---|---|
| | | Calculated | | | Found | | | |
| No. | Z'₄ | C | H | N | C | H | N | °C. |
| 111 | 2-CH₃-4-Br | 48.34 | 4.06 | 4.70 | 48.20 | 4.06 | 4.66 | 204.5-206 |
| 112 | 2,4,5-Cl₃ | 42.82 | 2.61 | 4.54 | 43.11 | 3.14 | 4.42 | 250 |
| 113 | 2,5-Cl₂ | 48.20 | 3.31 | 5.11 | 48.33 | 3.26 | 4.96 | 223.5-226 |
| 114 | 2,4-Cl₂ | 48.20 | 3.31 | 5.11 | 45.26 | 3.40 | 5.03 | 189-190 |
| 115 | 2-F-4-Cl | 51.27 | 3.52 | 5.44 | 51.18 | 3.70 | 5.22 | 202-204 |
| 116 | 4-Cl | 55.12 | 4.21 | 5.84 | 54.69 | 4.35 | 5.59 | 217-219 |
| 117 | 4-Br | 46.50 | 3.55 | 4.93 | 46.36 | 3.45 | 4.86 | 220-222 |
| 118 | 3,4-Br₂ | 36.39 | 2.50 | 3.86 | 37.13 | 2.70 | 3.83 | 224-226.5 |
| 119 | 3,5-Br₂ | 36.39 | 2.50 | 3.86 | 36.99 | 2.60 | 3.82 | 211-212 |
| 120 | 2,4-Br₂ | 36.39 | 2.50 | 3.86 | 36.61 | 2.95 | 4.04 | 222-225 |
| 121 | 2-Cl-4-Br | 41.47 | 2.85 | 4.40 | 39.74 | 3.90 | 3.95 | 166-168(dec.) |
| 122 | 2-Br-4-Cl | 41.47 | 2.85 | 4.40 | 41.67 | 3.28 | 3.91 | 210-211 |
| 123 | 3-Cl-4-Br | 41.47 | 2.85 | 4.40 | 41.70 | 3.23 | 4.11 | 211-214 |
| 124 | 2-CH₃-4-Br-5-Cl | 43.33 | 3.33 | 4.21 | 45.47 | 4.08 | 3.91 | 231-234 |
| 125 | 2-F-4-Br | 43.73 | 3.00 | 4.64 | 43.97 | 3.05 | 4.30 | 203.5-207 |
| 126 | 4-CF₃ | 52.75 | 3.69 | 5.13 | 52.73 | 3.90 | 5.04 | 195-196.5 |
| 127 | 3,5-Cl₂ | NMR(CDCl₃): δ 1.52(s, 4H), 7.02-7.74(m, 4H), 10.08 (s, H)ppm. | | | | | | 198-202 |
| 128 | 3,4-Cl₂ | 48.20 | 3.31 | 5.11 | 48.79 | 3.80 | 5.26 | 220-222.5 |

EXAMPLE IX

Preparation of ethyl 1-(4-bromo-2-methylphenylaminocarbonyl)cyclobutanecarboxylate Into a nitrogen-purged reaction flask was charged 2.74 grams (0.01 mole) of 4-bromo-2-methylaniline and 1.49 grams (0.0) mole) of triethylamine dissolved in 200 milliliters of tetrahydrofuran. With vigorous stirring, 2.80 grams (0.01 mole) of ethyl 1-chlorocarbonylcyclobutanecarboxylate prepared in Example XIX were added and the resulting mixture stirred at ambient temperature for 6 hours. A precipitate of triethylamine hydrochloride was removed by filtration. The filtrate was vacuum stripped and the residue taken up in methylene chloride. This solution was washed successively with 2N HCl (2×75 milliliters) and water, and then dried over magnesium sulfate. Rotary evaporation gave a crude product which was flash chromatographed on silica using 7:3 hexane-ethyl acetate to give 3.68 grams (0.01 mole) of ethyl 1-(4-bromo-2-methylphenylaminocarbonyl)cyclobutanecarboxylate as a white solid. A small sample which was recrystallized from hexane had a melting point of 61° C.-64° C.

Elemental analysis of the product indicated the following: Analysis: $C_{15}H_{18}BrNO_3$: Calculated: C, 52.92; H, 5.33; N, 4.12. Found: C, 52.99; H, 5.44; N, 4.05.

This compound is referred to hereinafter as Compound 129.

and ethanolic potassium hydroxide (0.355 gram, 0.006 mole). The potassium salt of the acid was then acidified with 25% HCl solution and worked up in a manner similar to that described in Example VII to give 0.92 gram (0.003 mole) of 1-(3,5-dichlorophenylaminocarbonyl)cyclobutanecarboxylic acid as a beige-colored solid having a melting point of 159° C.-160° C.

Elemental analysis of the product indicated the following: Analysis: $C_{12}H_{11}Cl_2NO_3$; Calculated: C, 50.02, H, 3.85; N, 4.86. Found: C, 50.20; H, 3.83; N, 4.84.

This compound is referred to hereinafter as Compound 135.

EXAMPLE XII

In a manner similar to that employed in Example XI, other compounds were prepared. The structures and analytical data for Compounds 136 through 139 are set forth in Table F below.

TABLE F
Representative Malonic Acid Derivative Compounds

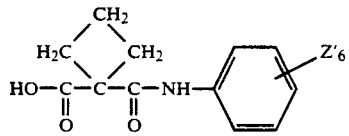

| Compound No. | Substituent $Z'_6$ | Elemental Analysis | | | | | | Melting Point °C. |
|---|---|---|---|---|---|---|---|---|
| | | Calculated | | | Found | | | |
| | | C | H | N | C | H | N | |
| 136 | 2,4,5-Cl$_3$ | 44.68 | 3.12 | 4.34 | 44.88 | 3.14 | 4.23 | 146–147 |
| 137 | 2,4-Cl$_2$ | 50.02 | 3.85 | — | 50.22 | 4.30 | — | 129–132 |
| 138 | 3,4-Cl$_2$ | 50.02 | 3.85 | — | 50.22 | 4.70 | — | 151–153 |
| 139 | 4-Cl | 56.81 | 4.77 | — | 56.99 | 4.94 | — | 159–161 |

EXAMPLE X

In a manner similar to that employed in Example IX, other compounds were prepared. The structures and analytical data for Compounds 130 through 134 are set forth in Table E below.

TABLE E
Representative Malonic Acid Derivative Compounds

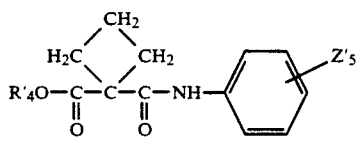

| Compound No. | Substituents | | Elemental Analysis | | | | | | Melting Point °C. |
|---|---|---|---|---|---|---|---|---|---|
| | R'$_4$ | Z'$_5$ | Calculated | | | Found | | | |
| | | | C | H | N | C | H | N | |
| 130 | C$_2$H$_5$ | 3,5-Cl$_2$ | 53.18 | 4.78 | 4.43 | 52.84 | 4.87 | 4.23 | 76.5–80 |
| 131 | C$_2$H$_5$ | 2,4,5-Cl$_3$ | 47.95 | 4.02 | 4.00 | 47.25 | 3.70 | 3.94 | 47–49 |
| 132 | C$_2$H$_5$ | 2,4-Cl$_2$ | 53.18 | 4.78 | 4.43 | 52.84 | 4.67 | 5.11 | Oil |
| 133 | C$_2$H$_5$ | 3,4-Cl$_2$ | 53.18 | 4.78 | 4.43 | 53.14 | 4.71 | 5.92 | Oil |
| 134(a) | C$_2$H$_5$ | 4-Cl | 59.68 | 5.73 | — | 59.89 | 5.70 | — | 85.5–87 |

(a)Prepared by the mixed anhydride procedure of Example XXXIII.

EXAMPLE XI

Preparation of 1-(3,5-dichlorophenylaminocarbonyl)cyclobutanecarboxylic acid

A 2.0 gram (0.006 mole) portion of ethyl 1-(3,5-dichlorophenylaminocarbonyl)cyclobutanecarboxylate prepared in Example X (Compound 130) was hydrolyzed in the presence of water (0.114 gram, 0.006 mole)

EXAMPLE XIII

Preparation of ethyl 1-(4-bromo-2-methylphenylaminocarbonyl)cyclopentanecarboxylate Ethyl 1-chlorocarbonylcyclopentanecarboxylate (3.10 grams, 0.02 mole) prepared in Example XX, 4-bromo-2-methylaniline (2.82 grams, 0.02 mole) and triethylamine (1.53 grams, 0.02 mole) were reacted in tetrahydrofuran (200 milliliters) under conditions similar to those described in Example I to give 2.40 grams (0.007 mole) of ethyl 1-(4-bromo-2-methylphenylaminocarbonyl)cyclopentanecarboxylate which, after recrystallization from hexane, had a melting point of 64° C.-67° C.

Elemental analysis of the product indicated the following: Analysis: $C_{16}H_{20}BrNO_3$; Calculated: C, 54.25; H, 5.69; N, 3.95. Found: C, 54.05; H, 5.55; N, 3.81.

This compound is referred to hereinafter as Compound 140.

EXAMPLE XIV

Preparation of ethyl 2-(4-bromo-2-methylphenylaminocarbonyl)butanoate

Ethyl 2-(chlorocarbonyl)butanoate (5.8 grams, 0.03 mole), 4-bromo-2-methylaniline (5.0 grams, 0.03 mole) and triethylamine (3.27 grams, 0.03 mole) were reacted under conditions similar to that described for Example I to give 7.4 grams (0.02 mole) of ethyl 2-(4-bromo-2-methylphenylaminocarbonyl)butanoate as a white solid having a melting point of 98° C.-100° C.

Elemental analysis of the product indicated the following: Analysis: $C_{14}H_{18}BrNO_3$; Calculated: C, 51.23; H, 5.53; N, 4.27. Found: C, 51.40; H, 5.63; N, 4.25.

This compound is referred to hereinafter as Compound 141.

EXAMPLE XV

In a manner similar to that employed in Example XIV, other compounds were prepared. The structures and analytical data for Compounds 142 through 152 are set forth in Table G below.

TABLE G

Representative Malonic Acid Derivative Compounds

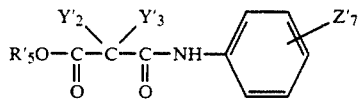

| Compound No. | Substituents | | | | Elemental Analysis | | | | | | Melting Point °C. |
|---|---|---|---|---|---|---|---|---|---|---|---|
| | | | | | Calculated | | | Found | | | |
| | $Y'_2$ | $Y'_3$ | $R'_5$ | $Z'_7$ | C | H | N | C | H | N | |
| 142 | $C_6H_5$ | H | $C_2H_5$ | 2-$CH_3$-4-Br | 57.46 | 4.82 | 3.72 | 57.39 | 4.78 | 3.95 | 115–117 |
| 143 | $C_6H_5$ | H | $C_2H_5$ | 2,3-(CH=CHCH=CH)— | 75.66 | 5.74 | 4.20 | 75.60 | 6.02 | 4.11 | 115–117 |
| 144 | Br | $CH_3$ | $C_2H_5$ | 2-$CH_3$-4-Br | 39.72 | 3.85 | 3.56 | 40.13 | 3.68 | 3.62 | Oil |
| 145 | Br | $CH_3$ | $C_2H_5$ | 4-Cl | 43.07 | 3.92 | 4.19 | 43.24 | 4.29 | 3.99 | Oil |
| 146 | Br | $CH_3$ | $C_2H_5$ | 3,4-$Cl_2$ | 39.05 | 3.28 | — | 39.58 | 3.74 | — | Oil |
| 147 | Br | $CH_3$ | $C_2H_5$ | 2,4-$Cl_2$ | 39.05 | 3.28 | 3.80 | 39.56 | 3.54 | 3.88 | Oil |
| 148 | Br | $CH_3$ | $C_2H_5$ | 3,5-$Cl_2$ | 39.05 | 3.28 | 3.80 | 39.80 | 3.53 | 3.86 | Oil |
| 149 | $CH_3$ | $CH_3$ | $C_2H_5$ | 2-$CH_3$-4-Br | 51.23 | 5.53 | 4.27 | 51.49 | 5.55 | 4.17 | Oil |
| 150 | $C_2H_5$ | $C_2H_5$ | $C_2H_5$ | 2-$CH_3$-4-Br | 53.94 | 6.23 | 3.93 | 53.89 | 6.36 | 3.52 | Oil |
| 151 | $CH_3$ | H | $C_2H_5$ | 2-$CH_3$-4-Br | 49.70 | 5.13 | 4.46 | 49.59 | 5.18 | 4.41 | 117–118 |
| 152 | Br | $CH_3$ | $C_2H_5$ | 4-C≡N | 48.02 | 4.03 | 8.62 | 48.17 | 4.53 | 8.74 | Oil |

C. NMR analysis of the product indicated the following:

NMR (CDCl$_3$-DMSO d$_6$): δ2.05 (s, 3H), 2.20 (s, 3H), 2.4–2.6 (br, s, H), 7.2–7.53 (m, 3H), 9.6–9.8 (br s, H) ppm.

This compound is referred to hereinafter as Compound 153.

EXAMPLE XVII

Preparation of N-butyl 3-[(4-bromo-2-methylphenyl)amino]-3-oxopropanamide

A mixture of 4.90 grams (0.02 mole) of ethyl 3-[(4-bromo-2-methylphenyl)amino]-3-oxopropanoate prepared in Example I (Compound No. 75), 358 grams (4.9 moles) of n-butylamine, 150 milliliters of ethanol and 5 drops of water was stirred at room temperature for about 16 hours. After this period, rotary evaporation gave a crude product as a white solid. The white solid was recrystallized from ethyl acetate-hexane to give 3.08 grams (0.009 mole) of N-butyl 3-[(4-bromo-2-methylphenyl)amino]-3-oxopropanamide having a melting point of 123° C.-125° C.

Elemental analysis of the product indicated the following: Analysis: $C_{14}H_{19}BrN_2O_2$; Calculated: C, 51.38; H, 5.85; N, 8.56. Found: C, 51.42; H, 5.91; N, 8.69.

This compound is referred to hereinafter as Compound 154.

EXAMPLE XVIII

EXAMPLE XVI

Preparation of 3-[(4-bromo-2-methylphenyl)amino]-2-bromo-2-methyl-3-oxopropanoic acid A 1.25 gram (0.003 mole) portion of ethyl 3-[(4-bromo-2-methylphenyl)amino]-2-bromo-2-methyl-3-oxopropanoate prepared in Example XV (Compound 144) was hydrolyzed with water (0.06 gram, 0.003 mole) and ethanolic potassium hydroxide (0.21 gram, 0.003 mole). The potassium salt of the acid was then acidified with concentrated HCl and worked up in a manner similar to that described in Example VII to give 1.04 grams (0.003 mole) of 3-[(4-bromo-2-methylphenyl)amino]-2-bromo-2-methyl-3-oxopropanoic acid as a white solid having a melting point of 133° C.-136°

Preparation of ethyl 1-chlorocarbonylcyclopropanecarboxylate

Into a stirred solution containing 15.1 grams (0.27 mole) of potassium hydroxide in 240 milliliters of ethanol and 4.83 grams (0.27 mole) of water was added dropwise, with cooling at a temperature of 0° C., 50.0 grams (0.27 mole) of diethyl 1,1-cyclopropanedicarboxylate. The mixture was stirred for about 16 hours at room temperature. Solvent was removed under reduced pressure to give a white residue which was dissolved in water and extracted with ether. The water solution was acidified to a pH of 2 with 25% aqueous hydrochloric acid and the organic acid was extracted from the aqueous suspension with ethyl ether (4×400 milliliters). The ether extract was dried over magnesium sulfate and vacuum stripped to give the monocarboxylic acid as a clear liquid. The clear liquid was dissolved in 300 milliliters of methylene chloride after which 74 grams (0.62 mole) of thionyl chloride were added, and the resulting mixture was then heated under reflux for approximately 16 hours. Volatiles were removed under reduced pressure to give 45.7 grams (0.25 mole) of ethyl 1-chlorocarbonylcyclopropanecarboxylate. NMR analysis of the product indicated the following:

NMR (CDCl$_3$): $\delta$1.22–1.50 (t, 3H), 1.75 (s, 4H), 4.1–4.52 (q, 2H) ppm.

This compound is referred to hereinafter as Compound 155.

EXAMPLE XIX

Preparation of ethyl 1-chlorocarbonylcyclobutanecarboxylate

Diethyl 1,1-cyclobutanedicarboxylate (20.0 grams, 0.10 mole) was saponified with 6.59 grams (0.10 mole) of potassium hydroxide in a mixture of 200 milliliters of ethanol and 1.80 grams (0.10 mole) of water and worked up to give the monocarboxylic acid which was reacted with thionyl chloride (8.86 grams, 0.07 mole) in methylene chloride solution as described in Example XVIII. Removal of the solvent gave 7.48 grams (0.04 mole) of ethyl 1-chlorocarbonylcyclobutanecarboxylate. NMR analysis of the product indicated the following:

NMR (CDCl$_3$): $\delta$1.10–1.44 (t, 3H), 1.7–2.85 (m, 6H), 4.05–4.5 (q, 2H) ppm.

This compound is referred to hereinafter as Compound 156.

EXAMPLE XX

Preparation of ethyl 1-chlorocarbonylcyclopentanecarboxylate

In a manner similar to the procedure described in Example XVIII, with the exception that refluxing with thionyl chloride in methylene chloride was conducted for only a 2 hour period, a 10 gram (0.05 mole) portion of diethyl 1,1-cyclopentanedicarboxylate was converted into 5.67 grams (0.03 mole) of ethyl 1-chlorocarbonylcyclopentanecarboxylate. NMR analysis of the product indicated the following:

NMR (CDCl$_3$): $\delta$1.10–1.49 (t, 3H), 1.56–2.48 (m, 8H), 4.0–4.5 (q, 2H) ppm.

This compound is referred to hereinafter as Compound 157.

EXAMPLE XXI

Preparation of ethyl 2bromo-2-chlorocarbonylpropanoate

In a manner similar to the procedure described in Example XVIII, except that refluxing with thionyl chloride in methylene chloride solution was conducted only a 6 hour period followed by standing at room temperature for about 16 hours, a 25.0 gram (0.10 mole) portion of diethyl 2-bromo-2methylmalonate was converted into 12.94 grams (0.05 mole) of ethyl 2-bromo-2-chlorocarbonylpropanoate. This compound was employed in the preparation of Compound Nos. 144–148 and 152 in Example XV. NMR analysis of the product indicated the following:

NMR (CDCl$_3$): $\delta$1.10–1.47 (t, 3H), 2.05–2.17 (s pair, 3H), 4.05–4.55 (q, pair, 2H) ppm.

This compound is referred to hereinafter as Compound 158.

EXAMPLE XXII

Preparation of ethyl 3-[(4-chlorophenyl)amino]-3-oxopropanoate

4-Chloroaniline (25.4 grams, 0.20 mole) and diethyl malonate (48 grams, 0.30 mole) were reacted in a manner similar to the procedure described by A. K. Sen and P. Sengupta, Jour. Indian Chem. Soc. 46 (9), 857–859 (1969) The reaction afforded a greenish colored solid which was recrystallized from toluene-hexane (1:1) and then from isopropyl ether to give 9.0 grams (0.04 mole) of ethyl 3-[(4-chlorophenyl)amino]-3-oxopropanoate as white crystals having a melting point of 82° C.–83° C.

Elemental analysis of the product indicated the following: Analysis: C$_{11}$H$_{12}$ClNO$_3$; Calculated: C, 54.67; H, 5.01; N, 5.80. Found: C, 54.90; H, 4.94; N, 6.07;

This compound is referred to hereinafter as Compound 159.

EXAMPLE XXIII

Preparation of ethyl 3-[(4-methylthiazol-2-yl) amino]-3-oxopropanoate

In a manner similar to the procedure described in Example I, 2-amino-4-methylthiazole was reacted with ethyl malonyl chloride employing triethylamine as the acid acceptor in tetrahydrofuran solution. The ethyl 3-[(4-methylthiazol-2-yl)amino]-3-oxopropanoate product (7.5 grams, 0.03 mole) was obtained as an off-white solid having a melting point of 138° C.–141° C.

Elemental analysis of the product indicated the following:

Analysis: C$_9$H$_{12}$N$_2$O$_3$S; Calculated: C, 47.36; H, 5.30; N, 12.27. Found: C. 47.50; H, 4.62; N, 11.77.

This compound is referred to hereinafter as Compound 160.

EXAMPLE XXIV

In a manner similar to that employed in EXAMPLE XXIII, other compounds were prepared. Compound 173 was obtained from Clarkson College of Technology, Potsdam, N.Y. The structures and analytical data for compounds 161 through 173 are set forth in Table H below.

TABLE H

Representative Malonic Acid Derivative Compounds

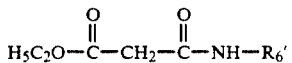

| Compound No. | R$_6'$ | Elemental Analysis | | | | | | Melting Point °C. |
|---|---|---|---|---|---|---|---|---|
| | | Calculated | | | Found | | | |
| | | C | H | N | C | H | N | |
| 161 | 4-chloro-2-methylbenzothiazole | 48.25 | 3.71 | 9.38 | 48.48 | 3.29 | 9.24 | 155–157 |
| 162 | 4-phenyl-2-methylthiazole | 57.92 | 4.86 | 9.65 | 58.08 | 4.63 | 9.62 | 164–168 |
| 163 | 6-bromo-2-methylbenzothiazole | 42.00 | 3.23 | 8.16 | 41.75 | 2.20 | 7.92 | 210 (dec.) |
| 164 | 3-methyl-5-methylisoxazole | 50.94 | 5.70 | 13.20 | 51.13 | 5.69 | 13.17 | 63–65 |
| 165 | 3-methyl-5-methylisoxazole (isomer) | 50.94 | 5.70 | 13.20 | 50.63 | 5.15 | 13.32 | 127–129 |
| 166 | 3-methyl-5-methylisothiazole | 47.36 | 5.30 | 12.27 | 47.41 | 5.46 | 11.76 | 90–92 |
| 167 | 5-bromo-3-methylisothiazole | 32.78 | 3.09 | 9.56 | 32.76 | 2.34 | 9.62 | 163–165 |
| 168 | 3-ethyl-5-methyl-thiadiazole | 44.43 | 5.38 | 17.27 | 44.13 | 5.41 | 17.41 | 148–150 |
| 169 | 2-chloro-3-methylpyridine | 49.50 | 4.57 | 11.54 | 49.30 | 4.57 | 11.54 | 65–68 |
| 170 | 2-chloro-5-methylpyridine | 49.50 | 4.57 | 11.54 | 49.34 | 4.64 | 11.69 | 99–100 |
| 171 | 4-chloro-6-methylpyrimidine | 46.61 | 4.70 | 16.31 | 49.88 | 4.83 | 16.24 | 132–136 |

TABLE H-continued

Representative Malonic Acid Derivative Compounds $$H_5C_2O-\overset{O}{\underset{\|}{C}}-CH_2-\overset{O}{\underset{\|}{C}}-NH-R_6'$$

| Compound No. | $R_6'$ | Elemental Analysis | | | | | | Melting Point °C. |
|---|---|---|---|---|---|---|---|---|
| | | Calculated | | | Found | | | |
| | | C | H | N | C | H | N | |
| 172 | (thiophene-CH$_2$–) | 52.85 | 5.76 | 6.16 | 53.01 | 5.81 | 6.11 | Oil |
| 173 | (2,4,6-trimethylpyridinyl) | NMR(CDCl$_3$): δ 1.11–1.45(t, 3H), 2.20(s, 3H), 2.36(s, 3H), 3.46(s, 2H), 4.03–4.48(q, 2H), 6.76(s, H), 7.83 (s, H), 9.06–9.51(br s, H)ppm. | | | | | | 109–129 |

EXAMPLE XXV

Preparation of ethyl 2-chlorocarbonyl-3-methyl-2-butenoate

Diethyl isopropylidenemalonate (30.0 grams, 0.15 mole) was saponified with 10.0 grams (0.15 mole) of potassium hydroxide in 200 milliliters of ethanol solution and worked up to give the monocarboxylic acid which was then reacted with thionyl chloride (10 milliliters, 0.1 mole) in methylene chloride solution in a manner similar to the procedure described in Example XVIII. Removal of solvent gave 9.6 grams (0.05 mole) of ethyl 2-chlorocarbonyl-3-methyl-2-butenoate. NMR analysis of the residue product in CDCl$_3$ solution indicated complete conversion of the carboxylic acid to the acid chloride as evidenced by absence of a downfield carboxylic acid proton. This compound is referred to hereinafter as Compound 174.

EXAMPLE XXVI

Preparation of ethyl 2-[(4-bromo-2-methylphenyl)aminocarbonyl)]-3-methyl-2-butenoate In a manner similar to the procedure described in Example I, ethyl 2-chlorocarbonyl-3-methyl-2-butenoate (9.6 grams, 0.05 mole) prepared in Example XXV, 4-bromo-2-methylaniline (5.3 grams, 0.03 mole) and triethylamine (4.0 milliliters, 0.03 mole) were reacted to give 2.9 grams (0.009 mole) of ethyl 2-[(4-bromo-2-methylphenyl)aminocarbonyl]-3-methyl-2-butenoate as a white solid having a melting point of 116° C.–119° C. NMR analysis of the product indicated the following:

NMR (CDCl$_3$): δ1.17–1.43 (t, 3H), 2.10–2.19 (d, 6H), 2.28 (s, 3H), 4.08–4.50 (q, 2H) 7.21–8.20 (m, 4H) ppm.

This compound is referred to hereinafter as Compound 175.

EXAMPLE XXVII

Preparation of 3,4-dichloro-2,5-dimethylaniline

A solution of 5.0 grams (0.03 mole) of 3,4-dichloro-2,5-dimethyl-1-nitrobenzene in 70 milliliters of ethanol was hydrogenated at room temperature at 50 psi in the presence of 0.25 gram of 10% palladium on activated carbon as a catalyst. Working up the reaction mixture gave 1.21 grams (0.006 mole) of 3,4-dichloro-2,5-dimethylaniline as a yellow solid having a melting point of 72° C.–76° C. NMR analysis of the product indicated the following:

NMR (CDCl$_3$): δ2.24 (s, 3H), 2.32 (s, 3H), 3.60 (br s , 2H), 6.50 (s,H) ppm.

This compound is referred to hereinafter as Compound 176.

EXAMPLE XXVIII

Preparation of 4,5-dichloro-2-methoxyaniline

Part A: Preparation of 2,2-dimethyl-N-(4-chloro-2-methoxyphenyl)propanamide

In to a stirred solution containing 10.0 grams (0.06 mole) of 4-chloro-2-methoxyaniline and 6.42 grams (0.06 mole) of triethylamine in 200 milliliters of tetrahydrofuran was added 7.65 grams (0.06 mole) of trimethylacetyl chloride in a small amount of tetrahydrofuran solvent. The resulting mixture was stirred for two hours at room temperature. Triethylamine hydrochloride precipitated and was filtered off and the filtrate vacuum stripped to give a dark liquid which was taken up in methylene chloride. This solution was washed with 2N HCl (2×100 milliliters), then with water (1×100 milliliters), dried over magnesium sulfate and solvent evaporated to give a crude product which was crystallized from hexane to give 6.82 grams (0.03 mole) of 2,2-dimethyl-N-(4-chloro-2-methoxyphenyl)-propanamide as a first and second crop. NMR analysis of the product indicated the following:

NMR (CDCl$_3$): δ1.32 (s, 9H), 3.91 (s, 3H), 6.83–7.08 (m, 2H), 8.28–8.52 (d, 2H) ppm.

Part B: Preparation of 2,2-dimethyl-N-(4,5-dichloro-2-methoxyphenyl)propanamide

Into a stirred solution containing 6.82 grams (0.03 mole) of 2,2-dimethyl-N-(4-chloro-2-methoxyphenyl)-propanamide prepared in Part A in 150 milliliters of chloroform was added 3.81 grams (0.03 mole) of sulfuryl chloride over a 40 minute period. The resulting reaction mixture was heated under reflux for a 3 day period, each day cooling the mixture and adding an additional 3.81 grams (0.03 mole) of sulfuryl chloride before continuing the reflux. At the end of 3 days, thin layer chromatographic and analysis of the mixture indicated the reaction to be complete. Volatiles were removed from the reaction mixture and 3.70 grams (0.01 mole) of 2,2-dimethyl-N-(4,5-dichloro-2-methoxyphenyl)propanamide recovered as a light yellow-orange solid by flash column chromatography eluting with dichloromethane. NMR analysis of this product indicate the following:

NMR (CDCl$_3$): δ1.34 (s, 9H), 3.92 (s, 3H), 6.94 (s, H), 8.08 (br s H), 8.67 (s, H) ppm.

Part C: Preparation of 4,5-dichloro-2-methoxyaniline

The 2,2-dimethyl-N-(4,5-dichloro-2-methoxyphenyl)propanamide (3.70 grams, 0.01 mole) prepared in Part B was dissolved in ethanol: 12N HCl (1:1), the mixture heated under reflux overnight and then freed of volatiles under rotary evaporation. Partition between 2N HCl and dichloromethane gave and acid-soluble fraction which was worked up to give 1.1 grams (0.01 mole) or pure 4,5-dichloro-2-methoxyaniline as determined by thin layer chromatographic analysis. The dichloromethane fraction from above was freed of solvent giving starting material which was again refluxed overnight with ethanol: 12N HCl and worked up to given an additional 1.2 grams (0.01 mole) of pure 4,5-dichloro-2-methoxyaniline as determined by thin layer chromatographic analysis. NMR analysis of the product indicated the following:

NMR (CDCl$_3$): δ3.88 (s, 5H), 6.73-6.90 (d, 2H) ppm.

This compound is referred to hereinafter as Compound 177.

EXAMPLE XXIX

Preparation of ethyl 3-[(3,5-difluorophenyl)amino]-3-oxopropanoate 3,5-Difluoroaniline (3.19 grams 0.02 mole) and ethyl malonyl chloride (3.71 grams, 0.02 mole) were reacted in the presence of triethylamine (2.50 grams, 0.02 mole) in 200 milliliters of methylene chloride in a manner similar to that described in Example I to give 2.71 grams (0.01 mole) of ethyl 3-[(3,5-difluorophenyl)amino]-3-oxopropanoate having a melting point of 42° C.-45° C.

Elemental analysis of the product indicated the following: Analysis: C$_{11}$H$_{11}$F$_2$NO$_3$; Calculated: C, 54.32; H, 4.56; N, 5.76. Found: C, 54.38; H, 4.92; N, 5.42.

This compound is referred to hereinafter as Compound 178.

EXAMPLE XXX

Preparation of ethyl 3-[(2,4-difluorophenyl)amino]-3-oxopropanoate 2,4-Difluoroaniline (5.00 grams, 0.04 mole) and ethyl malonyl chloride (5.83 grams, 0.04 mole) were reacted in the presence of triethylamine (3.92 grams, 0.04 mole) in a manner similar to that described in Example I to give 4.90 grams (0.02 mole) of ethyl 3-[(2,4-difluorophenyl)amino]-3-oxopropanoate having a melting point of 66° C.-68° C.

Elemental analysis of the product indicated the following: Analysis: C$_{11}$H$_{11}$F$_2$NO$_3$; Calculated: C, 54.32; H, 4.56. Found: C, 54.37; H, 4.60.

This compound is referred to hereinafter as Compound 179.

EXAMPLE XXXI

Preparation of 1-(2,4-difluorophenylaminocarbonyl)cyclopropanecarboxylic acid

A 5.00 gram (0.02 mole) portion of ethyl 1-(2,4-difluorophenylaminocarbonyl)cyclopropanecarboxylate prepared in Example XLIV (Compound 199) was hydrolyzed in a manner similar to that described in Example VII to give 4.26 grams (0.02 mole) of 1-(2,4-difluorophenylaminocarbonyl)cyclopropanecarboxylic acid having a melting point of 160° C.-163° C.

Elemental analysis of the product indicated the following: Analysis: C$_{11}$H$_9$F$_2$NO$_3$; Calculated: C, 54.77; H, 3.76. Found: C, 54.79; H, 3.85.

This compound is referred to hereinafter as Compound 180.

EXAMPLE XXXII

Preparation of 1-(4-bromo-2-methylphenylaminocarbonyl)cyclobutanecarboxylic acid A 3.0 gram (0.009 mole) portion of ethyl 1-(4-bromo-2-methylphenylaminocarbonyl)cyclobutanecarboxylate prepared in Example IX (Compound 129) was hydrolyzed in a manner similar to that described in Example XI to give 2.19 grams (0.007 mole) of 1-(4-bromo-2-methylphenylaminocarbonyl)cyclobutanecarboxylic acid having a melting point of 154° C.-155° C. NMR analysis of the product indicated the following:

NMR(DMSO-d$_6$/CDCl$_3$): δ1.7-2.8 (m, 10H), 7.45 (s,3H aromatic), 9.25 (s,H exch.) ppm.

This compound is referred to hereinafter as Compound 181.

EXAMPLE XXXIII

Preparation of ethyl 1-(4-chloro-2-ethylphenylaminocarbonyl)cyclopropanecarboxylate To a stirred solution of 1.54 grams (0.01 mole) of 1-carboethoxycyclopropanecarboxylic acid (the monocarboxylic acid intermediate described in Example XVIII) and 0.99 gram (0.01 mole) of triethylamine in 75 milliliters of acetonitrile was added a solution of 1.06 grams (0.01 mole) of ethyl chloroformate in 25 milliliters of acetonitrile dropwise with cooling to 0° C.-5° C. After stirring at ice temperature for 30 minutes a solution of 1.52 grams (0.01 mole) of 4-chloro-2-ethylaniline in 20 milliliters of acetonitrile was fed dropwise with stirring and continued cooling. The reaction mixture was allowed to warm to room temperature, then stirred for approximately sixteen hours following which it was filtered and the filtrate freed of solvent by evaporation. The residue was dissolved in dichloromethane and extracted, successively, with water (2×50 milliliters), 2N HCl (2×50 milliliters) and water (1×50 milliliters). After drying (MgSO$_4$), solvent was removed by evaporation and the solid recrystallized from hexane to give 1.15 grams (0.004 mole) of ethyl 1-(4-chloro-2-ethylphenylaminocarbonyl)cyclopropanecarboxylate as cream colored prisms having a melting point of 77° C.-80° C.

Elemental analysis of the product indicated the following: Analysis: C$_{15}$H$_{18}$ClNO$_3$; Calculated: C, 60.91; H, 6.13. Found: C, 61.38; H, 6.13.

This compound is referred to hereinafter as Compound 182.

EXAMPLE XXIV

Preparation of 1-(4-chloro-2-ethylphenylaminocarbonyl)cyclopropanecarboxylic acid A 1.74 gram (0.006 mole) portion of ethyl 1-(4-chloro-2-ethylphenylaminocarbonyl)cyclopropanecarboxylate prepared in Example XXXIII (Compound 182) was hydrolyzed in a manner similar to that described in Example VII to give 0.55 gram (0.002 mole) of 1-(4-chloro-2-ethylphenylaminocarbonyl)cyclopropanecarboxylic acid having a melting point of 178.5° C.-181° C. NMR analysis of the product indicated the following:

NMR (DMSO-d$_6$/CDCl$_3$): $\delta$1.07–1.34 (t,3H), 1.62 (s,4H), 2.38–2.89 (q,2H), 7.07–8.19 (m,3H), 11.37 (s,H) ppm.

This compound is referred to hereinafter as Compound 183.

EXAMPLE XXXV

Preparation of ethyl 1-[N-(4-chlorophenyl)-N-methylaminocarbonyl]cyclopropanecarboxylate 1-Carboethoxycyclopropanecarboxylic acid (5.54 grams, 0.035 mole), ethyl chloroformate (3.80 grams, 0.035 mole) and 4-chloro-N-methylaniline (4.96 grams, 0.035 mole) were reacted sequentially in the presence of triethylamine (3.54 grams, 0.035 mole) in a manner similar to that described in Example XXXIII to give 2.26 grams (0.008 mole) of ethyl 1-[N-(4-chlorophenyl)-N-methylaminocarbonyl]cyclopropanecarboxylate having a melting point of 53° C.–56.5° C. NMR analysis of the product indicated the following:

NMR (CDCl$_3$): $\delta$1.0–1.46 (m,7H), 3.35 (s,3H), 3.7–4.2 (m,2H), 7.0–7.47 (m,4H) ppm.

This compound is referred to hereinafter as Compound 184.

EXAMPLE XXXVI

Preparation of 1-[N-(4-chlorophenyl)-N-methylaminocarbonyl]cyclopropanecarboxylic acid A 3.0 gram (0.01 mole) portion of ethyl 1-(4-chlorophenyl-N-methylaminophenylcarbonyl)cyclopropanecarboxylate prepared in Example XXXV (Compound 184) was hydrolyzed in a manner similar to that described in Example VII to give 0.9 gram (0.003 mole) of 1-[N-(4-chlorophenyl)-N-methylaminocarbonyl]cyclopropanecarboxylic acid. Recrystallization from ethyl acetate gave an analytically pure sample having a melting point of 156° C.–158° C.

Elemental analysis of the product indicated the following: Analysis: C$_{12}$H$_{12}$ClNO$_3$; Calculated: C, 56.81; H, 4.77. Found: C, 56.91; H, 4.72.

This compound is referred to hereinafter as Compound 185.

EXAMPLE XXXVII

Preparation of 1-(phenylaminocarbonyl)cyclopropanecarboxylic acid

1-Carboethoxycyclopropanecarboxylic acid (3.95 grams, 0.025 mole), ethyl chloroformate (2.71 grams, 0.025 mole) and aniline (2.33 grams, 0.025 mole) were reacted sequentially in the presence of triethylamine (2.53 grams, 0.025 mole) in a manner similar to that described for ethyl 1-(4-chloro-2-ethylphenylaminocarbonyl)cyclopropanecarboxylate in Example XXXIII to give ethyl 1-(phenylaminocarbonyl)cyclopropanecarboxylate which was then hydrolyzed in a manner similar to that described in Example VII to give 2.42 grams (0.01 mole) of 1-(phenylaminocarbonyl)cyclopropanecarboxylic acid having a melting point of 178° C.–181° C. NMR analysis of the product indicated the following:

NMR (DMSO-d$_6$/CDCl$_3$): $\delta$1.65 (s,4H), 7.0–7.87 (m,6H aromatic plus NH), 10.95 (s,H) ppm.

This compound is referred to hereinafter as Compound 186.

EXAMPLE XXXVIII

Preparation of ethyl 3-[(3,4-dichlorophenyl)thio]-3-oxopropanoate 3,4-Dichlorothiophenol (3.67 grams, 0.02 mole) and ethyl malonyl chloride (3.08 grams, 0.02 mole) were reacted in the presence of triethylamine (2.07 grams, 0.02 mole) in a manner similar to that described in Example 1 to give 3.63 grams (0.012 mole) of ethyl 3-[(3,4-dichlorophenyl)thio]-3-oxopropanoate as a liquid, recovered and purified by flash column chromatography. NMR analysis of the product indicated the following:

NMR (CDCl$_3$): $\delta$1.19–1.44 (t,3H), 3.66 (s,2H), 4.05–4.44 (q,2H), 7.15–7.63 (m,3H) ppm.

This compound is referred to hereinafter as Compound 187.

EXAMPLE XXXIX

Preparation of ethyl 3-[(2,4,5-trichlorophenyl)thio]-3-oxopropanoate 2,4,5-Trichlorothiophenol (3.91 grams, 0.02 mole) and ethyl malonyl chloride (2.76 grams, 0.02 mole) were reacted in the presence of triethylamine (1.85 grams, 0.02 mole) in a manner similar to that described in Example I to give 2.29 grams (0.007 mole) of ethyl 3-[(2,4,5-trichlorophenyl)thio]-3-oxopropanoate having a melting point of 41° C.–43° C.

Elemental analysis of the product indicated the following: Analysis: C$_{11}$H$_9$Cl$_3$O$_3$S; Calculated: C, 40.33; H, 2.77. Found: C, 40.59; H, 2.99.

This compound is referred to hereinafter as Compound 188.

EXAMPLE XL

Preparation of S-phenyl 3-[(4-bromo-2-methylphenyl)amino]-3-oxopropanethioate

To a stirred mixture of 5.44 grams (0.02 mole) of 3-[(4-bromo-2-emthylphenyl)amino]-3-oxopropanoic acid prepared in Example V (Compound No. 97) and 2.31 grams (0.02 mole) of thiophenol in approximately 100 milliliters of dry tetrahydrofuran in an oven-dried reaction flask was fed a solution of 4.13 grams (0.02 mole) of 1,3-dicyclohexylcarbodiimide in about 25 milliliters of dry tetrahydrofuran, while cooling the reaction mixture in an ice-water bath. On completing the feed the ice bath was removed and the mixture stirred for about one hour following which the precipitated 1,3-dicyclohexylurea by-product (2.5 grams) was removed by filtration. Vacuum stripping the filtrate gave a solid which was recrystallized from acetone to give a compound, melting point 184° C.–187° C., which proved to be 1-(3-[(4-bromo-2-methylphenyl)amino]-3-oxopropanoyl)-1,3-dicyclohexylurea. The filtrate from this was concentrated and flash chromatographed (7:3 hexane:ethylacetate, silica column) to give 2.83 grams (0.008 mole) of S-phenyl 3-[(4-bromo-2-methylphenyl)amino]-3-oxopropanethioate having a melting point of 133° C.–135° C.

Elemental analysis of the product indicated the following: Analysis: C$_{16}$H$_{14}$BrCO$_2$S; Calculated: C, 52.75; H, 3.87. Found: C, 52.73; H, 3.98.

This compound is referred to hereinafter as Compound 189.

EXAMPLE XLI

In a manner similar to that employed in Example XL, other compounds were prepared. The structures and analytical data for Compounds 190 through 196 are set forth in Table I below.

N-(2-hydroxyethyl)-3-[N'-(4-bromo-2-methylphenyl)amino]-3-oxopropanamide having a melting point of 139° C.–142° C.

Elemental analysis of the product indicated the following: Analysis: $C_{12}H_{15}BrN_2O_4$; Calculated: C, 43.52; H, 4.57. Found: C, 45.76; H, 4.76.

This compound is referred to hereinafter as Compound 198.

TABLE I
Representative Malonic Acid Derivative Compounds

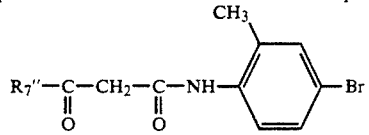

| Compound No. | Substituent $R_7''$ | Elemental Analysis Calculated C | H | N | Found C | H | N | Melting Point °C. |
|---|---|---|---|---|---|---|---|---|
| 190 | $OCH(CH_3)CO_2C_2H_5$ | NMR(CDCl$_3$): δ 1.0–1.68(m, 6H), 2.25(s, 3H), 3.60(s, 2H), 4.0–4.44(q, 2H, 4.96–5.40(q, H), 7.14–7.95(m, 3H), 8.96–9.27(br s, H)ppm. | | | | | | 72–79 |
| 191 | $OCH_2COCH_3$ | 47.58 | 4.30 | — | 47.49 | 4.32 | — | 127–128 |
| 192 | $OCH(CH_3)CN$ | 48.02 | 4.03 | — | 47.86 | 4.03 | — | 83–86 |
| 193 | $SCH_2CO_2C_2H_5$ | NMR(CDCl$_3$): δ 1.08–1.46(t, 3H), 2.23(s, 3H), 3.81(s, 4H), 3.98–4.45(q, 2H), 7.15–7.91(m, 3H), 8.6(br s, H)ppm. | | | | | | 109–111.5 |
| 194 | $OCH_2CH_2SO_2C_2H_5$ | 42.86 | 4.59 | — | 43.91 | 4.87 | — | 111–113 |
| 195 | $ON=C(CH_3)SCH_3$ | 43.46 | 4.21 | — | 45.08 | 4.73 | — | 149–152 |
| 196 | $OCH_3$ | 46.17 | 4.23 | — | 46.60 | 4.46 | — | 108–110 |

EXAMPLE XLII

Preparation of methyl 1-(4-bromo-2-methylphenylaminocarbonyl)cyclopropanecarboxylate A 4.00 gram (0.01 mole) portion of 1-(4-bromo-2-methylphenylaminocarbonyl)cyclopropanecarboxylic acid prepared in Example VIII (Compound 111) was recited in sequence with 80 milliliters of methanol (excess as solvent) and 2.77 grams (0.01 mole) of 1,3-dicyclohexylcarbodiimide, employing a 16-hour reaction period, in a manner similar to that described in Example XL to give 1.54 grams (0.005 mole) of methyl 1-(4-bromo-2-methylphenylaminocarbonyl)cyclopropanecarboxylate as a white powder having a melting point of 106° C.–108° C.

Elemental analysis of the product indicated the following: Analysis: $C_{13}H_{14}BrNO_3$; Calculated: C, 50.02; N, 4.52. Found: C, 50.34; H, 4.64.

This compound is referred to hereinafter as Compound 197.

EXAMPLE XLIII

Preparation of N-(2-hydroxyethyl)-3-[N'-(4-bromo-2-methylphenyl)amino]-3-oxopropanamide A mixture of 6.0 grams (0.02 mole) of ethyl 3-[(4-bromo-2-methylphenyl)amino]-3-oxopropanoate, 366.5 grams (6.0 moles) of ethanolamine and 150 milliliters of ethyl alcohol, containing 5 drops of added water, was stirred for a period of approximately 70 hours at room temperature. It was then evaporated under reduced pressure to remove all solvent and unreacted excess ethanolamine. The residue was flash chromatographed on silica using 100% acetone as the eluent and the fractions with a single $R_f$=0.66 spot (silica plate TLC, 100% acetone) evaporated to give 4.86 grams of a tan solid. A 2.0 gram portion of the latter was recrystallized from acetone-hexane to give 1.5 grams (0.004 mole) of

EXAMPLE XLIV

Preparation of ethyl 1-(2,4-difluorophenylaminocarbonyl)cyclopropanecarboxylate

1-Carboethoxycyclopropanecarboxylic acid 7.00 grams, 0.04 mole), ethyl chloroformate (4.8) grams, 0.04 mole) and 2.4-difluoroaniline (5.72 grams, 0.04 mole) were reacted sequentially in the presence of triethylamine (4.51 grams, 0.04 mole) in a manner similar to that described in Example XXXIII to give 7.13 grams (0.03 mole) of ethyl 1-(2,4-difluorophenylaminocarbonyl)cyclopropanecarboxylate as a white crystalline solid having a melting point of 79° C.–80.5° C.

Elemental analysis of the product indicated the following: Analysis: $C_{13}H_{13}F_2NO_3$; Calculated: C, 57.99; H, 4.87. Found: C, 58.36; H, 5.17.

This compound is referred to hereinafter as Compound 199.

EXAMPLE XLV

Preparation of ethyl 3-[(4-bromo-2-methylphenyl)amino]-2-nitro-3-oxopropanoate

A mixture of 9.22 grams (0.04 mole) of 4-bromo-2-methylphenyl isocyanate, 5.78 grams (0.04 mole) of ethyl nitroacetate, 6.01 grams (0.04 mole) of anhydrous potassium carbonate and 90 milliliters of benzene was stirred and heated under reflux for 3 hours then cooled and stirred at room temperature for a period of about 16 hours. The precipitated material was filtered off and thoroughly triturated with 200 milliliters of ice water, filtering to remove a precipitate which was discarded. Chilling and acidification of the filtrate with concentrated HCl caused precipitation of a yellow-white solid which was collected, water-washed and air-dried. Recrystallization from benzene-cyclohexane (3:1) gave 3.38 grams (0.01 mole) of ethyl 3-[(4-bromo-2-methylphenyl)amino]-2-nitro-3-oxopropanoate as white crystals having a melting point of 126° C.-129° C.

Elemental analysis of the product indicated the following: Analysis: $C_{12}H_{13}BrN_2O_5$; Calculated: C,41.76; H, 3.80. Found: C, 41.94; H, 3.86.

This compound is referred to hereinafter as Compound 200.

EXAMPLE XLVI

In a manner similar to that employed in Example XLV, other compounds were prepared. The structures and analytical data for Compounds 201 through 204 are set forth in Table J below.

filtered off and the filtrate vacuum evaporated to give a yellow solid. The latter was digested with cold 2N HCl to remove unreacted starting material and the undissolved solid was collected and recrystallized from methanol. Vacuum drying of the resulting solid gave 2.73 grams (0.008 mole) of ethyl 3-[(4-chlorophenyl)amino]-2-(dimethyloxosulfuranylidene)-3-oxopropanoate having a melting point of 162° C.-163° C.

Elemental analysis of the product indicated the following: Analysis: $C_{13}H_{16}ClNO_4S$; Calculated: C, 49.13; H, 5.08; N, 4.41. Found: C, 48.99; H, 5.00; N, 4.30.

This compound is referred to hereinafter as Compound 205.

TABLE J
Representative Malonic Acid Derivative Compounds

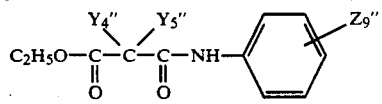

| Compound No. | Substituent | | | Elemental Analysis | | | | | | Melting Point °C. |
| --- | --- | --- | --- | --- | --- | --- | --- | --- | --- | --- |
| | $Y_4''$ | $Y_5''$ | $Z_9''$ | Calculated | | | Found | | | |
| | | | | C | H | N | C | H | N | |
| 201 | $NO_2$ | H | 3,4-$Cl_2$ | 41.14 | 3.14 | — | 41.49 | 3.21 | — | 107–109 |
| 202 | CN | H | 2-$CH_3$-4-Br | 48.02 | 4.03 | — | 47.99 | 4.16 | — | 153–155 |
| 203 | $CH_3SO_2$ | H | 2-$CH_3$-4-Br | 41.28 | 4.26 | — | 40.93 | 4.28 | — | 153–155 |
| 204 | $CH_3CO$ | H | 2-$CH_3$-4-Br | 49.14 | 4.71 | 4.09 | 49.09 | 4.86 | 3.83 | 101–103.5 |

EXAMPLE XLVII

Preparation of ethyl 3-[(4-chlorophenyl)amino]-2-(dimethyloxosulfuranylidene)-3-oxopropanoate Part A: Preparation of N-(4-chlorophenyl)-2-(dimethyloxosulfuranylidene)acetamide A solution of 22.0 grams (0.10 mole) of trimethylsulfoxonium iodide in 150 milliliters of dimethylsulfoxide was stirred, with cooling at 20° C., while 4.0 grams (0.10 mole) of 60% sodium hydride were added to the mixture in portions. Stirring was continued until hydrogen evolution was complete and a solution of 15.36 grams (0.10 mole) of 4-chlorophenyl isocyanate then added over a 30 minute period. After stirring for about 2.5 hours the reaction mixture was poured into 200 milliliters of ice water causing precipitation of a white solid. The latter was air dried and then extracted repeatedly with benzene followed by hot ethanol. The solid remaining undissolved following the third ethanol wash was washed with chloroform giving 6.72 grams (0.03 mole) of N-(chlorophenyl)-2-(dimethyloxosulfuranylidene)acetamide as the insoluble residue. Similar chloroform extractions of two crops of solid which separated from the final ethanol extract afforded an additional 1.58 grams (0.01 mole) of N-(4-chlorophenyl)-2-(dimethyloxosulfuranylidene)acetamide as the insoluble residue.

Part B: Preparation of ethyl 3-[(4-chlorophenyl)amino]-2-(dimethyloxosulfuranylidene)-3-oxopropanoate To a stirred solution of 7.72 grams (0.03 mole) of N-(4-chlorophenyl)-2-(dimethyloxosulfuranylidene)acetamide prepared in Part A of this Example, in 80 milliliters of anhydrous acetonitrile, was added 1.70 grams (0.02 mole) of ethyl chloroformate dropwise at room temperature and the resulting mixture then heated and stirred at 50° C. for an approximate 16-hour period. The hydrochloride by-product was

EXAMPLE XLVIII

Preparation of ethyl 3-[(4-chlorophenyl)amino]-2-bromo-3-oxopropanoate

To a stirred solution of 2.73 grams (0.01 mole) of ethyl 3-[(4-chlorophenyl)amino]-2-(dimethyloxosulfuranylidene)-3-oxopropanoate prepared in Example XLVII (Compound 205) in 35 milliliters of chloroform was added a solution of 1.37 grams (0.01 mole) of bromine in 35 milliliters of chloroform, dropwise, at ambient temperature. The mixture became dark orange and showed a slight exothermic effect during the feed period. Stirring was continued for 20 minutes, at which time the solution was a clear light yellow in color. It was then evaporated free of solvent and stored at 5° C. for a period of about 64 hours causing the residue to crystallize. Two recrystallizations from hexane-ethyl acetate (10:1) gave 0.58 gram (0.002 mole) of ethyl 3-[(4-chlorophenyl)amino]-2-bromo-3-oxopropanoate having a melting point of 117° C.-119° C.

Elemental analysis of the product indicated the following: Analysis: $C_{11}H_{11}BrClNO_3$; Calculated: C, 41.21; H, 3.46; n, 4.37; O, 14.97; Cl, 11.06; Br, 24.93. Found: C, 41.24; H, 3.59; N, 4.32; O,15.33; Cl, 11.08; Br, 24.60.

This compound is referred to hereinafter as Compound 206.

EXAMPLE XLIX

Preparation of ethyl 3-[(4-chlorophenyl)amino]-2-chloro-3-oxopropanoate

A solution of 1.5 grams (0.05 mole) of ethyl 3-[(4-chlorophenyl)amino]-2-(dimethyloxosulfuranylidene)-3-oxopropanoate prepared in Example XLXII (Compound 205) in 25 milliliters of chloroform was stirred at room temperature for two hours while passing in a flow of anhydrous hydrogen chloride. After ceasing the gas feed the solution was stirred at ambient temperature for about 64 hours after which the solvent was removed under reduced pressure. Flash chromatography of the residue eluting with hexane-ethyl acetate (7:3), gave a white solid which was recrystallized from ethyl acetate-hexane to give 0.20 gram (0.001 mole) of ethyl 3-[(4-chlorophenyl)amino]-2-chloro-3-oxopropanoate having a melting point of 104° C.–105° C.

Elemental analysis of the product indicated the following: Analysis: $C_{11}H_{11}Cl_2NO_3$; Calculated: C, 47.85; H, 4.02; N, 5.07. Found: C, 48.08; H, 4.23; N, 5.17.

This compound is referred to hereinafter as Compound 207.

EXAMPLE L

Preparation of ethyl 3-[(4-bromo-2-methylphenyl)amino]-2-(dimethylaminomethylene)-3-oxopropanoate A mixture of 21.12 grams (0.07 mole) of ethyl 3-[(4-bromo-2-methylphenyl)amino]-3-oxopropanoate, 12.58 grams (0.11 mole) of N,N-dimethylformamide dimethyl acetal and 900 milliliters of cyclohexane was heated under reflux for a period of thirty two minutes at which time TLC indicated the reaction to be incomplete. Another 12.58-gram (0.11 mole) portion of the acetal was then added and the reaction mixture stirred overnight at ambient temperature. Solvent was stripped from the mixture under reduced pressure and the resulting solid then crystallized from hexane-ethyl acetate (10:1) to give 12.6 grams (0.035 mole) of ethyl 3-[(4-bromo-2-methylphenyl)amino]-2-(dimethylaminomethylene)-3-oxopropanoate having a melting point of 88° C.–90° C.

Elemental analysis of the product indicated the following: Analysis: $C_{15}N_{19}BrN_2O_3$; Calculated: C, 50.72; H, 5.39; N, 7.89. Found: C, 50.79; H, 5.62; N, 7.78.

This compound is referred to hereinafter as Compound 208.

EXAMPLE LI

Preparation of ethyl 3-[(4-bromo-2-methylphenyl)amino]-2-(dimethylsulfuranylidene)-3-oxopropanoate A mixture of 30.0 grams (0.10 mole) of ethyl 3-[(4-bromo-2-methylphenyl)amino]-3-oxopropanoate, 51.58 grams (0.25 mole) of 1,3-dicyclohexylcarbodiimide, 100 milliliters of benzene and 100 milliliters of dimethyl sulfoxide was stirred at ambient temperature and a solution of 4.9 grams (0.05 mole) of anhydrous phosphoric acid in 10 milliliters of dimethyl sulfoxide added dropwise. After a few minutes an exothermic reaction occurred with separation of a white solid and an increase in temperature from 25° C. to 35° C. The reaction mixture was then stirred for an approximate 16-hour period at ambient temperature. The mixture was then diluted with 500 milliliters of ethyl acetate and by-product 1,3-dicyclohexylurea removed by filtration. The filtrate was washed with several portions of water, dried over $MgSO_4$, filtered and freed of solvent under reduced pressure to give a yellow solid. This was crystallized from ethyl acetate-hexane (1:1) to give 15.8 grams (0.04 mole) of ethyl 3-[(4-bromo-2-methylphenyl)amino]-2-(dimethylsulfuranylidene)-3-oxopropanoate having a melting point of 143° C.–150° C. Recrystallization of a small sample gave a white solid of melting point 146° C.–149° C.

Elemental analysis of the product indicated the following: Analysis: $C_{14}N_{18}BrNO_3S$; Calculated: C, 46.67; H, 5.04; Found: C, 47.38; H, 5.36.

This compound is referred to hereinafter as Compound 209.

EXAMPLE LII

Preparation of ethyl 3-[(4-chlorophenyl)amino]-2-methyl-2-nitro-3-oxopropanoate

Part A: Preparation of diethyl methyl(nitro)malonate

A solution of 10.1 grams (0.06 mole) of diethyl nitromalonate in 150 milliliters of anhydrous N,N-dimethylformamide was stirred and cooled at 0° C.–5° C. while adding 2.38 grams (0.06 mole) of 60% sodium hydride in small portions. Stirring at 0° C.–5° C. was continued until hydrogen evolution had ceased and 16.95 grams (0.12 mole) of methyl iodide were then added to the reaction mixture dropwise along with two drops of 15-crown-5. The ice bath was then removed and the reaction flask covered with aluminum foil and the system allowed to stir for about 16 hours at room temperature. The solvent was removed under reduced pressure and the residue partitioned between water and ethyl ether, separating the ether layer and drying it over $MgSO_4$. Evaporation of ether gave 9.36 g (0.04 mole) of diethyl methyl(nitro) malonate. NMR analysis of the product indicated the following:

$^1$H NMR ($CDCl_3$): $\delta$1.13–1.48 (t,6H,2×$CH_3$), 2.04(s, 3H, $CH_3C$—$NO_2$), 4.16–4.58 (q, 4H, 2×$CH_2$) ppm.

Part B: Preparation of ethyl 2-nitropropionate potassium Salt

A mixture of 2.4 grams (0.04 mole) of potassium hydroxide, 100 milliliters of ethanol and 0.77 gram (0.04 mole) of water was stirred at 0° C.–5° C. until solution was complete. A 9.36-gram (0.04 mole) portion of diethyl 2-methyl-2-nitromalonate was then added dropwise with stirring and the reaction mixture was allowed to stir at room temperature for a period of about 16 hours. Volatiles were removed from the mixture under reduced pressure and the last traces of water were eliminated by azeotropic distillation with toluene to give 7.96 grams (0.04 mole) of ethyl 2-nitropropionate potassium salt. NMR analysis of the product indicated the following:

$^1$H NMR ($D_2O$): $\delta$1.12–1.48(t, 3H, $CH_3$), 2.13(s, 3H, $CH_3$), 4.08–4.51 (q, 2H, $CH_2$) ppm.

Part C: Preparation of ethyl 3-[(4-chlorophenyl)amino]-2-methyl-2-nitro-3-oxopropanoate Anhydrous HCl gas was bubbled into a stirred solution of 5.0 grams (0.03 mole) of 4-chlorophenyl isocyanate in 150 milliliters of benzene-hexane (2:1), for a 30-minute period, at room temperature. Stirring of the mixture was continued for a period of approximately 80 hours, until infrared spectral examination of stripped reaction mixture aliquots showed near complete replacement of the NCO carbonyl stretching at 2295 cm$^{-1}$ by a band at 1775 cm$^{-1}$ attributable to the carbamoyl chloride function. Vacuum evaporation of solvents left a white solid residue of N-(4-chlorophenyl)-carbamoyl chloride, which was employed in the ensuing step without purification.

A solution of 7.96 grams (0.04 mole) of ethyl 3-nitropropionate potassium salt (from Part B, above) and 0.01 gram of 18-Crown-6 in 75 milliliters of N,N-dimethylformamide was prepared and to this was added, in one portion, a solution of the above N-(4-chlorophenyl)carbamoyl chloride in 75 milliliters of N,N-dimethylformamide. The resulting mixture was stirred at room temperature for about 20 hours and then at 60° C. for an approximate 17-hour period after which the solvent was removed by vacuum evaporation. The residue was partitioned between ethyl ether and KCl-saturated water and the ether phase separated, dried over MgSO$_4$ and evaporated free of solvent. Flash-column chromatography of the residue, eluting with 7:3 hexane-ethyl acetate, gave a liquid fraction of R$_F$0.48 which was further purified by preparative plate chromatography to give 0.06 gram (0.0002 mole) of ethyl 3-[(chlorophenyl)amino]-2-methyl-2-nitro-3-oxopropanoate as an oil.

Elemental analysis of the product indicated the following: Analysis: $C_{12}H_{13}ClN_2OS$; Calculated: C, 47.93; H, 4.36; N, 9.32. Found: C, 47.53; H, 4.48; N, 9.32.

This compound is referred to hereinafter as Compound 210.

EXAMPLE LIII

Preparation of ethyl (chlorocarbonyl)methoxyacetate

Part A: Preparation of diethyl methoxymalonate

A mixture of 50.4 grams (0.3 mole) of dimethyl methoxymalonate, para-toluenesulfonic acid (2.76 grams) and 300 milliliters of ethanol was heated under reflux for a period of about 24 hours. Volatile materials were then removed under reduced pressure, employing a water bath at about 25° C. A second 300 milliliter-portion of ethanol was added and the mixture then refluxed for about 5 hours after which it was stirred at room temperature for an approximate 64-hour period. Removal of ethanol from the mixture under reduced pressure gave 61.0 grams (0.3 mole) of diethyl methoxymalonate, employed in the subsequent steps without purification.

Part B: Preparation of mono-ethyl methoxymalonate

A mixture of 30.0 grams (0.2 mole) of diethyl methoxymalonate (Part A, above), 8.85 grams (0.2 mole) of potassium hydroxide, 2.84 grams (0.2 mole) of water and 300 milliliters of ethanol was stirred at room temperature for about 72 hours and volatiles then removed under reduced pressure. The residue was dissolved in water and the pH of the solution adjusted to 10 by addition of potassium hydroxide. The solution was saturated with potassium chloride and extracted with methylene chloride (3×100 milliliters) to remove unsaponified diester. Acidification to pH=1 and continuous extraction with methylene chloride afforded 9.45 grams (0.06 mole) of mono-ethyl methoxymalonate as a liquid.

Part C: Preparation of ethyl (chlorocarbonyl) methoxyacetate

A mixture of 5.88 grams (0.04 mole) of mono-ethyl methoxymalonate from Part B, above 8.63 grams (0.07 mole) of thionyl chloride and 150 milliliters of methylene chloride was stirred for about 17 hours and then evaporated free of volatile materials. As NMR examination indicated the reaction to be incomplete, the above thionyl chloride treatment in methylene chloride was repeated for a period of about 65 hours. A third treatment with 8.63 grams of thionyl chloride in 150 milliliters of methylene chloride was finally given, refluxing for a period of approximately 7 hours. Removal of volatiles under reduced pressure gave 6.0 grams (0.03 mole) of ethyl (chlorocarbonyl) methoxyacetate. NMR analysis of the product indicated the following:

'H NMR (CDCl$_3$): δ1.16–1.53(t, 3H, CH$_3$), 3.58(s, 3H, CH$_3$O), 4.14–4.56 (q, 2H, CH$_2$) 4.62 (s, H, CH) ppm.

This compound is referred to hereinafter as Compound 211.

EXAMPLE LIV

Preparation of ethyl 3-[(4-bromo-2-methylphenyl)amino]-2-methoxy-3-oxopropanoate 4-Bromo-2-methylaniline (3.09 grams, 0.02 mole) and ethyl (chlorocarbonyl)methoxyacetate (3.0 grams, 0.02 mole), prepared in Example LIII (Compound 211), were reacted in the presence of triethylamine (1.68 grams, 0.02 mole) in 200 milliliters of methylene chloride in a manner similar to that described in Example I to give 2.04 grams (0.01 mole) of ethyl 3-[(4-bromo-2-methylphenyl)amino]-2-methoxy-3-oxopropanoate having a melting point of 93° C.-95° C.

Elemental analysis of the product indicated the following: Analysis: $C_{13}H_{16}BrNO_4$; Calculated: C, 47.29; H, 4.88; N, 4.24. Found: C, 47.38; H, 5.14; N, 3.85.

This compound is referred to hereinafter as Compound 212.

EXAMPLE LV

Preparation of ethyl 3-[(3,5-dichlorophenyl)amino]-2-methoxy-3-oxopropanoate 3,5-Dichloroaniline (2.69 grams, 0.02 mole) and ethyl (chlorocarbonyl)methoxyacetate (3.0 grams, 0.02 mole), prepared in Example LIII (Compound 211), were reacted in the presence of triethylamine (1.68 grams, 0.02 mole) in 200 milliliters of methylene chloride in a manner similar to that described in Example I to give 1.34 grams (0.004 mole) of ethyl 3-[(3,5-dichlorophenyl)amino]-2-methoxy-3-oxopropanoate having a melting point of 89.5° C.-92.5° C.

Elemental analysis of the product indicated the following: Analysis: $C_{12}H_{13}Cl_2NO_4$; Calculated: C, 47.08; H, 4.28; N, 4.58. Found: C, 47.41; H, 4.41; N, 4.20.

This compound is referred to hereinafter as Compound 213.

EXAMPLE LVI

Preparation of mono-methyl methoxymalonate

Dimethyl methoxymalonate (50.0 grams, 0.3 mole) was saponified with potassium hydroxide (17.3 grams, 0.3 mole) in a mixture of 500 milliliters of methanol and 5.55 grams (0.3 mole) of water according to the general procedure of Example VII but employing a reaction period of approximately 16 hours. The reaction mixture was evaporated free of solvents and the residue dissolved in water and extracted twice with ether to remove any unreacted diester. The aqueous layer was then saturated with potassium chloride, acidified with 2H HCl and extracted twice with ethyl ether. As this procedure enabled recovery of only a minor amount of product the aqueous phase was then subjected to three 16-hour periods of continuous liquid-liquid extraction with methylene chloride, adjusting the pH from 4 to 1 at the beginning of the second extraction period. Workup of the combined extracts gave 29.24 grams (0.2 mole) of mono-methyl methoxymalonate. NMR analysis of the product indicated the following:

'H NMR (CDCl$_3$): δ3.54(s, 3H, alpha CH$_3$O), 3.86(s, 3H, ester CH$_3$O), 4.51 (s, H, CH), 9.36(s, H, CO$_2$H) ppm.

This compound is referred to hereinafter as Compound 214.

EXAMPLE LVII

Preparation of methyl 3-[(4-bromo-2-fluorophenyl)amino]-2-methoxy-3-oxopropanoate To a stirred mixture of 2.78 grams (0.02 mole) of mono-methyl methoxymalonate prepared in Example LVI (Compound 214) and 3.56 grams (0.02 mole) of 4-bromo-2-fluoroaniline in approximately 100 milliliters of dry tetrahydrofuran was fed dropwise a solution of 3.87 grams (0.02 mole) of 1,3-dicyclohexylcarbodiimide in about 30 milliliters of dry tetrahydrofuran, while cooling the reaction mixture in an ice-water bath. The reaction mixture was allowed to warm slowly to room temperature and stirring continued for an approximate 65-hour period. The precipitated 1,3-dicyclohexylurea by-product (3.15 grams) was removed by filtration and the filtrate vacuum evaporated and the residue dissolved in methylene chloride. The latter solution was extracted with dilute HCl and then water, then dried ($MgSO_4$) and solvent vacuum evaporated to give a colorless liquid. Flash column chromatography of the latter on silica, eluting with hexane-ethyl acetate (7:3) gave, after workup, a liquid which crystallized on standing. Recrystallization from hexane containing a small amount of ethyl acetate gave 2.3 grams (0.01 mole) of methyl 3-[(4-bromo-2-fluorophenyl)amino]-2-methoxy-3-oxopropanaote having a melting point of 51° C.-53° C.

Elemental analysis of the product indicated the following: Analysis: $C_{11}H_{11}BrFNO_4$; Calculated: C, 41.27; H, 3.47; N, 4.38. Found: C, 41.38; H, 3.93; N, 3.70.

This compound is referred to hereinafter as Compound 215.

EXAMPLE LVIII

In a manner similar to that employed in Example LVII, other compounds were prepared. The structures and analytical data for Compounds 216 through 219 are set forth in Table K below.

0.1 mole) in a mixture of 250 milliliters of ethanol and 2.18 grams (0.01 mole) of water according to the general procedure of Example VII but employing a reaction time of 2 hours and holding the saponification temperature at 0° C.-5° C. The reaction mixture was evaporated free of solvents and the residue dissolved in water and extracted twice with methylene chloride. The aqueous phase was cooled to 0° C.-5° C., acidified to pH=1 with cold 2N HCl, saturated with potassium chloride and extracted three times with methylene chloride. The aqueous phase was reacidifed with HCl and extracted twice with 3:1 chloroform-ethyl acetate. The organic extract were dried ($MgSO_4$), filtered, and the filtrates evaporated free of solvents to give a total of 9.51 grams (0.05 mole) of mono-ethyl methylthiomalonate. NMR analysis of the product indicated the following:

$^1$H NMR ($CDCl_3$) δ1.15–1.50(t, 3H, $CH_3$), 2.31(s, 3H, $CH_3S$), 4.10–4.50(s and q, 3H, CH and $CH_2$), 8.8–9.25 (broad, H exch.).

This compound is referred to hereinafter as Compound 220.

EXAMPLE LX

Preparation of ethyl 3-[(4-bromo-2-methylphenyl)amino]-2-(methylthio)-3-oxopropanoate Mono-ethyl methylthiomalonate (5.05 grams, 0.03 mole), prepared in example LIX (Compound 220), 4-bromo-2-methylaniline (5.27 grams, 0.03 mole) and 1,3-dicyclohexylcarbodiimide (5.85 grams, 0.03 mole) were reacted in a manner similar to that described in Example LVII to give 0.95 gram (0.003 mole) of ethyl 3-[(4-bromo-2-methylphenyl)amino]-2-(methylthio)-3-oxopropanoate having a melting point of 85° C.-88° C.

Elemental analysis of the product indicated the following: Analysis: $C_{13}H_{16}BrNO_3S$; Calculated: C, 45.09; H, 4.66; N, 4.05; Found: C, 45.41; H, 4.81; N, 4.32.

This compound is referred to hereinafter as Compound 221.

TABLE K

Representative Malonic Acid Derivative Compounds

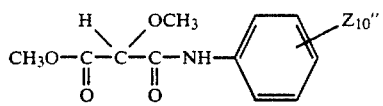

| Compound No. | Substituent $Z_{10}''$ | Elemental Analysis | | | | | | Melting Point °C. |
|---|---|---|---|---|---|---|---|---|
| | | Calculated | | | Found | | | |
| | | C | H | N | C | H | N | |
| 216 | 3,4-$Cl_2$ | 45.23 | 3.45 | 4.80 | 45.21 | 3.91 | 4.20 | 78–81 |
| 217 | 4-$CF_3$ | 49.49 | 4.15 | 4.81 | 49.88 | 4.29 | 4.91 | 101–103 |
| 218 | 4-Br | 43.73 | 4.00 | — | 43.73 | 4.04 | — | 55–59 |
| 219 | 3,4,5-$Cl_3$ | 40.46 | 3.09 | — | 40.44 | 3.22 | — | 117–121 |

EXAMPLE LIX

Preparation of mono-ethyl methylthiomalonate

Diethyl methylthiomalonate (25.0 grams, 0.1 mole) was saponified with potassium hydroxide (6.80 grams,

EXAMPLE LXI

In a manner similar to that employed in Example LX other compounds were prepared. The structured and analytical data for Compounds 222 through 224 are set forth in Table L below:

TABLE L

Representative Malonic Acid Derivative Compounds

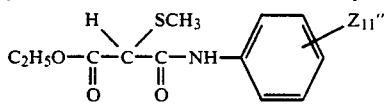

| Compound No. | Substituent $Z_{11}''$ | Elemental Analysis Calculated | | | Found | | | Melting Point °C. |
|---|---|---|---|---|---|---|---|---|
| | | C | H | N | C | H | N | |
| 222 | 3,5-Cl$_2$ | 44.73 | 4.07 | 4.35 | 44.88 | 4.23 | 4.33 | 74–76 |
| 223 | 4-Br | 43.38 | 4.25 | 4.22 | 43.85 | 4.28 | 3.85 | 84–87 |
| 224 | 4-CF$_3$ | 48.59 | 4.39 | 4.36 | 48.73 | 4.40 | 4.41 | 60.5–62.5 |

EXAMPLE LXII

Preparation of ethyl 3-[(4-bromo-2-methylphenyl)amino]-2-methoxy-2-methyl-3-oxopropanoate Part A: Preparation of diethyl methoxy(methyl)malonate Diethyl methoxymalonate (31.0 grams, 0.2 mole), prepared in Example LIII Part A, sodium hydride (3.91 grams of 60% reagent, 0.2 mole), methyl iodide (46.27 grams, 0.3 mole) and 15-crown-5 (2 drops) were reacted in 300 milliliters of N,N-dimethylformamide in a manner similar to that described in Example LII Part A to give 23.77 grams (0.1 mole) of diethyl methoxy(methyl)malonate. NMR analysis of the product indicated the following:

'H NMR (CDCl$_3$) δ1.12–1.48(t, 6H, 2×CH$_3$), 1.63(s, 3H, a—CH$_3$), 3.42(s, 3H, CH$_3$O), 4.08–4.51 (q, 4H, 2×CH$_2$) ppm.

Part B: Preparation of mono-ethyl methoxy(methyl)malonate

Diethyl methoxy(methyl)malonate (23.77 grams, 0.12 mole), prepared in Part A, was saponified with potassium hydroxide (6.53 grams, 0.12 mole) in a mixture of 200 milliliters of ethanol and 2.1 grams (0.12 mole) of water and worked up under conditions similar to those described in Example XII but employing a saponification period of about 16 hours. Following the acidification procedure the product was recovered by continuous liquid-liquid extraction with methylene chloride to give 14.52 grams (0.08 mole) of mono-ethyl methoxy(methyl)malonate. NMR analysis of the product indicated the following:

'H NMR (CDCl$_3$) δ1.15–1.47(t, 3H, CH$_3$), 1.68(s, 3H, —CH$_3$), 3.44(s, 3H, CH$_3$O). 4.1–4.5(q, 2H, CH$_2$), 9.25(br s, H, CO$_2$H) ppm.

Part C: Preparation of ethyl 2-(chlorocarbonyl)-2-methoxypropionate

Mon-ethyl methoxy(methyl)malonate (14.52 grams, 0.08 mole) was reacted with thionyl chloride (19.61 grams, 0.16 mole) at 50° C. for a 13-hour reaction period with an additional holding period of approximately 32 hours at room temperature. Vacuum evaporation of the excess thionyl chloride gave 15.2 grams (0.08 mole) of ethyl 2-(chlorocarbonyl)-2-methoxypropionate. NMR analysis of the product indicated the following:

'H NMR CDCl$_3$) δ1.15–1.46(t, 3H, CH$_3$), 1.71(s, 3H, —CH$_3$), 3.45(s, 3H, CH$_3$O), 4.10–4.52(q, 2H, CH$_2$) ppm.

Part D: Preparation of ethyl 3-[(4-bromo-2-methylphenyl)amino]-2-methoxy-2-methyl-3-oxopropanoate 4-Bromo-2-methylaniline (2.83 grams, 0.02 mole) and ethyl 2-(chlorocarbonyl)-2-methoxypropionate (4.12 grams, 0.02 mole), prepared in Part C, were reacted in the presence of triethylamine (1.54 grams, (0.02 mole) in 200 milliliters of methylene chloride in a manner similar to that described in Example I to give 1.73 grams (0.005 mole) of ethyl 3-[(4-bromo-2-methyl-phenyl)amino]-2-methoxy-2-methyl-3-oxopropanoate having a melting point of 99° C.-103° C.

Elemental analysis of the product indicated the following: Analysis: $C_{13}H_{16}BrNO_5$; Calculated: C, 45.10; H, 4.66; N, 4.05. Found: C, 45.27; H, 4.83; N, 3.69.

This compound is referred to hereinafter as Compound 225.

EXAMPLE LXIII

Preparation of ethyl 3-[(3,5-dichlorophenyl)amino]-2-methoxy-2-methyl-3-oxopropanoate 3,5-Dichloroaniline (3.33 grams, 0.02 mole), ethyl 2-(chlorocarbonyl)-2-methoxypropionate (4.0 grams, 0.02 mole), prepared in Example LXII Part C, and triethylamine (2.08 grams, 0.02 mole) were reacted in a manner similar to the procedure described in Example I to give 4.40 grams (0.01 mole) of ethyl 3-[(3,5-dichlorophenyl)amino]-2-methoxy-2-methyl-3-oxopropanoate having a melting point of 72° C.-75° C.

Elemental analysis of the product indicated the following: Analysis: $C_{13}H_{14}Cl_2NO_4$; Calculated: C, 48.77; H, 4.72; N, 4.38. Found: C, 48.74; H, 4.73; N, 4.39.

This compound is referred to hereinafter as Compound 226.

EXAMPLE LXIV

Preparation of dimethyl dimethoxymalonate

To a solution of sodium methoxide prepared by dissolving 5.75 grams (0.25 mole) of sodium in 375 milliliters of anhydrous methanol was added 59.8 grams (0.25 mole) of diethyl bromomalate in one portion and the resulting mixture heated under reflux for 4 hours. The mixture was freed of methanol solvent under reduced pressure and the residue taken up in ethyl ether and filtered to remove by-product solids. The filtrate was freed of ether under reduced pressure and the residue vacuum distilled in a short-path system to give 6.49 grams (0.03 mole) of dimethyl dimethoxymalonate boiling over a range of 100° C.-125° C. at 1.4–1.8 mm of Hg. NMR analysis of the product indicated the following:

'H NMR (CDCl$_3$) δ3.39(s, 6H, 2×CH$_3$O), 3.85(s, 6H, 2×CH$_3$O) ppm.

This compound is referred to hereinafter as Compound 227.

EXAMPLE LXV

Preparation of methyl 3-[(4-bromo-2methylphenyl)amino]-2,2-dimethoxy-3-oxopropanoate Part A: Preparation of methyl chlorocarbonyl (dimethoxy)acetate A 6.49-gram (0.03 mole) portion of dimethyl dimethoxymalonate prepared in Example LXIV (Compound 226) was saponified with 1.89 grams (0.03 mole) of potassium hydroxide, 0.61 gram (0.03 mole) of water and 70 milliliters of methanol in a manner similar to that described in Example LII Part B, recovering the dry monopotassium salt following azeotropic removal of water by distillation with toluene. The potassium salt was suspended in 110 milliliters of benzene and, with stirring and cooling at 0° C.-5° C., 12.86 grams (0.1 mole) of oxalyl chloride were added dropwise followed by 3 drops of pyridine. The reaction mixture was then allowed to warm to room temperature while stirring for an approximate 16-hour period. Evaporation of volatiles from the mixture under reduced pressure gave 4.12 grams of a residue consisting of methyl chlorocarbonyl(dimethoxy)acetate (2.99 grams, 0.01 mole) and 1.13 grams of potassium chloride and used without purification in Part B.

Part B: Preparation of methyl 3-[(4-bromo-2-methylphenyl)amino]-2,2-dimethoxy-3-oxopropanoate 4-Bromo-2-methylaniline (2.83 grams, 0.01 mole), methyl chlorocarbonyl(dimethoxy)acetate (2.99 grams, 0.01 mole), prepared in Part A, and triethylamine (1.54 grams, 0.015 mole) were reacted in a manner similar to the procedure described in Example I to give 1.73 grams (0.005 mole) of methyl 3-[(4-bromo-2-methylphenyl)amino]-2,2-dimethoxy-3-oxopropanoate having a melting point of 99° C.-103° C.

Elemental analysis of the product indicated the following: Analysis: $C_{13}H_{16}BrNO_5$; Calculated: C, 45.10; H, 4.66; N, 4.05. Found: C, 45.27; H, 4.83; N, 3.69.

This compound is referred to hereinafter as Compound 228.

EXAMPLE LXVI

Preparation of methyl 3-[(3,5-dichlorophenyl)amino]-2,2-dimethoxy-3-oxopropanoate In a manner similar to the procedure described in Example I, 3,5-dichloroaniline was reacted with methyl chlorocarbonyl(dimethoxy)acetate, prepared as described in Example LXV Part A, employing triethylamine as the acid acceptor in methylene chloride solution. The methyl 3-[(3,5-dichlorophenyl)amino]-2,2-dimethoxy-3-oxopropanoate product (2.31 grams, 0.007 mole) was obtained as colorless crystals having a melting point of 160° C.-164° C.

Elemental analysis of the product indicated the following: Analysis: $C_{12}H_{13}Cl_2NO_5$; Calculated: C, 44.74; H, 4.07; N, 4.35. Found: C, 44.88; H, 4.06; N, 4.12.

This compound is referred to hereinafter as Compound 229.

EXAMPLE LXVII

Preparation of diethyl ethoxymalonate

Part A: Preparation of diethyl diazomalonate

To a stirred solution of 24.52 grams (0.15 mole) of diethyl malonate and 34.0 grams (0.15 mole) of 2-naphthalenesulfonyl azide in 100 milliliters of acetonitrile was added 15.49 grams (0.15 mole) of triethylamine, dropwise, with cooling at 0° C.-5° C. On completing the feed the mixture was allowed to warm to room temperature while stirring for an approximate 16-hour period. Volatiles were stripped from the mixture under reduced pressure and the residue was slurried with ethyl ether and the inorganic salt filtered off. The filtrate was evaporated free of ether and purified by silica column chromatography to give 27.03 grams (0.15 mole) of diethyl diazomalonate as a yellow liquid. NMR analysis of the product indicated the following:

$^1$H NMR ($CDCl_3$) $\delta$1.15–1.50(t, 6H, 2×$CH_3$), 4.10–4.55(q, 4H, 2×$CH_2$) ppm.

Part B: Preparation of diethyl ethoxymalonate

A solution of 25.0 grams (0.1 mole) of diethyl diazomalonate, prepared in Part A, in approximately 600 milliliters of ethanol was charged to a 100 W Hanovia mercury arc lamp-containing system and photolyzed at room temperature for a period of approximately 56 hours, at which time IR examination of an aliquot of the mixture indicated complete conversion of the diazo compound. The ethanol was stripped from the solution under reduced pressure and the yellow residue distilled through a Kugelrohr apparatus at high vacuum to give 17.34 grams of a colorless liquid. The latter was then fractionally distilled, using a 5-inch glass ring-packed column, giving 10.08 grams (0.05 mole) of diethyl ethoxymalonate having a boiling point of 65° C.-70° C. at 0.05 mm Hg. NMR analysis of the product indicated the following:

$^1$H NMR ($CDCl_3$) $\delta$1.10–1.46(2xt, 9H), 3×$CH_3$), 3.48–3.89(q, 2H, ether $CH_2O$), 4.10–4.45(q, 4H, 2×ester $CH_2O$), 4.48(s, methine CH) ppm.

This compound is referred to hereinafter as Compound 230.

EXAMPLE LXVIII

Preparation of ethyl 3-[(3,5-dichlorophenyl)amino]-2-ethoxy-3-oxopropanoate

Part A: Preparation of mono-ethyl ethoxymalonate

Diethyl ethoxymalonate (10.08 grams, 0.05 mole), prepared as described in Example LXVII, Part B, was saponified with potassium hydroxide (2.77 grams, 0.05 mole) in a mixture of 200 milliliters of ethanol and 0.88 gram (0.05 mole) of water and worked up under conditions similar to those described in Example LIX giving 4.32 grams (0.02 mole) of mono-ethyl ethoxymalonate as a residue product. NMR analysis of the product indicated the following:

$^1$H NMR($CDCl_3$) $\delta$1.13–1.49(2xt, 6H, 2×$CH_3$), 3.51–3.95(q, 2H, ether $CH_2O$), 4.10–4.50(q, 2H, ester $CH_2O$), 4.53(s, methine CH), 6.95(s, COOH) ppm.

Part B: Preparation of ethyl 3-[(3,5-dichlorophenyl)amino]-2-ethoxy-3-oxopropanoate Mono-ethyl ethoxymalonate (2.75 grams, 0.02 mole), prepared in Part A, 3,5-dichloroaniline (2.53 grams, 0.02 mole) and 1,3-dicyclohexylcarbodiimide (3.22 grams, 0.02 mole) were reacted in a manner similar to that described in Example LVII to give 1.92 grams (0.006 mole) of ethyl 3-[(3,5-dichlorophenyl)amino]-2-ethoxy-3-oxopropanoate having a melting point of 89.0° C.-92.5° C. An analytical sample recrystallized from ethyl acetate-hexane had a melting point of 84° C.-86° C.

Elemental analysis of the product indicated the following: Analysis: $C_{13}H_{15}Cl_2NO_4$; Calculated: C, 48.77; H, 4.72; N, 4.38. Found: C, 48.63; H, 4.59; N, 3.98.

This compound is referred to hereinafter as Compound 231.

EXAMPLE LXIX

Preparation of ethyl 3-[(4-bromophenyl)amino]-2-ethoxy-3-oxopropanoate

Mono-ethyl ethoxymalonate (1.44 grams, 0.01 mole), prepared in Example LXVIII Part A, 4-bromoaniline (1.41 grams, 0.01 mole) and 1,3-dicyclohexylcarbodiimide (1.68 grams, 0.01 mole) were reacted in a manner similar to that described in Example LVII to give 0.79 gram (0.002 mole) of ethyl 3-[(4-bromophenyl)amino]-2-ethoxy-3-oxopropanoate having a melting point of 59° C.-64° C. An analytical sample recrystallized from hexane-ethyl acetate had a melting point of 62° C.-64° C.

Elemental analysis of the product indicated the following: Analysis: $C_{13}H_{16}BrNO_4$; Calculated: C, 47.79; N, 4.88; N, 4.24. Found: C, 47.20; N, 4.94; N, 4.21.

This compound is referred to hereinafter as Compound 232.

EXAMPLE LXX

Preparation of methyl 3-[(3,5-dichlorophenyl)amino]-2-methoxy-3-oxopropanoate Part A: Preparation of methyl (chlorocarbonyl)methoxyacetate Mono-methyl methoxymalonate (9.8 grams, 0.07 mole), prepared in Example LVI (Compound 214) was reacted with thionyl chloride (15.74 grams, 0.13 mole) in 100 milliliters of methylene chloride in a manner similar to that described in Example LIII Part C, to give 11.06 grams (0.07 mole) of methyl (chlorocarbonyl)methoxyacetate. NMR analysis of the product indicated the following:

$^1$H NMR (CDCl$_3$) δ3.58(s, 3H, CH$_3$O—C), 3.85(s, 3H, CH$_3$O$_2$C), 4.65(s, H, CH) ppm.

Part B: Preparation of methyl 3-[(3,5-dichlorophenyl)amino]-2-methoxy-3-oxopropanoate 3,5-Dichloroaniline (4.86 grams, 0.03 mole) and methyl (chlorocarbonyl)methoxyacetate (5.0 grams, 0.03 mole), prepared in Part A, were reacted in the presence of triethylamine (3.04 grams, 0.03 mole) in a manner similar to that described in Example LIV to give 2.74 grams (0.009 mole) of methyl 3-[(3,5-dichlorophenyl)amino]-2-methoxy-3-oxopropanoate having a melting point of 116° C.-118.5° C.

Elemental analysis of the product indicated the following: Analysis: $C_{11}H_{11}Cl_2NO_4$; Calculated: C, 45.23; H, 3.80; N, 4.80. Found: C, 44.75; H, 3.55; N, 4.70.

THis compound is referred to hereinafter as Compound 233.

EXAMPLE LXXI

Preparation of n-propyl 3-[(3,5-dichlorophenyl)amino]-2-methoxy-3-oxopropanoate Part A: Preparation of di n-propyl methoxymalonate Dimethyl methoxymalonate (25.0 grams, 0.15 mole) and a large excess of n-propyl alcohol (250 milliliters) were reacted in the presence of p-toluenesulfonic acid (1.36 grams) catalyst, in a manner similar to that described in Example LIII Part A, to give 33.23. grams (0.15 mole) of di-n-propyl methoxymalonate. NMR analysis of the product indicated the following:

$^1$H NMR (CDCl$_3$) δ0.77-1.14(t, 6H, 2×CH$_3$), 1.42-2.06(m, 4H, 2×C—CH$_2$—C), 3.52(s, 3H, CH$_3$O), 4.05-4.49(n, 5H, 2×CH$_2$O and C—H) ppm.

Part B: Preparation of mono-n-propyl methoxymalonate

Di-n-propyl methoxymalonate (33.23 grams, 0.15 mole) was saponified with potassium hydroxide (8.54 grams, 0.15 mole) in a mixture of 325 milliliters of n-propyl alcohol and 2.74 grams (0.15 mole) of water according to the general procedure of Example VII but employing a reaction period of 16 hours. Workup according to the method of Example VII afforded 13.07 grams (0.07 mole) of mono-n-propyl methoxymalonate. NMR analysis of the product indicated the following:

$^1$H NMR (CDCl$_3$) δ0.76-1.14(t, 3H, CH$_3$), 1.39-1.96(m, 2H, C—CH$_2$—C), 3.56(s, 3H, CH$_3$O), 4.08-4.39(t, 2H, CH$_2$O), 4.48(s, H, C—H), 9.38-9.75 (broad, H, CO$_2$H) ppm.

Part C: Preparation of n-propyl 3-[(3,5-dichlorophenyl)amino]-2-methoxy-3-oxopropanoate Mono-n-propyl methoxymalonate (13.07 grams, 0.07 mole), prepared in Part B, 3,5-dichloroaniline (12.02 grams, 0.07 mole) and 1,3-dicyclohexylcarbodiimide (15.31 grams, 0.07 mole) were reacted in a manner similar to that described in Example LVII to give 7.22 grams (0.02 mole) of n-propyl 3-[(3,5-dichlorophenyl)amino]-2-methoxy-3-oxopropanoate having a melting point of 89° C.-93° C. An analytical sample recrystallized from hexane had a melting point of 89° C.-92° C.

Elemental analysis of the product indicated the following: Analysis: $C_{13}H_{15}Cl_2NO_4$; Calculated: C, 48.77; H, 4.72. Found: C, 48.63; H, 4.95.

This compound is referred to hereinafter as Compound 234.

EXAMPLE LXXII

Preparation of potassium 3-[(3,5-dichlorophenyl)amino]-2-methoxy-3-oxopropanoate n-Propyl 3-[(3,5-dichlorophenyl)amino]-2-methoxy-3-oxopropanoate (5.47 grams, 0.02 mole), prepared in Example LXXI (Compound 234) was saponified with potassium hydroxide (1.01 grams, 0.02 mole) in the presence of 75 milliliters of ethanol and 0.31 gram (0.02 mole) of water in a manner similar to that described in Example LXXI Part B. The potassium salt that separated from the reaction mixture was filtered off, washed with ethanol and dried to give 0.98 gram (0.003 mole) of potassium 3-[(3,5-dichlorophenyl)amino]-2-methoxy-3-oxopropanoate. NMR analysis of the product indicated the following:

$^1$H NMR (D$_2$O) δ3.53(s, 3H, CH$_3$O), 4.41(s, H, CH), 7.26-7.69(m, 3H, phenyl) ppm.

This compound is referred to hereinafter as Compound 235.

EXAMPLE LXXIII

Preparation of 3-[(3,5-dichlorophenyl)amino]-2-methoxy-3-oxopropanoic acid

The saponification filtrate from Example LXXII was evaporated free of volatiles under reduced pressure and the residue dissolved in water and extracted twice with methylene chloride. The aqueous phase was acidified with 2N HCl, extracted twice with methylene chloride and this extract then dried (MgSO$_4$), filtered and vacuum stripped to give a yellow solid. Recrystallization from ethyl acetate-hexane gave 0.76 gram (0.003 mole) of 3-[(3,5-dichlorophenyl)amino]-2-methoxy-3-oxopropanoic acid having a melting point of 142° C.-145° C. with decarboxylation.

Elemental analysis of the product indicated the following: Analysis: $C_{10}H_9Cl_2NO_4$; Calculated: C, 43.19; H, 3.26. Found: C, 43.05; H, 3.53.

This compound is referred to hereinafter as Compound 236.

EXAMPLE LXXIV

Preparation of t-butyl 3-[(3,5-dichlorophenyl)amino]-2-methoxy-3-oxopropanoate

Part A: Preparation of t-butyl methyl methoxymalonate

To a stirred solution of 9.26 grams (0.06 mole) of methyl (chlorocarbonyl)methoxyacetate in 25 milliliters of carbon tetrachloride was added a mixture of 4.94 grams (0.07 mole) of anhydrous t-butyl alcohol, 4.50 milliliters (0.06 mole) of pyridine and 25 milliliters of carbon tetrachloride over an approximate 20-minute period, with cooling to 0° C.-5° C. by an ice bath. On completing the addition, the cooling bath was removed and the mixture allowed to stir for a 4-hour period at ambient temperature after which pyridine hydrochloride was removed from the mixture by filtration. The filtrate was diluted with 100 milliliters of methylene chloride and partitioned with 100 milliliters of saturated aqueous sodium bicarbonate following which the organic phase was extracted with cold 10% hydrochloric acid (3 × 100 milliliters), then with cold water (3 × 100 milliliters) after which it was dried (MgSO$_4$) and solvents then flash evaporated. The residue was vacuum distilled to give 7.57 grams (0.04 mole) of t-butyl methyl methoxymalonate having a boiling point of 93.5° C.-95° C. at 4.0 mm Hg.

Part B: Preparation of mono-t-butyl methoxymalonate t-Butyl methyl methoxymalonate (7.57 grams, 0.04 mole), prepared in Part A, was saponified with potassium hydroxide (2.45 g, 0.04 mole) in a mixture of 25 milliliters of methanol and 668 microliters (0.04 mole) of water according to the general procedure of Example VII but employing a reaction period of 20 hours. Workup according to the general method of Example VII gave 5.42 grams (0.03 mole) of mono-t-butyl methoxymalonate. NMR analysis of the product indicated the following:

$^1$H NMR (CDCl$_3$) δ1.45(s, 9H, t-butyl), 3.58(s, 3H, CH$_3$), 4.45(s, H, CH), 10.51(s, H, CO$_2$H) ppm.

Part C: Preparation of t-butyl 3-[(3,5-dichlorophenyl)amino]-2-methoxy-3-oxopropanoate Mono-t-butyl methoxymalonate (5.42 grams, 0.03 mole), prepared in Part B, 3,5-dichloroaniline (4.62 grams, 0.03 mole) and 1,3-dicyclohexylcarbodiimide (5.88 grams, 0.03 mole) were reacted in a manner similar to that described in Example LVII to give 2.92 grams (0.009 mole) of t-butyl 3-[(3,5-dichlorophenyl)amino]-2-methoxy-3-oxopropanoate having a melting point of 129.5° C.-131.5° C.

Elemental analysis of the product indicated the following: Analysis: $C_{14}H_{17}Cl_2NO_4$; Calculated: C, 50.31; H, 5.13; N, 4.19. Found: C, 50.09; H, 5.19; N, 4.08.

This compound is referred to hereinafter as Compound 237.

EXAMPLE LXXV

Preparation of methyl 3-[(3,5-dichlorophenyl)amino]-2-methoxy-3-thioxopropanoate A mixture of 3.50 grams (0.01 mole) of methyl 3-[(3,5-dichlorophenyl)amino]-2-methoxy-3-oxopropanoate (Compound 233, Example LXX), 2.42 grams (0.006 mole) of 2,4-bis(4-methoxyphenyl)-1,3-dithia-2,4-diphosphetane-2,4-disulfide and 35 milliliters of anhydrous 1,1-dimethoxyethane was stirred at room temperature for a period of about 20 hours after which stirring was continued with testing at 55° C. for a 168-hour interval. Solvent was removed from the reaction mixture under reduced pressure and the residue worked up by flash column chromatography to give 2.31 grams (0.007 mole) of methyl 3-[(3,5-dichloro-phenyl)amino]-2-methoxy-3-thioxopropanoate having a melting point of 144° C.-147° C.

Elemental analysis of the product indicated the following:

Analysis: $C_{11}H_{11}Cl_2NO_3S$: Calculated: C, 42.87; H, 3.60; S, 10.40. Found: C, 42.81; H, 3.22; S, 10.89.

This compound is referred to hereinafter as Compound 238.

EXAMPLE LXXVI

In a manner similar to that employed in Example LXXV other compounds were prepared. The structures and analytical data for Compounds 239 through 241 are set forth in Table M below.

TABLE M

Representative Malonic Acid Derivative Compounds

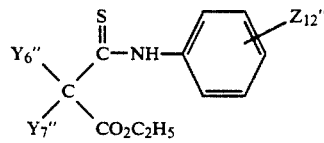

| Compound No. | Substituent | | | Elemental Analysis | | | | | | | | Melting Point °C. |
|---|---|---|---|---|---|---|---|---|---|---|---|---|
| | | | | Calculated | | | | Found | | | | |
| | $Y_6''$ | $Y_7''$ | $Z_{12}''$ | C | H | N | S | C | H | N | S | |
| 239 | CH$_3$O | H | 4-Br | 41.52 | 3.90 | — | 10.08 | 41.31 | 3.88 | — | 10.39 | 95–98 |
| 240 | —CH$_2$—CH$_2$— | | 2-CH$_3$-4-Br | 49.13 | 4.71 | 4.09 | — | 49.12 | 4.84 | 4.07 | — | 93–95 |
| 241 | H | H | 2-CH$_3$-4-Br | 45.58 | 4.46 | — | — | 45.98 | 4.52 | — | — | 78–80.5 |

EXAMPLE LXXVII

In a manner similar to that employed in Example XLII, other compounds were prepared. The structures and analytical data for Compounds 242 through 246 are set forth in Table N below.

TABLE N

Representative Malonic Acid Derivative Compounds

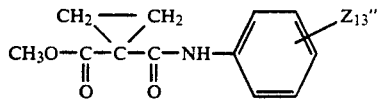

| Compound No. | Substituent $Z_{13}''$ | Elemental Analysis Calculated | | | Elemental Analysis Found | | | Melting Point °C. |
|---|---|---|---|---|---|---|---|---|
| | | C | H | N | C | H | N | |
| 242 | 4-Br | 48.34 | 4.06 | 4.70 | 48.56 | 4.12 | 4.65 | 126.0–127.5 |
| 243 | 2-F-4-Cl | 53.05 | 4.08 | 5.16 | 52.71 | 4.45 | 4.71 | 93.5–95.5 |
| 244 | 4-CF$_3$ | 54.35 | 4.21 | 4.88 | 53.96 | 4.44 | 4.42 | 114.5–116 |
| 245 | 2-F-4-Br | 45.59 | 3.51 | 4.43 | 45.53 | 3.76 | 4.21 | 149.5–151 |
| 246 | 2,4-Cl$_2$ | 50.02 | 3.85 | 4.86 | 50.00 | 3.92 | 4.89 | 134–136 |

EXAMPLE LXXVIII

Preparation of ethyl 1-(4-trifluoromethylphenylaminocarbonyl)cyclopropanecarboxylate 1-Carboethoxycyclopropanecarboxylic acid (9.81 grams, 0.06 mole), ethyl chloroformate (6.73 grams, 0.06 mole) and 4-aminobenzotrifluoride (10.0 grams, 0.06 mole) were reacted sequentially in the presence of triethylamine (6.28 grams, 0.06 mole) in a manner similar to that described in Example XXXIII to give 10.25 grams (0.03 mole) of ethyl 1-(4-trifluoromethylphenylaminocarbonyl)cyclopropanecarboxylate having a melting point of 80.5° C.–82.0° C.

elemental analysis of the product indicated the following:

Analysis: C$_{14}$H$_{14}$F$_3$NO$_3$: Calculated: C, 55.82; H, 4.68; N, 4.65. Found: C, 55.53; N, 5.01; N, 4.43.

This compound is referred to hereinafter as Compound 247.

EXAMPLE LXXIX

Preparation of ethyl 1-[N-(4-bromophenyl)-N-methylaminocarbonyl]cyclopropanecarboxylate Ethyl 1-chlorocarbonylcyclopropanecarboxylate (3.11 grams, 0.02 mole), prepared in Example XVIII, 4-bromo-N-methylaniline (3.00 grams, 0.02 mole) and triethylamine (1.63 grams, 0.02 mole) were reacted in a manner similar to that described in Example III to give 3.79 grams (0.01 mole) of ethyl 1-[N-(4-bromophenyl)-N-methylaminocarbonyl]cyclopropanecarboxylate isolated as a colorless oil.

Elemental analysis of the product indicated the following:

Analysis: C$_{14}$H$_{16}$BrNO$_3$: Calculated: C, 51.55; H, 4.94; N, 4.29. Found: C, 51.73; N, 4.87; N, 4.27.

This compound is referred to hereinafter as Compound 248.

EXAMPLE LXXX

In a manner similar to that employed in Example LXXIX other compounds were prepared. The structures and analytical data for Compounds 249 through 250 are set forth in Table O below.

TABLE O

Representative Malonic Acid Derivative Compounds

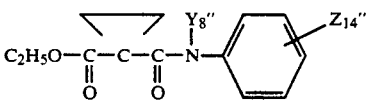

| Compound No. | Substituent | | Elemental Analysis Calculated | | | Elemental Analysis Found | | | Melting Point °C. |
|---|---|---|---|---|---|---|---|---|---|
| | $Y_8''$ | $Z_{14}''$ | C | H | N | C | H | N | |
| 249 | C$_2$H$_5$ | 4-Cl | 60.92 | 6.13 | 4.74 | 59.81 | 6.13 | 4.58 | Oil |
| 250 | CH$_3$ | 2-CH$_3$-4-Br | 52.96 | 5.33 | 4.12 | 52.54 | 5.23 | 4.00 | Oil |

EXAMPLE LXXXI

Preparation of 1-[N-(4-chlorophenyl)-N-ethylaminocarbonyl]cyclopropanecarboxylic acid A 12.72-gram (0.04 mole) portion of ethyl 1-[N-(4-chlorophenyl)-N-ethylaminocarbonyl]cyclopropanecarboxylate (Compound 249, Example LXXX) was hydrolyzed in a manner similar to that described in Example VII, employing a saponification period of 15 hours at room temperature, to give 1.97 grams (0.007 mole) of 1-[N-(4-chlorophenyl)-N-ethylaminocarbonyl]cyclopropanecarboxylic acid having a melting point of 99° C.–101° C.

Elemental analysis of the product indicated the following:

Analysis: C$_{13}$H$_{14}$ClNO$_3$·1 ½H$_2$O: Calculated: C, 52.98; H, 5.81; N, 4.75. Found: C, 53.04; H, 5.70; N, 4.71.

This compound is referred to hereinafter as Compound 251.

EXAMPLE LXXXII

In a manner similar to that employed in Example LXXXI other compounds were prepared. The structures and analytical data for Compounds 252 through 253 are set forth in Table P below.

TABLE P

Representative Malonic Acid Derivative Compounds

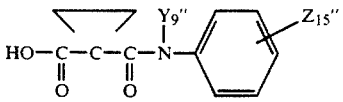

| Compound No. | Substituent Y$_9''$ | Substituent Z$_{15}''$ | Calculated C | Calculated H | Calculated N | Found C | Found H | Found N | Melting Point °C. |
|---|---|---|---|---|---|---|---|---|---|
| 252 | CH$_3$ | 4-Br | 48.34 | 4.06 | 4.70 | 48.75 | 4.09 | 4.71 | 186.5–188 |
| 253 | CH$_3$ | 2-CH$_3$-4-Br | 50.02 | 4.52 | 4.49 | 50.16 | 4.59 | 4.46 | 184–185 |

EXAMPLE LXXXIII

Preparation of ethyl 2-(3,5-dichlorophenylaminocarbonyl)propanoate

Mono-ethyl methylmalonate (5.0 grams, 0.03 mole), 3.5-dichloroaniline (5.54 grams, 0.03 mole) and 1,3-dicyclohexylcarbodiimide (7.06 grams, 0.03 mole) were reacted in a manner similar to that described in Example LVII to give 1.0 gram (0.003 mole) of ethyl of 2-(3,5-dichlorophenylaminocarbonyl)propanoate having a melting point of 89° C.-90° C.

Elemental analysis of the product indicated the following:

Analysis: C$_{12}$H$_{12}$NO$_3$: Calculated: C, 49.67; H, 4.51; N, 4.83. Found: C, 49.65; H, 4.49; N, 4.79.

This compound is referred to hereinafter as Compound 254.

EXAMPLE LXXXIV

Preparation of ethyl 2-(3,5-dichlorophenylaminocarbonyl)butanoate

Mono-ethyl ethylmalonate (5.0 grams, 0.03 mole), 3,5-dichloroaniline (5.06 grams, 0.03 mole) and 1,3-dicyclohexylcarbodiimide (6.44 grams, 0.03 mole) were reacted in a manner similar to that described in Example LVII to give 0.87 gram (0.003 mole) of ethyl 2-(3,5-dichlorophenylaminocarbonyl)butanoate having a melting point of 96.5° C.-98° C.

Elemental analysis of the product indicated the following:

Analysis: C$_{13}$H$_{15}$Cl$_2$NO$_3$: Calculated: C, 51.33; H, 4.97; N, 4.60. Found: C, 51.95; H, 5.10; N, 4.30.

This compound is referred to hereinafter as Compound 255.

EXAMPLE LXXXV

Preparation of 2-cyclopropenyl-1-carboethoxy-1-[N-(2-methyl-4-bromophenyl)]carboxamide Part A: Preparation of diethyl bis(2,3-trimethylsilyl)-cyclopropene-1,1-dicarboxylate A 50 milliliter round-bottom flask was equipped with a magnetic stirring bar and a reflux condenser with N$_2$ inlet. The flask was charged with 183.0 grams (1.07 mole) of bis(trimethylsilyl) acetylene and 0.40 gram (0.0015 mole) of cupric acetylacetonate. Using an oil bath the temperature of the stirred mixture was raised to 145° C. Using a syringe pump 39.3 grams (0.21 mole) of diethyl diazomalonate were added over 36 hours. Heating at 1450° C. was continued for an additional 12 hours after all of the diazomalonate had been added. The excess bis(trimethylsilyl)acetylene was removed by vacuum distillation. The residue product was purified by flash chromatography eluting with 80:20 hexane-ethyl acetate to give 17.0 grams (0.05 mole) of diethyl bis(2,3-trimethylsilyl)cyclopropene-1,1-dicarboxylate as a yellow liquid. NMR analysis of the product indicated the following:

'H NMR (CDCl$_3$): 0.23(s, 18H), 1.20 (t, 6H), 4.17(q, 4H) ppm.

Part B: Preparation of diethyl cyclopropene-1,1-dicarboxylate

A 500 milliliter round-bottom flask was equipped with a magnetic stirrer and N$_2$ inlet. The flask was charged with 21.0 grams (0.07 mole) of diethyl bis (2,3-trimethylsilyl) cyclopropene-1,1-dicarboxylate, 125 milliliters of acetonitrile, 12.2 grams (0.21 mole) of anhydrous KF, and 6.50 grams (0.02 mole) of dicyclohexano-18-crown-6 ether. The mixture was stirred 6 hours at room temperature. The mixture was filtered and the filtrate concentrated under reduced pressure to a deep red oil. This oil was taken up in 100 milliliters of methanol and stirred 24 hours at room temperature. The methanol was removed under vacuum and the residue purified by flash column chromatography to give 6.25 grams (0.02 mole) of diethyl cyclopropene-1,1-dicarboxylate as a yellow oil. NMR analysis of the product indicated the following: 'H NMR (CDCl$_3$): δ 1.25 (t, 6H), 4.23 (q, 4H); 7.08 (s, 2H).

Part C: Preparation of mono-ethyl cyclopropene-1,1-dicarboxylate

A 250 milliliter round-bottom flask was equipped with a magnetic stirring bar and an addition funnel with N$_2$ inlet. The flask was charged with 6.15 grams (0.03 mole) of diethylcyclopropene-1,1-dicarboxylate and 50 milliliters of ethanol. The stirred mixture was cooled in an ice bath and a solution of 1.33 grams (0.03 mole) of NaOH in 5.0 milliliters of water was added dropwise. The mixture was allowed to come to room temperature and stirred for 3 days. The reaction mixture was concentrated to ¼ of the original volume under reduced pressure, diluted with ice water, and extracted twice with ether. The basic aqueous phase was acidified with ice cold 10% HCl, and extracted three times with ethyl acetate. The ethyl acetate was dried (MgSO$_4$) and the solvent removed under reduced pressure to leave an orange colored solid. This was recrystallized from hexane-ethyl acetate to give 3.65 grams (0.02 mole) of monoethyl cyclopropene-1,1-dicarboxylate as a light yellow solid having a melting point of 7600° C.-77.50° C. NMR analysis of the product indicated the following:

'H NMR (CDCl$_3$): δ 1.20 (t, 3H),4.25 (q, 2H), 6.80 (s, 2H), 11.5 (br s, 1H) ppm.

Part D: Preparation of 1-carboethoxy-1-ethoxycarbonyloxycarbonyl-2-cyclopropene

A 250 milliliter round-bottom flask was equipped with a magnetic stirrer and an addition funnel with $N_2$ inlet. The flask was charged with 1.30 grams (0.008 mole) of mono-ethyl cyclopropene-1,1-dicarboxylate, 50 milliliters of dry THF, 2.3 grams (0.02 mole) of potassium carbonate (anhydrous), and 450 milligrams of dicyclohexano-18-crown-6 ether. The stirred reaction mixture was cooled to 00° C., and 0.90° C. gram (0.008 mole) of ethyl chloroformate in 10 milliliters of THF was added dropwise. The mixture was stirred for 2½ hours at 00° C. At this time an aliquot from the reaction mixture showed a very strong anhydride carbonyl stretch at 1820 cm$^{-1}$ in the infrared indicating the formation of the mixed anhydride 1-carboethoxy-1-ethoxycarbonyloxycarbonyl-2-cyclopropene.

The balance of the reaction mixture containing the mixed anhydride was carried on to Part E.

Part E: Preparation of 2-cyclopropenyl-1-carboethoxy-1[N-(2-methyl-4-bromophenyl)] carboxamide A solution of 1.40 grams (0.0075 mole) of 2-methyl-4-bromoaniline in 10 milliliters of tetrahydrofuran was added dropwise to the reaction mixture from part D at 00° C. The mixture was allowed to come to room temperature and stirred for 2 hours. The reaction mixture was filtered and the filtrate concentrated under reduced pressure to give an orange colored solid. This solid was washed with ether and recrystallized from hexane-ethyl acetate to give 1.5 grams (0.004 mole) of 2-cyclopropenyl-1-carboethoxy-1-[N-(2-methyl-4-bromophenyl)-]carboxamide as a white crystalline solid having a melting point of 1510° C.-1530° C. Elemental analysis of the product indicated the following:

Analysis: $C_{14}H_{14}BrNO_3$: Calculated: C, 51.85; N, 4.35; N, 4.32. Found: C, 51.67; H, 4.51; N, 4.23.

This compound is referred to hereinafter as Compound 256.

EXAMPLE LXXXVI

Preparation of 1-cyclopropenyl-1-carboxy-1[N-(2-methyl-4-bromophenyl]carboxamide A 250 milliliter round-bottom flask was equipped with a magnetic stirrer and addition funnel with $N_2$ inlet. The flask was charged with 1.65 grams (0.005 mole) of 2-cyclopropenyl-1-carboethoxy-1-[N-(2-methyl-4-bromophenyl)]carboxamide and 25 milliliters of ethanol. The reaction mixture was cooled in an ice bath, and a solution of 0.21 gram (0.005 mole) of NaOH in 5 milliliters of $H_2O$ was added dropwise. The reaction mixture was allowed to come to room temperature and stirred for 3 days. The reaction mixture was concentrated under reduced pressure to ¼ into its volume, poured into ice water, and extracted 2× with ether. The basic aqueous phase was acidified with 10% HCl and extracted into ethyl acetate, dried (MgSO$_4$) and the solvent removed. The residue was washed thoroughly with ether to yield 1.10 grams (0.004 mole) of 2-cyclopropenyl-1-carboxy-1[N-(2-methyl-4-bromophenyl)-]carboxamide as a white solid having a melting point of 1290° C.-1320° C. (dec.).

Elemental analysis of the product indicated the following:

Analysis: $C_{12}H_{10}BrNO_3$: Calculated: C, 48.65; H, 3.40; N, 4.73. Found: C, 4848; , 3.70; N, 4.39.

This compound is referred to hereinafter as compound 257.

EXAMPLE LXXXVII

Preparation of 2,3-diphenyl-2-cyclopropenyl-1-carboxy-1-[N-(2-methyl-4-bromophenyl)]carboxamide Part A: Preparation of dimethyl 2,3-diphenylcyclopropene-1,1-dicarboxylate A 100 milliliter round-bottom flask was equipped with a magnetic stirrer and reflux condenser with $N_2$ inlet. The flask was charged with 25.0 grams (0.140 mole) of diphenylacetylene and 140 milligrams of cupric acetylactonate. The mixture was heated to 1200° C. using an oil bath and 8.85 grams (0.056 mole) of dimethyl diazomalonate was added over 24 hours using a syringe pump. When all of the dimethyl diazomalonate had been added, heating at 1200° C. was continued for 8 hours. The diphenylacetylene was distilled off under vacuum, boiling point 1700° C./19 mm. The residue was purified by flash chromatography eluting with 75:25 hexane-ethyl acetate to give 4.65 grams (0.015 mole) of the desired product as a white solid. NMR analysis of the product indicated the following:

'H NMR (CDCl$_3$): δ 3.69 (s, 6H), 7.20–7.95 (m, 10H).

Part B: Preparation of Methyl (and ethyl) 2,3-diphenylcyclopropene-1,1-dicarboxylate A 100 milliliter round-bottom flask was equipped with a magnetic stirrer and addition funnel with $N_2$ inlet. The flask was charged with 6.1 grams (0.02 mole) of dimethyl 2,3-diphenylcyclopropene-1,1-dicarboxylate in 50 milliliters of ethanol, then cooled to 00° C. A solution of 0.79 gram (0.02 mole) of NaOH in 5 milliliters of water was added dropwise. The reaction mixture was allowed to come to room temperature and stirred for 6 days. The reaction mixture was concentrated to ⅓ volume under reduced pressure, poured into ice water, extracted twice with ether, and acidified with ice cold 10% HCl. The aqueous acid mixture was extracted three times with ether, the the solution ether washed with sat. NaCl solution, the solution dried (MgSO$_4$) and ether removed under vacuum to give 4.9 grams (0.017 mole) of a mixture of 67% methyl and 33% ethyl 2,3-diphenylcyclopropene-1,1-dicarboxylate as a white solid. NMR analysis of the product indicted the following:

'H NMR (CDCl$_3$): δ 1.10 (t, 3H), 3.70 (s, 3H), 4.18 (q, 2H), 7.20° C.-7.85° C. (m, 10H) ppm.

Part C: Preparation of mono-ethyl 2,3-diphenyl-1,1-cyclopropenedicarboxylate

The mixture (4.9 grams) of ethyl and methyl 2,3-diphenylcyclopropene-1,1-dicarboxylates prepared in Part B above was esterified by refluxing in ethanol-toluene containing a catalytic amount of P-toluenesulfonic acid with removal of water by type 3A molecular sieves. For the work-up the reaction mixture was heated to distill off approximately 90% of the solvent, diluted with ice water, and extracted with ether. The ether was washed with saturated NaHCO$_3$, then water; and dried (MgSO$_4$). The ether was removed to give 4.5 grams of a mixture of methyl ethyl 2,3-diphenylcyclopropene-1,1-dicarboxylate and diethyl 2,3-diphenylcyclopropene-1,1-dicarboxylate.

This 4.5 gram mixture of esters was taken up in 60 milliliters of ethanol and stirred for three days at room temperature with a solution of 0.49 gram (0.012 mole) of NaOH in 5 milliliters of water. The reaction mixture was concentrated under vacuum to ¼ its volume, diluted with ice water, extracted 3× with ether, and the aqueous layer acidified with 10% HCl. The acidified aqueous layer was extracted three times with methylene chloride, dried (MgSO$_4$), and the solvent removed to give 2.5 grams of (0.008 mole) of mono-ethyl 2,3-diphenyl-1,1-cyclopropenedicarboxylate as a white solid. NMR analysis of the product indicated the following:

'H NMR (CDCl$_3$): δ 1.10 (t, 3H), 4.20 (q, 2H), 7.10-7.90 (m, 10H), 11.5 (br s, 1H) ppm.

Part D: Preparation of 1-carboethoxy-1-ethoxycarbonyloxycarbonyl-2,3-diphenyl-2-cyclopropene A 250 milliliter round-bottom flask was equipped with a magnetic stirrer and an addition funnel with N$_2$ inlet. The flask was charged with 2.67 grams (0.0091 mole) of mono-ethyl 2,3-diphenyl-1,1-cyclopropenedicarboxylate, 60 milliliters of THF, 300 milligrams of dicyclohexano-18-crown-6-ether, and 2.5 grams (0.018 mole) of anhydrous K$_2$CO$_3$. The well stirred mixture was cooled to 00° C, and 1.08 grams (0.01 mole) of ethyl chloroformate in 10 milliliters of THF were added dropwise. After 1 hour of stirring at 00° C., infrared spectral analysis indicated a strong C=O anhydride peak at 1820 cm$^{-1}$ indicating formation of the mixed anhydride 1-carboethoxy-1-ethoxycarbonyloxycarbonyl-2,3-diphenyl-2-cyclopropene. The balance of the reaction mixture containing the mixed anhydride was carried forward to Part E.

Part E: Preparation of 2,3-diphenyl-2-cyclopropenyl-1-carboxy-1-[N-(2-methyl-4-bromophenyl)]carboxamide A solution of 1.68 grams (0.091 mole) of 2-methyl-4-bromoaniline in 10 milliliters of dry THF was added dropwise to the reaction mixture from Part D. The reaction mixture was allowed to warm to room temperature and stirred for an approximate 16-hour period. The reaction mixture was concentrated under vacuum to ¼ its original volume, diluted with water, extracted into CH$_2$Cl$_2$, washed three times with water, dried (MgSO$_4$), and the solvent removed to leave an orange oil. This material was purified by flash column chromatography using 75:25 hexane-ethyl acetate to give 1.9 grams of a light yellow solid. The nmr spectrum of this solid indicated that it was a mixture containing 70% of the desired 2,3-diphenyl-2-cyclopropenyl-1-carboxy-1-[N-(2-methyl-4-bromophenyl)]carboxamide ethyl ester and 30% ethyl 2-methyl-4-bromophenyl carbamate.

The 1.9 grams of solid were taken up in 30 milliliters of ethanol and a solution of 0.16 gram (0.0041 mole) of NaOH in 3 milliliters of water was added. The mixture was stirred three days at room temperature. The mixture was concentrated to /1/3 its original volume, diluted with ice water, extracted with ether, then acidified with 10% HCl. The acidified solution was extracted twice with CH$_2$Cl$_2$, dried (MgSO$_4$), and the solvent removed to leave a light yellow solid. This solid was washed with ether then recrystallized from hexane-ethyl acetate to give 450 milligrams (0.001 mole) of 2,3-diphenyl-2-cyclopropenyl-1-carboxy-1-[N-(2-methyl-4-bromophenyl)]carboxamide as a white solid having a melting point of 2140°-2150° C.

Elemental analysis of the product indicated the following:

Analysis: C$_{24}$H$_{18}$BrNO$_3$: Calculated: C, 64.28; H, 4.05; N, 3.12. Found: C, 64.31; H, 4.12; N, 3.08.

This compound is referred to hereinafter as Compound 258.

EXAMPLE LXXXVIII

Preparation of ethyl 3-[(3-chlorophenyl)amino]-2-methoxy-3-oxopropanoate

3-Chloroaniline (2.82 grams, 0.02 mole), mono-ethyl methoxymalonate (3.58 grams, 0.02 mole), prepared in Example LIII Part B, and 1,3-dicyclohexylcarbodiimide (4.50 grams, 0.02 mole) were reacted in a manner similar to that described in Example LVII to give 1.60 grams (0.006 mole) of ethyl 3-[(3-chlorophenyl)amino]-2-methoxy-3-oxopropanoate having melting point of 43.50° C.-46.50° C.

Elemental analysis of the product indicated the following:

Analysis: C$_{12}$H$_{14}$ClNO$_4$: Calculated: C, 53.05; N, 5.19; N, 5.16. Found: C, 52.83; H, 5.28; N, 5.38.

This compound is referred to hereinafter as Compound 259.

EXAMPLE LXXXIX

Preparation of ethyl 3-[(4-bromo-2-methylphenyl)amino]-2-methyl-2-methylthio-3-oxopropanoate Part A: Preparation of diethyl methyl(methylthio)malonate To a stirred solution of 3.0 grams (0.01 mole) of diethyl methylthiomalonate in 30 milliliters of DMF was added 0.35 gram (0.01 mole) of a 60% sodium hydride suspension in portions with cooling of the mixture to −15° C. to −20° C. Stirring at below −15° C. was continued until no more hydrogen was evolved following which 4.12 grams (0.03 mole) of methyl iodide were added dropwise, followed by two drops of 15-Crown-5. The cooling bath was then removed and the mixture allowed to warm to room temperature while stirring for an approximate 40-hour period. DMF was removed from the mixture under reduced pressure and the residue dissolved in ether and washed with water. The organic layer was then dried (MgSO$_4$), filtered and ether removed under reduced pressure. Removal of the product from the upper phase of the resulting two-phase mixture gave 1.08 grams (0.005 mole) of diethyl methyl(methylthio)malonate. NMR analysis of the product indicated the following:

'H NMR (CDCl$_3$) δ 1.10-1.48 (t, 6H, 2×CH$_3$), 1.67 (s, 3H, CH$_3$C), 2.19 (s, 3H, CH$_3$S) 4.04-4.50 (q, 2H, CH$_2$) ppm.

Part B: Preparation of ethyl (chlorocarbonylmethylthiopropionate

Diethyl methyl(methylthio)malonate (12.2 grams, 0.05 mole) was saponified with potassium hydroxide (3.1 grams, 0.05 mole) in a mixture of 120 milliliters of ethanol and 1.0 gram (0.05 mole) of water in a manner similar to that described in Example LIX and worked up in similar fashion to give 6.31 grams (0.03 mole) of the corresponding monocarboxylic acid mono ester. The entire sample of this mono ester was then stirred with 7.81 grams (0.065 mole) of thionyl chloride for a period of approximately 16 hours at room temperature. An additional 7.81 grams (0.065 of thionyl chloride were then added and stirring continued for about 22 hours following which unreacted thionyl chloride was stripped off under reduced pressure to give 6.74 grams (0.03 mole) of ethyl (chlorocarbonyl)methylthiopropionate as a liquid. NMR analysis of the product indicated the following:

'H NMR (CDCl$_3$) δ 1.21–1.56 (t, 6H, 2×CH$_3$), 1.82 (s, 3H, CH$_3$C)$_5$ 2.24 (s, 3H, CH$_3$S), 4.14–4.55 (q, 2H, CH$_2$)ppm.

Part C: Preparation of ethyl 3-[(4-bromo-2-methylphenyl)amino]-2-methyl-2-methylthio-3-oxopropanoate 4-Bromo-2-methylaniline (2.98 grams, 0.02 mole) and ethyl (chlorocarbonyl)methylthiopropionate (3.37 grams, 0.02 mole), prepared in Part B of this Example, were reacted in the presence of triethylamine (1.62 grams, 0.02 mole) in 200 milliliters of THF in a manner similar to that described in Example I to give 3.32 grams (0.009 mole) of ethyl 3-[(4-bromo-2-methylphenyl)amino]-2-methyl-2-methylthio-3-oxopropanoate as a yellow liquid containing some impurities as indicated by TLC.

Preparative plate chromatography gave a purer product sample for which elemental analysis indicated the following:

Analysis: C$_{14}$H$_{18}$BrNO$_3$S: Calculated: C, 46.67; H, 5.04. Found: C, 46.31; H, 5.17.

This compound is referred to hereinafter as Compound 260.

EXAMPLE XC

Preparation of ethyl 3[(3.5-dichlorophenyl)amino]-2-methyl-2-methylthio-3-oxopropanoate 3,5-Dichloroaniline, ethyl (chlorocarbonyl)methylthiopropanoate and triethylamine were reacted in a manner similar to that described in Example LXXXIX Part C to give ethyl 3-[(3,5-dichlorophenyl)amino]-2-methyl-2-methylthio-3-oxopropanoate as a yellow liquid.

Elemental analysis of the product indicated the following:

Analysis: C$_{13}$H$_{15}$Cl$_2$NO$_3$S: Calculated: C, 46.44; H, 4.50; N, 4.17. Found: C, 46.57; H, 4.53; N, 4.88.

This compound is referred to hereinafter as Compound 261.

EXAMPLE XCI

Preparation of ethyl 3-[(4-bromo-2-methylphenyl)amino]-2-formamido-3-oxopropanoate Part A: preparation of mono-ethyl formamidomalonate Diethyl formamidomalonate (25.0 grams, 0.12 mole) was saponified with potassium hydroxide (8.12 grams, 0.12 mole) in a solution of 500 milliliters of ethanol and 2.2 milliliters of water in a manner similar to that described in Example LIX. Solvents were evaporated away and the dry residue then dissolved in 300 milliliters of water and extracted with dichloromethane (3×200 milliliters). Acidification of the aqueous phase with HCl and continuous liquid-liquid extraction for a period of about 80 hours afforded 3.49 grams (0.01 mole) of mono-ethyl formamidomalonate as a white crystalline solid.

Part B: Preparation of ethyl 3-[(4-bromo-2-methylphenyl)amino]-2-formamido-3-oxopropanoate 4-Bromo-2-methylaniline (1.48 grams, 0.008 mole), mono-ethyl formamidomalonate (1.39 grams, 0.008 mole), prepared in Part A of this Example, and 1,3-dicyclohexylcarbodiimide (1.64 grams, 0.008 mole) were reacted in a manner similar to that described in Example LVII to give 0.53 gram (0.0015 mole) of ethyl 3-[(4-bromo-2-methylphenyl)amino]-2-formamido-3-oxopropanoate as white crystals having a melting point of 174.5° C.–176° C.

Elemental analysis of the product indicated the following:

Analysis: C$_{13}$H$_{15}$BrN$_2$O$_4$: Calculated: C, 45.50; H, 4.40; N, 8.16. Found: C, 45.18; H, 4.27; N, 7.82.

This compound is referred to hereinafter as Compound 262.

EXAMPLE XCII

Preparation of ethyl 3[(3,5-dichlorophenyl)amino]-2-formamido-3-oxopropanoate 3,5-Dichloroaniline, mono-ethyl formamidomalonate and 1,3-dicyclohexylcarbodiimide were reacted in a manner similer to that described in Example XCI Part B to give ethyl 3-[(3,5-dichlorophenyl)amino[-2-formamido-3-oxopropanoate having a melting point of 147.0° C.–148.0° C.

Elemental analysis of the product indicated the following:

Analysis: C$_{12}$H$_{12}$Cl$_2$N$_2$O$_4$: Calculated: C, 45.16; H, 3.79; N, 8.78. Found: C, 45.97; H, 4.39; N, 8.71.

This compound is referred to hereinafter as Compound 263.

EXAMPLE XCIII

Preparation of ethyl 3[(4-bromo-2-methylphenyl)amino]-2-methyl-2-methylsulfonyl-3-oxopropanoate A solution of 2.1 grams (0.006 mole) of ethyl 3-[(4-bromo-2-methylphenyl)amino]-2-methyl-2-methylthio-3-oxopropanoate and one drop of Aliquat 336 in 100 milliters of dichloromethane was stirred vigorously, with cooling to 0° C.–5° C., while adding dropwise a 5.2% aqueous solution of sodium hypochlorite (0.46 gram, 0.006 mole). Stirring was conducted for 2 hours following the feed and the reaction mixture examined by thin-layer chromatography. Since a considerable amount of methylthio starting material was still present an additional 1.65 -gram portion of the hypochlorite solution was added and the mixture stirred overnight. Over the ensuing period of approximately 18 hours, three additional 1.65-gram portions of the aqueous NaOCL solution plus two drops of Aliquat 336 were added with vigorous stirring and cooling at 0° C. -5° C. As TLC indicated essential completion of the raction the organic layer was decanted off, washed with water (2×), dried over MgSO$_4$, filtered and flash evaporated. A 0.74-gram (0.002 mole) fraction of ethyl 3-[(4-bromo-2-methylphenyl)amino]-2-methyl-2-methylsulfonyl-3-oxopropanoate was recovered by flash chromatography.

Preparative plate chromatography gave a purer product sample of the oil for which elemental analysis indicated the following:

Analysis: C$_{14}$H$_{18}$BrNO$_5$S: Calculated: C, 42.87; H, 4.62; O, 20.39. Found: C, 42.85; H, 4.61; O, 20.03.

This compound is referred to hereinafter as Compound 264.

EXAMPLE XCIV

Preparation of ethyl 3-[(3,5-dichlorophenyl)amino]-2-methyl-2-methylsulfinyl-3-oxopropanoate Ethyl 3-[(3,5-dichlorophenyl)amino]-2-methyl-2-methylthio-3-oxopropanoate, prepared in Example XC (Compound 261), was reacted with aqueous sodium hypochlorite in a water-methylene chloride mixture in a manner similar to that described in Example XCIII to give ethyl 3-[(3,5-dichlorophenyl)amino]-2-methyl-2-methylsulfinyl-3-oxopropanoate having a melting point of 124° C.–127° C.

Elemental analysis of the product indicated the following:

Analysis: $C_{13}H_{15}Cl_2NO_4S$: Calculated: C, 44.33; H, 4.29; O, 18.17. Found: C, 44.69; H, 4.33; O, 17.74.

This compound is referred to hereinafter as Compound 265.

EXAMPLE XCV

In a manner similar to that employed in Example XL other compounds were prepared employing Compound 236 (Example LXXIII) as the starting material. The structures and analytical data for Comounds 266 through 270 are set forth in Table Q below.

TABLE Q

Representative Malonic Acid Derivative Compounds

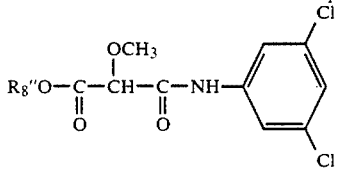

| Compound No. | Substituent $R_8''$ | Calculated C | H | N | Found C | H | N | Melting Point °C. |
|---|---|---|---|---|---|---|---|---|
| 266 | $(CH_3)_2CH-$ | 48.76 | 4.72 | 4.38 | 48.94 | 4.70 | 4.44 | 85–87.5 |
| 267 | ⟨S⟩ | 53.34 | 5.32 | 3.89 | 53.40 | 5.45 | 3.89 | 77–80 |
| 268 | $CH_3(CH_2)_4-$ | 51.73 | 5.50 | 4.02 | 51.57 | 5.56 | 4.02 | 43.5–45 |
| 269 | $CH_3(CH_2)_7-$ | NMR (CDCl$_3$): δ 0.55–2.03(m, 15H), 3.58(s, 3H), 4.13–4.45(t, 2H), 4.46(s, H), 7.12–7.66(m, 3H), 8.45(br s, H)ppm. | | | | | | Oil |
| 270 | $CH_3(CH_2)_9-$ | NMR (CDCl$_3$): δ 0.64–2.00(m, 19H), 3.57(s, 3H), 4.14–4.40(t, 2H), 4.44(s, H), 7.14–7.71(m, 3H), 8.49(br s, H)ppm. | | | | | | Oil |

EXAMPLE XCVI

Preparation of methyl 1-(4-bromo-2-methylphenylaminocarbonyl)-2-n-propyl-cyclopropanecarboxylate Part A: Preparation of dimethyl 2-(n-propyl)cyclopropane-1,1-dicarboxylate A solution of 50.0 grams (0.71 mole) of 1-pentene and 10.0 grams (0.06 mole) of dimethyl diazomalonate in 256 milliliters of hexafluorobenzene was degassed by bubbling in nitrogen for 30 minute and then photolyzed, for a period of approximately 68 hours, at room temperature, in the presence of a 100-watt Hanovia mercury lamp. At the end of this period the diazo peak at 2120 cm$^{-1}$ had dissappeared from the infrared spectrum. The reaction mixture was carefully distilled though a Vigreux column at atmospheric pressure, removing 297.8 grams of a mixture of unreacted 1-pentene and solvent overhead to a final head temperature of about 80° C., and leaving 22.58 grams of orange liquid residue. The latter was worked up by silica column chromatography to give 6.06 grams (0.03 mole) of dimethyl 2-(n-propyl)-cyclopropane-1,1-dicarboxylate.

NMR analysis of the product indicated the following: "H NMR (CDCl$_3$): δ 0.80–2.70 (m, 10H), 3.79 (s, 3H, CH$_3$O), 3.81 (s, 3H, CH$_3$O), ppm.

Part B: Preparation of mono-metyl 2-(n-propyl)cyclopropane-1,1-dicarboxylate

The 6.06-gram (0.03 mole) portion of dimethyl ester from Part A, above, was saponified by treatment with 1.21 grams (0.03 mole) of sodium hydroxide in a solution of 60 milliliters of methanol containing 6 milliliters of water and worked up in a manner similar to that described in Example VII to give 4.93 grams (0.026 mole) of mono-methyl 2-(n-propyl)cyclopropane-1,1-dicarboxylate as a light yellow oil. NMR analysis of the product indicated the following:

'H NMR (CDCl$_3$): δ 0.70–2.30(m, 10H), 3.80 (s, 3H, CH$_3$O), 10.5 (s, 1H, CO$_2$H) ppm.

Part C: Preparation of methyl 1-(4-bromo-2methyl-phenylaminocarbonyl)2-n-propylcyclopropanecarboxylate Mono-methyl 2-(n-propyl)cyclopropane-1,1-dicarboxylate (2.47 grams, 0.013 mole) from Part B, above, ethyl chloroformate (1.44 grams, 0.013 mole) and 4-bromo-2-methylaniline (2.48 grams, 0.013 mole) were reacted sequentially in the presence of triethylamine (1.35 grams, 0.013 mole) in a manner similar to that described in Example XXXIII to give 2.43 grams (0.007 mole) of methyl 1-(4-bromo-2-methyl-phenylaminocarbonyl)-2-n-propylcyclopropanecarb oxylate having a melting point of 60° C.–≠66° C.

Elemental analysis of the product indicated the following:

Analysis: $C_{16}H_{20}BrNO_3$: Calculated: C, 54.25; N, 5.69; N, 3.95. Found: C, 54.18; H, 6.15; N, 3.61.

This compound is referred to hereinafter as Compound 271.

EXAMPLE XCVII

Preparation of methyl 7-(4-bromo-2-methylphenylamino-carbonyl)bicyclo[4.1.0.]heptane-7-carboxylate Part A: Preparation of dimethyl bicyclo [4.1.0]heptane-2,7-dicarboxylate To stirred, refluxing mixture of 100.0 grams (1.22 mole) of cyclohexene and 0.037 gram (0.0001 mole) of cupric acetylacetonate was fed 22.7 grams (0.14 mole) of dimethyl diazomalonate over a 25-hour period by means of a syringe pump. Refluxing was continued for an additional 8 hours after which distillation of the reaction mixture was begun, employing a small Vigreux column. After removing about 32 grams of cyclohexene overhead, to a head temperature of 80° C., the residue was allowed to cool. The solidified residue was worked up by flash column chromatography on silica gel to give 17.53 grams (0.08 mole) of dimethyl bicyclo[4.1.0-]heptane-7,7-dicarboxylate having a melting point of 83° C.-86° C.

Elemental analysis of the product indicated the following:

Analysis: $C_{11}H_{16}O_4$: Calculated: C, 62.25; H, 7.60. Found: C, 61.88; H, 7.69.

Part B: Preparation of mono-methyl bicyclo[4.1.0] heptane-7,7-dicarboxylate

A 16.44-gram (0.08 mole) portion of the dimethyl ester from Part A was saponified by treatment with 3.20 grams (0.08 mole) of sodium hydroxide in a solution of 160 milliliters of methanol containing 16 milliliters of water and worked up in a manner similar to that described in Example VII to give 13.35 grams (0.07 mole) of monomethyl bicyclo[4.1.0]heptane-7,7-dicarboxylate having a melting point of 114° C.-117° C.

Elemental analysis of the product indicated the following:

Analysis: $C_{10}H_{14}O_4$: Calculated: C, 60.59; H, 7.12. Found: C, 61.92; N, 7.58.

Part C: Preparation of methyl 7-(4-bromo-2-methyl-phenylaminocarbonyl)bicyclo[4.1.0]heptane-7-carboxylate Mono-methyl bicyclo[4.1.0]heptane-7,7-dicarboxylate (5.0 grams, 0.025 mole) from Part B of this example, ethyl chloroformate (2.49 grams, 0.025 mole) were reacted sequentially in the presence of 2.55 grams (0.025 mole) of triethylamine in a manner similar to that described in Example XXXIII to give 3.32 grams (0.009 mole) of methyl 7-(4-bromo-2-methyl-phenylaminocarbonyl)bicyclo[4.1.0]heptane-7-carboxylate having a melting point of 105° C.-107° C.

Elemental analysis of the product indicated the following:

Analysis: $C_{17}H_{20}BrNO_3$: Calculated: C, 55.75; H, 5.50; N, 3.82. Found: C, 56.20; H, 5.71; N, 3.74.

This compound is referred to hereinafter as Compound 272.

EXAMPLE XCVIII

Preparation of methyl 1-(4-bromo-2-methylphenylaminocarbonyl)-2,2,3,4-tetramethylcyclopropanecarboxylate Part A: Preparation of dimethyl 2,2,3,3-tetramethyl-cyclopropane dicarboxylate A mixture of 20.0 grams (0.13 mole) of dimethyl diazomalonate and 164.35 grams (1.95 moles) of 2,3-dimethyl-2-butene was photolyzed at room temperature for a period of approximately 47 hours in the presence of a 100-watt Hanovia mercury lamp. Most of the unreacted 2,3-dimethyl-2-butene was removed by distillation, at atmospheric pressure, to a head temperature of 73° C. and the still residue was subjected to flash chromatography on a silica gel column to give 9.00 grams (0.04 mole) of dimethyl 2,2,3,3-tetramethylcyclopropanedicarboxylate. NMR analysis of the product indicated the following:

'H NMR (CDCl$_3$): δ 1.27 (s, 12H, CH$_2$—C), 3.74 (s, 6H, CH$_3$D)ppm.

Part B: Preparation of methyl 1-chlorocarbonyl-2,2,3,3-tetramethylcyclopropanecarboxylate A 7.67-gram (0.036 mole) portion of the dimethyl ester from Part A, above, was saponified by contact with a solution of 1.58 grams (0.04 mole) of sodium hydroxide in 60 milliliters of methanol containing 7 milliliters of water and worked up in a manner similar to that described in Example VII to give 5.75 grams (0.029 mole) of the corresponding mono-methyl ester acid. A 2.32-gram (0.01 mole) amount of the latter was converted to its sodium salt by contact with 0.46 gram (0.01 mole) of sodium hydroxide dissolved in a mixture of 25 milliliters of methanol and 30 milliliters of water. The salt solution was evaporated under reduced pressure and remaining water removed by azeotropic distillation with benzene giving 2.48 grams (0.01 mole) of the dry sodium salt. This salt was slurried with approximately 60 milliliters of benzene, and with stirring and cooling to 0° C.-5° C., a solution of 5.7 grams (0.045 moles) of oxalyl chloride in 20 milliliters of benzene was then fed in. Stirring in the ice bath was continued for one hour after which the cooling was discontinued. Pyridine (4 drops) was added to the stirring mixture. Stirring was continued for approximately 22 hours. Five more drops of pyridine were then added and the reaction mixture stirred at room temperature for about 22 hours, then for 2 hours at 50° C., for 16 more hours at room temperature and then at 55° C. for a 2-hour period. Additional portions of oxalyl chloride (2 milliliters ) and pyridine (5drops) were added to the reaction mixture which was then stirred at 55° C. for one hour and then for approximately 16 hours at ambient temperature. The reaction mixture as then freed of solvent to give 2.45 grams (0.01 mole) of methyl 1-chlorocarbonyl-2,2,3,3-tetramethylcyclopropanecarboxylate. NMR analysis of the product indicated the following:

'H NMR (CDCl$_3$): δ1.31 (S, 12H, CH$_3$C), 3.81 (s, 3H, CH$_3$O) ppm.

Part C: Preparation of methyl 1-(4-bromo-2-methyl-phenylaminocarbonyl)-2,2,3,3-tetramethylcyclopropanecarboxylate 4-Bromo-2-methylaniline (2.09 grams, 0.01 mole) and methyl 1-chlorocarbonyl-2,2,3,3-tetramethylcyclopropanecarboxylate (2.45 grams, 0.01 mole), prepared in Part B, were reacted in the presence of 1.13 grams (0.01 mole) of triethylamine in 70 milliliters of benzene solution in a manner similar to that described in Example I to give 2.13 grams (0.006 mole) of methyl 1-(4-bromo-2-methylphenylamino-carbonyl)-2,2,3,3-tetramethylcyclopropaneca rboxylate.

Elemental analysts of the product indicated the following:

Analysis: $C_{17}H_{22}BrNO_3$: Calculated: C, 55.44; H, 6.02; N, 3.80. Found: C, 55.76; H, 5.94; N, 3.81.

This compound is referred to hereinafter as Compound 273.

EXAMPLE XCIX

Preparation of methyl 1-(4-bromo-2-methylphenylaminocarbonyl)-2,3-dimethyl-2-cyclopropenecarboxylate Part A: Preparation of dimethyl 2,3-dimethyl-2-cyclopropene-1,1-dicarboxylate A nitrogen-degassed solution of 37.5 grams (0.69 mole) of 2-butyne and 20.0 grams (0.13 mole) of dimethyl diazomalonate in approximately 325 grams of hexafluorobenzene was photolyzed for approximately 100 hours, at 0° C.-5° C., employing a 100-watt Hanovia mercury lamp in a manner similar to that described in Example XCVI Part A. Similar workup of the reaction mixture afforded 10.8 grams (0.06 mole) of dimethyl 2,3-dimethyl-2-cyclopropene-1,1-dicarboxylate. NMR analysis of the product indicated the following:

'H NMR (CDCl$_3$): δ 2.10 (s, 6H, CH$_3$C), 3.77 (s, 6H, CH$_3$O) ppm.

Part B: Preparation of met;hyl 1-(4-bromo-2-methylphenylamino-carbonyl)-2,3-dimethyl-2,3-dimethyl-2-cyclopropenecarboxylate A 5.48-gram (0.03 mole) sample of dimethyl 2,3-dimethyl-2-cyclopropene-1,1-dicarboxylate (Part A, above) as saponified by treatment with 1.32 grams (0.03 mole) of sodium hydroxide in a mixture of 50 milliliters of methanol and 5 milliliters of water and worked up in a manner similar to that described in Example VII to give mono-methyl 2,3-dimethyl-2-cyclopropene-1,1-dicarboxylate having a melting point of 64° C.-65.5° C. The combined fractions of the mono-methyl ester, weight 2.2 grams (0.013 mole), were then reacted with 1.47 grams (0.014 mole) of ethyl chloroformate and 2.40 grams (0.013 mole) of 4-bromo-2-methylaniline, sequentially in the presence of 3.93 grams (0.03 mole) of anhydrous potassium carbonate and 500 milligrams of 18-crown-6 in tetrahydrofuran solution in a manner similar to that described in Example LXXXV Parts D and E to give 2.55 grams (0.007 mole) of methyl 1-(4-bromo-2-methylphenylaminecarbonyl)-2,3-dimethyl-2-cyclopropenecarboxylate having a melting point of 125.5° C.-127° C.

Elemental analysis of the product indicated the following:

Analysis: $C_{15}H_{16}BrNO_3$: Calculated: C, 53.27; H, 4.77; N, 4.13. Found: C. 53.15; H, 5.06; N, 3.98.

This compound is referred to hereinafter as Compound 274.

EXAMPLE C

Preparation of methyl 1-(4-bromo-2-methylphenylamino-carbonyl)-2,3-di-n-propyl-2-cyclopropenecarboxylate 4-Octyne and dimethyl diazomalonate were reacted in the presence of cupric acetylacetonate in a manner similar to that described in Example XCVII Part A to give dimethyl 2,3-di-n-propyl-2-cyclopropene-1,1-dicarboxylate which was saponified to give mono-methyl 2,3-di-n-propyl-2-cyclopropene-1,1-dicarboxylate and worked up by the general procedure of Example XCVII Part B. Reaction of the latter mono-methyl ester in sequence with ethyl chloroformate and 4-bromo-2-methylaniline, in the presence of potassium carbonate and 18-crown-6, in a manner similar to that described in Example XCIX Part B to give methyl 1-(4-bromo-2-methylphenyl-aminocarbonyl)-2,3-di-n-propyl-2-cyclopropenecarboxylate having a melting point of 52° C.-54° C.

Elemental analysis of the product indicated the following:

Analysis: $C_{19}H_{24}BrNO_3$: Calculated: C, 57.88; N, 6.13; N, 3.55. Found: C, 57.85; H, 6.19; N, 3.22.

This compound is referred to hereinafter as Compound 275.

EXAMPLE CI

The methyl esters numbers 271 through 275, described, respectively in Examples XCVI through C, were saponified and worked up in a manner similar to that described in Example XCVI Part B to give the series of corresponding monocarboxylic acids hereinafter referred to as Compounds 276 through 280. The structures and analytical data for these compounds are set forth in Table R below.

TABLE R

Representative Malonic Acid Derivative Compounds

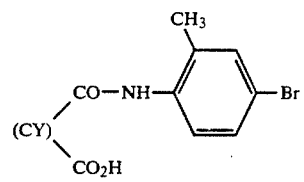

| Compound No. | Substituent (CY) | Calculated C | Calculated H | Calculated N | Found C | Found H | Found N | Melting Point °C. |
|---|---|---|---|---|---|---|---|---|
| 276 | n-C$_3$H$_7$ 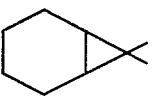 | 52.95 | 5.33 | 4.12 | 52.65 | 5.32 | 3.93 | 147-149 |
| 277 |  | 51.91$^{(a)}$ | 5.44$^{(a)}$ | — | 52.17 | 5.67 | — | 167-169 |

TABLE R-continued

Representative Malonic Acid Derivative Compounds

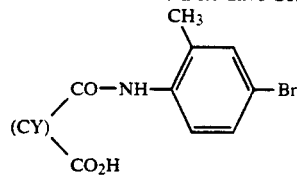

| Compound No. | Substituent (CY) | Elemental Analysis Calculated | | | Found | | | Melting Point °C. |
|---|---|---|---|---|---|---|---|---|
| | | C | H | N | C | H | N | |
| 278 | CH3, CH3, CH3, CH3 | 51.62[a] | 5.96[a] | 3.76[a] | 51.15 | 6.15 | 3.25 | 184–185 |
| 279 | CH3, CH3 | 51.87 | 4.35 | 4.32 | 52.09 | 4.38 | 4.26 | 174–7(dec.) |
| 280 | n-C3H7, n-C3H7 | 56.85 | 5.85 | 3.68 | 56.64 | 5.84 | 3.56 | 95–97 |

[a]Calculated as the monohydrate.

EXAMPLE CII

In a manner similar to that employed in Example XXXIII other compounds were prepared. The structures and analytical data for Compounds 281 through 284 are set forth in Table S below.

TABLE S

Representative Malonic Acid Derivative Compounds

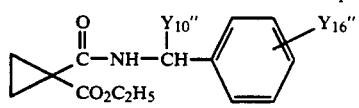

| Compound No. | Substituent | | Elemental Analysis Calculated | | | Found | | | Melting Point °C. |
|---|---|---|---|---|---|---|---|---|---|
| | $Y_{10}''$ | $Z_{16}''$ | C | H | N | C | H | N | |
| 281 | H | 2,4-Cl2 | 53.18 | 4.78 | 4.43 | 53.38 | 4.81 | 4.40 | 77–80 |
| 282 | H | 4-Br | 51.71 | 6.65 | 4.31 | 51.59 | 4.96 | 4.38 | Oil |
| 283 | H | 3,4-Cl2 | 53.18 | 4.78 | 4.43 | 52.42 | 4.64 | 4.48 | Oil |
| 284 | CH3 | H | 68.94 | 7.33 | 5.36 | 68.42 | 7.48 | 4.95 | Oil |

EXAMPLE CIII

In a manner similar to that employed in Example VII other compounds were prepared. The structures and analytical data for Compounds 285 through 288 are set forth in Table T below.

TABLE T

Representative Malonic Acid Derivative Compounds

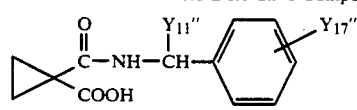

| Compound No. | Substituent | | Elemental Analysis Calculated | | | Found | | | Melting Point °C. |
|---|---|---|---|---|---|---|---|---|---|
| | $Y_{11}''$ | $Z_{17}''$ | C | H | N | C | H | N | |
| 285 | H | 2,4-Cl2 | 50.02 | 3.85 | 4.86 | 50.03 | 3.84 | 4.77 | 199–200 |
| 286 | H | 4-Br | 48.34 | 4.06 | 4.70 | 48.22 | 4.32 | 4.62 | 187.5–189 |
| 287 | H | 3,4-Cl2 | 50.02 | 3.85 | 4.86 | 49.94 | 3.98 | 4.57 | 195–197 |
| 288 | CH3 | H | 66.94 | 6.48 | 6.01 | 66.93 | 6.60 | 5.97 | 151.5–153 |

EXAMPLE CIV

Preparation of N-(4-bromo-2-methylphenyl)-2-ethoxycarbonyl-3-methyloxiranecarboxamide Part A: Preparation of diethyl 3-methyloxirane-2,2-dicarboxylate A mixture of 50 grams (0.27 mole) of diethyl ethylidenemalonate, 455 grams (4.02 moles) of 30% hydrogen peroxide, 17.6 gram (0.053 mole) of sodium tungstate dihydrate and 400 milliliters of ethanol was stirred and heated at 80° C. for one hour, cooled to room temperature and stirred for an additional hour. Ethanol was removed under reduced pressure and the produce extracted into dichloromethane (3×200 milliliters), the extract then water-washed, dried (MgSO4), filtered and solvent removed to give the crude product. Vacuum distillation gave 40.45 grams (0.20 mole) of diethyl 3-methyloxirane-2,2-dicarboxylate having a boiling point of 120° C. at 4millimeters of Hg.

NMR analysis of the product indicated the following: 'H NMR (CDCl3): δ 1.14–150 (m, 9H, 3×CH3), 3.43–3.78 (q, H, CH), 4.07–4.57 (m, 4H, 2×CH2) ppm.

Part B: Preparation of ethyl 2-carboxy-3-methyloxiranecarboxylate

A 38.25-gram (0.19 mole) portion of diethyl 3-methyloxirane-2,2-dicarboxylate from Part A, above, was saponified with potassium hydroxide (10.61 grams of 85 percent solid, 0.19 mole) in a mixture of 380 milliliters of ethanol and 3.41 grams (0.19 mole) of water in a manner similar to that described in Example VII but employing a saponification period of 3 hours. Following the acidification procedure, the product was recovered by extraction with dichloromethane giving 20.33 grams (0.12 mole) of ethyl 2-carboxy-3-methyloxiranecarboxylate as a light yellow liquid. NMR analysis of the produce indicated the following: 'H NMR (CDCl3) δ 1.20–1.61 (m, 6H, 2×CH3), 3.48–3.93 (m, H, CH), 4.19–4.64 (q, 2H, CH2), 9.55 (s, H, CO2H) ppm.

Part C: Preparation of N-(4-bromo-2-methylphenyl-2-ethoxycarbonyl-3-methyloxiranecarboxamide Ethyl 2-carboxy-3-methyloxiranecarboxylate (5.09 grams, 0.03 mole), prepared in Part B, 4-bromo-2-methylaniline (5.44 grams, 0.03 mole) and 1,3-dicyclohexylcarbodiimide (6.03 grams, 0.03 mole) were reacted in a manner similar to that described in Example LVII to give 4.72 grams (0.014 mole) of N-(4-bromo-2-methylphenyl)-2-ethoxycarbonyl-3-methyloxiranecarboxamide having a melting point of 57° C.–60° C.

Elemental analysis of the product indicated the following:

Analysis: $C_{14}H_{16}BrNO_4$: Calculated: C, 49.14; H, 4.71; N, 4.09. Found: C, 49.18; N, 4.87; N, 4.09.

This compound is referred to hereinafter as Compound 289 and is represented by:

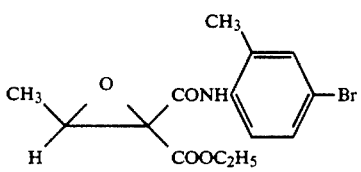

EXAMPLE CV

Preparation of N-(4-bromo-2-methylphenyl)-2-carboxy-3-methyloxiranecarboxamide

A 2.72-gram (0.008 mole) portion of N-(4-bromo-2-methylphenyl)2-ethoxycarbonyl-3-methyloxiranecarboxamide, prepared in the preceding Example CIV, was hydrolyzed in a manner similar to that described in Example VII to give 1.5 grams (0.005 mole) of N-(4-bromo-2-methylphenyl)-2-carboxy-3-methyloxiranecaboxamide having a melting point of 143° C.–148°

C. NMR analysis of the product indicated the following:

'H NMR (d6 acetone) δ 1.45 (d, 3H, J = 5 Hz), 2.29 (s, 3H, CH3) 7.23–7.78 (m, 3H, phenyl), 9.25 (br s, H, NH) ppm. This compound is referred to hereinafter as Compound 290 and is represented by:

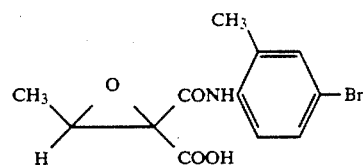

EXAMPLE CVI

Effect of Representative Synergistic Compositions on Defoliation of Snapbean Plants Solutions of the test compounds and compositions identified in Table U below were prepared by dissolving the compounds in acetone/water (50:50 volume/volume) containing 0.1 percent volume/volume of Triton X-100 surfactant commercially available from Rhom and Haas Company, Philadelphia, Pa. As detailed below, these solutions of the test compounds and compositions were applied to snapbean plants at a concentration of 0.25 pounds of each active ingredient per acre or 0.50 pounds of each active ingredient per acre. The compositions were applied to the snapbean plants as a mixture. Ethephon is commercially available from Union Carbide Agricultural Products Company, Inc., Research Triangle Park, N.C.

Into 13.5 centimeter diameter plastic pots containing a potting soil mix, i.e., one-third sandy loam soil, one-third peat moss and one-third perlite by volume, were sown three snapbean seeds (Phaseoplus vulgaris var. Cranberry). Five to seven days after planting, the plants were thinned to one plant per pot. Ten to fourteen days after planting at the time of full expansion of the primary leaves, each concentration of the test compounds and compositions identified in Table U (each pot sprayed with a volume equivalent to 180 gallons per acre) was applied to three snapbean plants as a foliar spray by use of an aspirated spray apparatus set at 10 psig air pressure. As a control, a water-acetone solution containing no test compound or composition was also sprayed on three snapbean plants. When dry, all of the plants were placed in a greenhouse at a temperature of 80°F.±5° F. and humidity of 50 percent±5 percent. At 96 hours after treatment, percent defoliation of the snapbean plants was determined by visual observation. The values obtained for the control and each test compound and composition were averaged to obtain the results in Table U.

TABLE U

| Effect of Representative Synergistic Compositions on Defoliation of Snapbean Plants | | |
|---|---|---|
| Compound/ Composition Identification | Rate (Pounds per Acre) | Percent Defoliation |
| Control | — | 0 |
| Ethephon | 0.25 | 0 |
|  | 0.50 | 21 |
| Compound 75 | 0.25 | 0 |
|  | 0.50 | 0 |
| Ethephon + Compound 75 | 0.25 + 0.25 | 52 |
|  | 0.50 + 0.50 | 70 |

TABLE U-continued
Effect of Representative Synergistic Compositions on Defoliation of Snapbean Plants

| Compound/ Composition Identification | Rate (Pounds per Acre) | Percent Defoliation |
|---|---|---|
| Compound 5 | 0.25 | 0 |
|  | 0.50 | 0 |
| Ethephon + Compound 5 | 0.25 + 0.25 | 23 |
|  | 0.50 + 0.50 | 27 |
| Compound 111 | 0.25 | 0 |
|  | 0.50 | 0 |
| Ethephon + Compound 111 | 0.25 + 0.25 | 93 |
|  | 0.50 + 0.50 | 97 |
| Compound 25 | 0.25 | 0 |
|  | 0.50 | 0 |
| Ethephon & Compound 25 | 0.25 + 0.25 | 24 |
|  | 0.50 + 0.50 | 40 |
| Compound 50 | 0.25 | 0 |
|  | 0.50 | 0 |
| Ethephon + Compound 50 | 0.25 + 0.25 | 52 |
|  | 0.50 + 0.50 | 37 |
| Compound 96 | 0.25 | 0 |
|  | 0.50 | 0 |
| Ethephon + Compound 96 | 0.25 + 0.25 | 17 |
|  | 0.50 + 0.50 | 37 |
| Compound 126 | 0.25 | 0 |
|  | 0.50 | 0 |
| Ethephon + Compound 126 | 0.25 + 0.25 | 82 |
|  | 0.50 + 0.50 | 100 |
| Compound 128 | 0.25 | 0 |
|  | 0.50 | 0 |
| Ethephon + Compound 128 | 0.25 + 0.25 | 47 |
|  | 0.50 + 0.50 | 50 |
| Compound 112 | 0.25 | 0 |
|  | 0.50 | 0 |
| Ethephon + Compound 112 | 0.25 + 0.25 | 77 |
|  | 0.50 + 0.50 | 40 |
| Compound 80 | 0.25 | 0 |
|  | 0.50 | 0 |
| Ethephon + Compound 80 | 0.25 + 0.25 | 47 |
|  | 0.50 + 0.50 | 27 |
| Compound 113 | 0.25 | 0 |
|  | 0.50 | 0 |
| Ethephon + Compound 113 | 0.25 + 0.25 | — |
|  | 0.50 + 0.50 | 23 |
| Compound 114 | 0.25 | 0 |
|  | 0.50 | 0 |
| Ethephon + Compound 114 | 0.25 + 0.25 | — |
|  | 0.50 + 0.50 | 97 |
| Compound 82 | 0.25 | 0 |
|  | 0.50 | 0 |
| Ethephon + Compound 82 | 0.25 + 0.25 | — |
|  | 0.50 + 0.50 | 60 |
| Compound 115 | 0.25 | 0 |
|  | 0.50 | 0 |
| Ethephon + Compound 115 | 0.25 + 0.25 | — |
|  | 0.50 + 0.50 | 93 |
| Compound 46 | 0.25 | 0 |
|  | 0.50 | 0 |
| Ethephon + Compound 46 | 0.25 + 0.25 | — |
|  | 0.50 + 0.50 | 27 |
| Compound 116 | 0.25 | 0 |
|  | 0.50 | 0 |
| Ethephon + Compound 116 | 0.25 + 0.25 | — |
|  | 0.50 + 0.50 | 87 |
| Compound 117 | 0.25 | 0 |
|  | 0.50 | 0 |
| Ethephon + Compound 117 | 0.25 + 0.25 | — |
|  | 0.50 + 0.50 | 97 |
| Compound 97 | 0.25 | 0 |
|  | 0.50 | 0 |
| Ethephon + Compound 97 | 0.25 + 0.25 | — |
|  | 0.50 + 0.50 | 30 |
| Compound 149 | 0.25 | 0 |
|  | 0.50 | 0 |
| Ethephon + Compound 149 | 0.25 + 0.25 | — |
|  | 0.50 + 0.50 | 40 |
| Compound 129 | 0.25 | 0 |
|  | 0.50 | 0 |
| Ethephon + Compound 129 | 0.25 + 0.25 | — |
|  | 0.50 + 0.50 | 73 |
| Compound 37 | 0.25 | 0 |
|  | 0.50 | 0 |
| Ethephon + Compound 37 | 0.25 + 0.25 | — |
|  | 0.50 + 0.50 | 67 |
| Compound 88 | 0.25 | 0 |
|  | 0.50 | 0 |
| Ethephon + Compound 88 | 0.25 + 0.25 | — |
|  | 0.50 + 0.50 | 40 |
| Compound 90 | 0.25 | 0 |
|  | 0.50 | 0 |
| Ethephon + Compound 90 | 0.25 + 0.25 | — |
|  | 0.50 + 0.50 | 30 |
| Compound 120 | 0.25 | 0 |
|  | 0.50 | 0 |
| Ethephon + Compound 120 | 0.25 + 0.25 | — |
|  | 0.50 + 0.50 | 30 |
| Compound 121 | 0.25 | 0 |
|  | 0.50 | 0 |
| Ethephon + Compound 121 | 0.25 + 0.25 | — |
|  | 0.50 + 0.50 | 60 |
| Compound 122 | 0.25 | 0 |
|  | 0.50 | 0 |
| Ethephon + Compound 122 | 0.25 + 0.25 | — |
|  | 0.50 + 0.50 | 37 |
| Compound 123 | 0.25 | 0 |
|  | 0.50 | 0 |
| Ethephon + Compound 123 | 0.25 + 0.25 | — |
|  | 0.50 + 0.50 | 86 |
| Compound 96 | 0.25 | 0 |
|  | 0.50 | 0 |
| Ethephon + Compound 96 | 0.25 + 0.25 | 74 |
|  | 0.50 + 0.50 | 83 |
| Compound 97 | 0.25 | 0 |
|  | 0.50 | 0 |
| Ethephon + Compound 97 | 0.25 + 0.25 | — |
|  | 0.50 + 0.50 | 63 |
| Compound 289 | 0.50 | 0 |
| Ethephon + Compound 289 | 0.25 + 0.25 | 20 |
|  | 0.50 + 0.50 | 83 |
| Ethephon + Compound 184 | 0.25 + 0.25 | 26 |
| Compound 184 | 0.5 | — |
| Ethephon + Compound 186 | 0.25 + 0.25 | 50 |
| Compound 186 | 0.5 | 0 |
| Ethephon + Compound 196 | 0.5 + 0.5 | 66 |
| Compound 196 | 0.5 | 10 |
| Ethephon + Compound 215 | 0.5 + 0.5 | 17 |
| Compound 215 | 0.5 | — |
| Ethephon + Compound 217 | 0.5 + 0.5 | 10 |
| Compound 217 | 0.5 | 0 |
| Ethephon + Compound 221 | 0.25 + 0.25 | 27 |
| Compound 221 | 0.5 | 0 |
| Ethephon + Compound 222 | 0.5 + 0.5 | 27 |
| Compound 222 | 0.5 | 0 |
| Ethephon + Compound 231 | 0.5 + 0.5 | 23 |
| Compound 231 | 0.5 | — |
| Ethephon + Compound 233 | 0.5 + 0.5 | 60 |
| Compound 233 | 0.5 | 10 |
| Ethephon + Compound 235 | 0.5 + 0.5 | 10 |
| Compound 235 | 0.5 | 0 |
| Ethephon + Compound 237 | 0.5 + 0.5 | 10 |
| Compound 237 | 0.5 | 0 |
| Ethephon + Compound 243 | 0.5 + 0.5 | 67 |
| Compound 243 | 0.5 | 0 |

The results in Table U demonstrate that compositions containing ethephon and a malonic acid derivative compound provide a synergistic effect on defoliation of snapbean plants.

EXAMPLE CVII

Effect of Representative Synergistic Compositions on Defoliation of Snapbean Plants In a manner similar to the procedure described in Example XXVIII, the defoliation effect on snapbean plants was determined for representative synergistic compositions at various rates of application except that percent defoliation of the snapbean plants was determined at 72 hours after treatment. The results of these tests are set forth in Table V below.

TABLE V

Effect of Representative Synergistic Compositions on Defoliation of Snapbean Plants

| Compound/ Composition Identification | Rate (Pounds per Acre) | Percent Defoliation |
|---|---|---|
| Control | — | 0 |
| Ethephon | 0.25 | 0 |
| Compound 96 | 0.25 | 0 |
| Ethephon + Compound 96 | 0.25 + 0.25 | 80 |
| Ethephon | 0.50 | 0 |
| Compund 96 | 0.50 | 0 |
| Ethephon + Compound 96 | 0.50 + 0.50 | 90 |
| Ethephon | 0.25 | 0 |
| Compound 96 | 0.50 | 0 |
| Ethephon + Compound 96 | 0.25 + 0.50 | 83 |
| Ethephon | 0.50 | 0 |
| Compound 96 | 9.25 | 0 |
| Ethephon + Compound 96 | 0.50 + 0.25 | 90 |
| Ethephon | 0.75 | 13 |
| Compound 75 | 1.0 | 0 |
| Ethephon + Compound 75 | 0.75 + 1.0 | 83 |

The results of Table V demonstrate that compositions containing ethephon and a malonic acid derivative compound provide a synergistic effect on defoliation of snapbean plants.

EXAMPLE CVIII

Effect of Combination/Sequential Applications of Representative Synergistic Compositions on Defoliation of Snapbean Plants In a manner similar to the procedure described in Example XXVIII, the defoliation effect on snapbean plants was determined for representative synergistic compositions using both combination (tank mix) and sequential application methods. In the sequential application method, the second compound was applied 78 hours after the first compound. The results of these tests are set forth in Table W below.

TABLE W

Effect of Combination/Sequential Applications of Representative Synergistic Compositions on Defoliation of Snapbean Plants

| Compound/ Composition Identification | Rate (Pounds per Acre) | Percent Defoliation |
|---|---|---|
| Control | — | 0 |
| Ethephon | 0.5 | 0 |
| Compound 96 | 0.5 | 0 |
| *Ethephon + Compound 96 | 0.5 + 0.5 | 87 |
| **Ethephon + Compound 96 | 0.5 + 0.5 | 10 |
| **Compound 96 + Ethephon | 0.5 + 0.5 | 86 |

Combination application method (tank mix).
**Sequential application method.

The results in Table W demonstrate a synergistic defoliation effect for the combination application method (tank mix) of ethephon and a malonic acid derivative compound. In regard to the sequential application method, a synergistic defoliation effect is demonstrated by applying the malonic acid derivative compound prior to ethephon.

EXAMPLE CIX

Effect of Representative Synergistic Compositions on Defoliation and Boll Opening of Cotton Solutions of the test compounds and compositions identified in Table X were prepared by dissolving the compounds in acetone/water (50:50 volume/volume) containing 0.1 percent volume/volume of Surfel® spray adjuvant commercially available from Union Carbide Corporation, Danbury, Conn. As detailed below, these solutions of test compounds and compositions were applied to cotton plants at a concentration of 0.5 pounds of each active ingredient per acre or 2.0 pounds of active ingredient per acre. The compositions were applied to cotton as mixtures.

The above solutions were applied to cotton plants growing under field conditions at a spray volume equivalent to 100 gallons per acre by use of a carbon dioxide backpack sprayer set at about 30 psig air pressure. The application timing coincided with a cotton maturity phase equivalent to about 40 percent open bolls. As a control, a water-acetone solution containing no test compound or composition was also sprayed on the cotton plants. At four days after treatment, percent defoliation of the cotton plants was determined by visual observation. At 14 days after treatment, percent boll opening was determined by visual observation of the number of open bolls/total number of bolls. The percent defoliation and percent boll opening values obtained for the control and each of the test compounds and compositions are reported in Table L as the average of three replications.

TABLE X

Effect of Representative Synergistic Compostions on Defoliation and Boll Opening of Cotton

| Compound/ Composition Identification | Rate (Pounds per Acre) | Percent Defoliation | Percent Boll Opening |
|---|---|---|---|
| Control | — | 0 | 41 |
| Ethephon | 2.0 | 5 | 64 |
| Compound 96 | 2.0 | 0 | * |
| Ethephon + Compound 96 | 0.5 + 0.5 | 91 | 70 |
| Compound 111 | 2.0 | 0 | * |
| Ethephon + Compound 111 | 0.5 + 0.5 | 96 | 95 |
| Compound 75 | 2.0 | 0 | * |
| Ethephon + Compound | 0.5 + 0.5 | 95 | 60 |

TABLE X-continued
Effect of Representative Synergistic Compostions on Defoliation and Boll Opening of Cotton

| Compound/ Composition Identification | Rate (Pounds per Acre) | Percent Defoliation | Percent Boll Opening |
|---|---|---|---|
| 75 | | | |

*Percent boll opening essentially the same as the control as determined by visual observation.

The results in Table X demonstrate that compositions containing ethephon and a malonic acid derivative compound provide a synergistic effect on defoliation and boll opening of cotton.

EXAMPLE CX
Effect of Representative Synergistic Compositions on Defoliation of Cotton (Rank Growth)

In a manner similar to the procedure described in Example XXXI, the defoliation effect on rank growth cotton was determined for representative synergistic compositions at various rates of application. The results of these tests are set forth in Table Y below. Rank growth cotton refers to cotton which exhibits excessive vegetative growth.

TABLE Y
Effect of Representative Synergistic Compositions on Defoliation of Cotton (Rank Growth)

| Compound/ Composition Identification | Rate (Pounds per Acre) | Percent Defoliation |
|---|---|---|
| Control | — | 0 |
| Ethephon | 2.0 | 12 |
| Compound 96 | 2.0 | 0 |
| Ethephon + Compound 96 | 1.0 + 0.25 | 85 |
| Compound 96 | 2.0 | 0 |
| Ethephon + Compound 96 | 1.0 + 0.50 | 96 |
| Compound 111 | 2.0 | 0 |
| Ethephon + Compound 111 | 1.0 + 0.25 | 97 |
| Compound 111 | 2.0 | 0 |
| Ethephon + Compound 111 | 1.0 + 0.50 | 99 |
| Compound 75 | 2.0 | 0 |
| Ethephon + Compound 75 | 1.0 + 0.25 | 40 |
| Compound 75 | 2.0 | 0 |
| Ethephon + Compound 75 | 1.0 + 0.50 | 70 |
| Compound 75 | 2.0 | 0 |
| Ethephon + Compound 75 | 1.0 + 1.0 | 82 |

The results in Table M demonstrate that compositions containing ethephon and a malonic acid derivative compound provide a synergistic effect on defoliation of rank growth cotton.

EXAMPLE CXI
Effect of Sequential Applications of Representative Synergistic Compositions on Defoliation of Cotton In a manner similar to the procedure described in Example XXXI, the defoliation effect on cotton was determined for representative synergistic compositions using sequential application. Ethephon applications were made 7 days after application of the particular malonic acid derivative compound. The results of these tests are set forth in Table Z below.

TABLE Z
Effect of Sequential Applications of Representative Synergistic Compositions on Defoliation of Cotton

| Compound/ Composition Identification | Rate (Pounds per Acre) | Percent Defoliation |
|---|---|---|
| Control | — | 0 |
| Ethephon | 0.25 | 3 |
| Compound 96 | 0.5 | 0 |
| | 1.0 | 0 |
| Compound 111 | 0.5 | 0 |
| | 1.0 | 0 |
| Compound 75 | 1.0 | 0 |
| Compound 96 + Ethephon | 0.5 + 0.25 | 93 |
| Compound 96 + Ethephon | 1.0 + 0.25 | 90 |
| Compound 111 + Ethephon | 0.5 + 0.25 | 87 |
| Compound 111 + Ethephon | 1.0 + 0.25 | 93 |
| Compound 75 + Ethephon | 1.0 + 0.25 | 79 |

The results in Table Z demonstrate that compositions containing ethephon and a malonic acid derivative compound provide a synergistic effect on defoliation of cotton by sequential application.

EXAMPLE CXII
cl Effect of Representative Synergistic Compositions on Defoliation of Cotton In a manner similar to the procedure described in Example XXXI. The defoliation effect on cotton was determined for representative synergistic compositions at various rates of application. The results of these tests are set forth in Table AA below.

TABLE AA
Effect of Representative Synergistic Compositions on Defoliation of Cotton

| Compound/ Composition Identification | Rate (Pounds per Acre) | Percent Defoliation |
|---|---|---|
| Control | — | 0 |
| Ethephon | 0.5 | 13 |
| Compound 96 | 0.5 | 0 |
| Compound 96 + Ethephon | 0.5 + 0.5 | 99 |
| Compound 96 | 0.5 | 0 |
| Compound 96 + Ethephon | 0.5 + 0.25 | 99 |
| Compound 97 | 0.5 | 0 |
| Compound 97 + Ethephon | 0.5 + 0.5 | 75 |
| Compound 65 | 0.5 | 0 |
| Compound 65 + Ethephon | 0.5 + 0.5 | 90 |
| Compound 66 | 0.5 | 0 |
| Compound 66 + Ethephon | 0.5 + 0.5 | 60 |
| Compound 69 | 0.5 | 0 |
| Compound 69 + Ethephon | 0.5 + 0.5 | 73 |
| Compound 5 | 0.5 | 0 |
| Compound 5 + Ethephon | 0.5 + 0.5 | 78 |
| Compound 26 | 0.5 | 0 |
| Compound 26 + Ethephon | 0.5 + 0.5 | 97 |
| Compound 35 | 0.5 | 0 |
| Compound 35 + Ethephon | 0.5 + 0.5 | 67 |
| Compound 102 | 0.5 | 0 |
| Compound 102 + Ethephon | 0.5 + 0.5 | 63 |
| Compound 77 | 0.5 | 0 |
| Compound 77 + | 0.5 + 0.5 | 97 |

TABLE AA-continued

Effect of Representative Synergistic Compositions on Defoliation of Cotton

| Compound/ Composition Identification | Rate (Pounds per Acre) | Percent Defoliation |
|---|---|---|
| Ethephon | | |
| Compound 110 | 0.5 | 0 |
| Compound 110 + Ethephon | 0.5 + 0.5 | 83 |

The results in Table AA demonstrate that compositions containing ethephon and a malonic acid derivative compound provide a synergistic effect on defoliation of cotton.

EXAMPLE CXIII

Effect of Representative Synergistic Compositions on Defoliation of Cotton

In a manner similar to the procedure described in Example XXXI, the defoliation effect on cotton was determined for representative synergistic compositions at various rates of application. The results of these tests are set forth in Table BB below.

TABLE BB

Effect of Representative Synergistic Compositions on Defoliation of Cotton

| Compound/ Composition Identification | Rate (Pounds per Acre) | Percent Defoliation |
|---|---|---|
| Control | — | 0 |
| Ethephon | 0.5 | 5 |
| Compound 111 | 0.5 | 0 |
| Compound 111 + Ethephon | 0.5 + 0.5 | 99 |
| Compound 111 | 0.5 | 0 |
| Compound 111 + Ethephon | 0.5 + 0.25 | 99 |
| Compound 111 | 0.25 | 0 |
| Compound 111 + Ethephon | 0.25 + 0.5 | 93 |
| Compound 111 | 0.25 | 0 |
| Compound 111 + Ethephon | 0.25 + 0.5 | 96 |

The results in Table BB demonstrate that compositions containing ethephon and a malonic acid derivative compound provide a synergistic effect on defoliation of cotton.

EXAMPLE CXIV

Effect of Representative Synergistic Compositions on Regrowth of Cotton following Defoliation In a manner similar to the procedure described in Example XXXI, the effect of cotton regrowth after defoliation was determined for representative synergistic compositions at various rats of application. The percent regrowth inhibition and stimulation in Table CC below were determined by visual observation based on the percent of a cotton plant having regrowth using a DEF treated cotton plant as the standard. DEF is commercially available from Mobay Chemical Corporation, Kansas City, Mo. The average regrowth of a cotton plant treated with DEF was 43 percent. As used in Table CC, percent regrowth inhibition resulted from a cotton plant having a regrowth percentage less than 43 percent (DEF standard), and percent regrowth stimulation resulted from a cotton plant having a regrowth percentage greater than 43 percent. The percent regrowth inhibition and stimulation were determined 30 days after treatment. The results of these tests are set forth in Table CC.

TABLE CC

Effect of Representative Synergistic Compositions on Regrowth of Cotton following Defoliation

| Compound/ Composition Identification | Rate (Pounds per Acre) | Percent Stimulation | Percent Inhibition |
|---|---|---|---|
| Control (DEF) | — | 0 | 0 |
| Ethephon | 0.5 | 16 | 0 |
| | 1.0 | 70 | 0 |
| | 2.0 | 62 | 0 |
| Compound 96 | 0.5 | 0 | 0 |
| Ethephon + Compound 96 | 0.5 + 0.5 | 0 | 53 |
| Compound 96 | 0.5 | 0 | 0 |
| Ethephon + Compound 96 | 0.5 + 1.0 | 0 | 63 |
| Compound 96 | 0.5 | 0 | 0 |
| Ethephon + Compound 96 | 1.0 + 0.5 | 0 | 46 |
| Compound 96 | 0.5 | 0 | 0 |
| Ethephon + Compound 96 | 1.0 + 1.0 | 0 | 72 |
| Compound 111 | 0.5 | 0 | 0 |
| Ethephon + Compound 111 | 0.5 + 0.5 | 0 | 65 |
| Compound 111 | 0.5 | 0 | 0 |
| Ethephon + Compound 111 | 0.5 + 1.0 | 0 | 53 |
| Compound 111 | 0.5 | 0 | 0 |
| Ethephon + Compound 111 | 1.0 + 0.5 | 0 | 44 |
| Compound 111 | 0.5 | 0 | 0 |
| Ethephon + Compound 111 | 1.0 + 1.0 | 0 | 51 |
| Compound 75 | 0.5 | 0 | 0 |
| Ethephon + Compound 75 | 0.5 + 0.5 | 0 | 53 |
| Compound 75 | 0.5 | 0 | 0 |
| Ethephon + Compound 75 | 1.0 + 1.0 | 0 | 16 |

The results in Table CC demonstrate that compositions containing ethephon and a malonic acid derivative compound provide a synergistic effect on regrowth inhibition of cotton following defoliation.

EXAMPLE CXV

Effect of Representative Synergistic Compositions on leaf Ripening of Tobacco

In a manner similar to the procedure described in Example XXVIII except that mature tobacco plants were used in place of snapbean plants, the leaf ripening effect of tobacco was determined for representative synergistic compositions at various rates of application. About 14 days prior to treatment, the mature tobacco plants were topped and treated with 4.0 pounds per acre of MH-30 to retard axially bud development. MH-30 is commercially available from Uniroyal Chemical Company, Bethany, Conn. Percent tobacco leaf ripening (chlorosis) was determined by visual observation of the upper three leaves of the tobacco plant at 7 days after treatment. The results of these tests are set forth in Table DD below.

TABLE DD

Effect of Reresentative Synergistic Compositions on Leaf Ripening of Tobacco

| Compound/ Composition Identification | Rate (Pounds per Acre) | Percent Ripening (Chlorosis) |
|---|---|---|
| Control | — | 10 |

TABLE DD-continued

Effect of Reresentative Synergistic Compositions on Leaf Ripening of Tobacco

| Compound/ Composition Identification | Rate (Pounds per Acre) | Percent Ripening (Chlorosis) |
|---|---|---|
| Ethephon | 1.0 | 10 |
| Compound 96 | 1.0 | 10 |
| Compound 96 + Ethephon | 1.0 + .25 | 25 |
| Compound 96 | 1.0 | 10 |
| Compound 96 + Ethephon | 1.0 + 0.5 | 30 |
| Compound 96 | 1.0 | 10 |
| Compound 96 + Ethephon | 1.0 + 1.0 | 60 |

The results in Table DD demonstrate that compositions containing ethephon and a malonic acid derivative compound provide a synergistic effect on leaf ripening of tobacco.

EXAMPLE CXVI

Effect of Representative Synergistic Compositions On Leaf Ripening of Tobacco

In a manner similar to the preceding Example, mature tobacco plants were treated with representative synergistic compositions of this invention and effect on tobacco leaf ripening noted. The results are set forth in table EE below.

TABLE EE

EFFECT OF SYNERGISTIC COMPOSITIONS ON TOBACCO LEAF RIPENING

| TREATMENT | RATE (LB AI/A) | LEAF MATURITY DAYS AFTER TREATMENT | | | | |
|---|---|---|---|---|---|---|
| | | 1 | 2 | 3 | 4 | 5 |
| ETHEPHON | 0.25 | 2.0 | 2.0 | 2.0 | 3.0* | 3.3 |
| | 0.50 | 1.7 | 2.0 | 2.0 | 3.3* | 3.8 |
| ETHEPHON + POTASSIUM SALT OF COMPOUND 75 | 0.25 + 0.50 | 2.0 | 2.0 | 3.0* | 3.7 | 4.2 |
| | 0.25 + 1.00 | 1.7 | 1.7 | 2.3 | 3.3* | 3.8 |
| | 0.50 + 0.50 | 2.0 | 2.0 | 2.7* | 3.7 | 4.0 |
| | 0.50 + 0.50 | 2.0 | 2.0 | 3.0* | 3.3 | 4.0 |
| ETHEPHON + POTASSIUM SALT OF COMPOUND 111 | 0.25 + 0.25 | 2.0 | 2.0 | 2.0 | 3.3* | 4.0 |
| | 0.25 + 0.50 | 2.0 | 2.0 | 3.0* | 3.3 | 4.0 |
| | 0.50 + 0.25 | 2.0 | 2.0 | 2.7* | 4.0 | 4.3 |
| | 0.50 + 0.50 | 2.0 | 2.0 | 2.7* | 3.7 | 4.5 |
| CONTROL | — | 1.7 | 2.0 | 2.0 | 2.0 | 2.0 |

*READY FOR HARVEST
LEAF MATURITY INDEX 1-4
1 = GREEN MATURE, SOME MOTTLING
2 = CHANGE TO LIGHT YELLOW-GREEN, NO MOTTLING AT THE BUTTS
3 = LEAVES PALE YELLOW, READY FOR HARVEST
4 = LEAVES PALE YELLOW WITH BRIGHT YELLOW TIPS
5 = LEAVES OVER MATURE

EXAMPLE CXVII

Effect of Synergistic Compositions On Vine Senescence in Tomatoes

The vine senescence in tomatoes was determined by applying representative synergistic compositions of the inventions to tomato plants and the percent defoliation noted after 8 and 13 days. The results are set forth in Table FF below.

TABLE FF

Effect of Synergistic Composition on Vine Senescence in Tomatoes

| TREATMENT | RATE (LB AI/A) | % DEFOLIATION | |
|---|---|---|---|
| | | 8 DAYS | 13 DAYS |
| ETHEPHON | 0.125 | 3 | 7 |
| | 0.25 | 6 | 11 |
| | 0.50 | 36 | 44 |
| | 0.75 | 63 | 64 |
| ETHEPHON + POTASSIUM SALT OF COMPOUND 75 | 0.125 + 0.25 | 12 | 17 |
| | 0.125 + 0.50 | 15 | 24 |
| | 0.25 + 0.25 | 19 | 26 |
| | 0.25 + 0.50 | 25 | 37 |
| ETHEPHON + POTASSIUM SALT OF COMPOUND 111 | 0.125 + 0.25 | 55 | 60 |
| | 0.125 + 0.50 | 62 | 76 |
| | 0.25 + 0.25 | 81 | 87 |
| | 0.25 + 0.50 | 84 | 87 |
| CONTROL | — | 1 | 5 |

EXAMPLE CXVIII

Effect of Representative Synergistic Compositions on Defoliation of Snapbean Plants In the manner similar to the procedure described in Example XXVIII, the defoliation effect on snapbean plants was determined for representative synergistic compositions at various rates of application using various ethylene releasing agents identified in Table GG below. The ethylene releasing agents used in Table GG are known materials which can be prepared by conventional methods. The results of these tests are set forth in Table GG.

TABLE GG

Effect of Representative Synergistic Compositions on Defoliation of Snapbean Plants

| Compound/ Composition Identification | Rate (Pounds per Acre) | Percent Defoliation |
|---|---|---|
| Control | — | 0 |
| Compound 111 | 0.125 | 0 |
| | 0.25 | 0 |
| | 0.50 | 0 |
| 2-chloroethanesulfinic acid | 0.125 | 0 |
| | 0.25 | 0 |
| | 0.50 | 0 |
| Compound 111 + 2-chloroethanesulfinic acid | 0.125 + 0.125 | 30 |
| | 0.125 + .25 | 20 |
| | 0.50 + 0.50 | 50 |
| 2-Chloroethylthiono-phosphonic acid | 0.125 | 0 |
| | 0.25 | 0 |
| | 0.50 | 0 |
| Compound 111 + 2-Chloroethylthiono-phosphonic acid | 0.125 + 0.125 | 60 |
| | 0.125 + 0.25 | 50 |
| | 0.50 + 0.50 | 100 |
| Ethephon | 0.125 | 0 |
| | 0.25 | 0 |
| | 0.50 | 0 |
| Compound 111 + Ethephon | 0.125 + 0.125 | 53 |
| | 0.125 + 0.25 | 67 |
| | 0.50 + 0.50 | 89 |
| 2-Chloroethyl ester of 2-chloroethylphosphonic acid | 0.125 | 0 |
| | 0.25 | 0 |
| | 0.50 | 0 |
| Compound 111 + 2-Chloroethyl ester of 2-chloroethylphosphonic acid | 0.125 | 40 |
| | 0.125 + 0.25 | 40 |
| | 0.50 + 0.50 | 87 |
| 2-Bromoethylphosphonic acid | 0.125 | 0 |
| | 0.25 | 0 |
| | 0.50 | 0 |
| Compound 111 + 2-Bromoethylphosphonic acid | 0.125 + 0.125 | 33 |
| | 0.125 + 0.25 | 30 |
| | 0.50 + 0.50 | 73 |
| 2-Chloroethylphosphonic diamide | 0.125 | 0 |
| | 0.25 | 0 |
| | 0.50 | 0 |
| Compound 111 + | 0.125 + 0.125 | 33 |

TABLE GG-continued

Effect of Representative Synergistic
Compositions on Defoliation of Snapbean Plants

| Compound/<br>Composition<br>Identification | Rate<br>(Pounds<br>per Acre) | Percent<br>Defoliation |
| --- | --- | --- |
| 2-Chloroethylphosphonic | 0.125 + 0.25 | 27 |
| diamide | 0.50 + 0.50 | 100 |
| Tris-(2-methoxyethoxy)-2- | 0.125 | 0 |
| chloroethylsilane | 0.25 | 0 |
|  | 0.50 | 0 |
| Compound 111 + | 0.125 + 0.125 | 37 |
| Tris-(2-methoxyethoxy)-2- | 0.125 + 0.25 | 17 |
| chloroethylsilane | 0.50 + 0.50 | 43 |
| 1-Amino-1-cyclopropane- | 0.125 | 0 |
| carboxylic acid (ACC) | 0.25 | 0 |
|  | 0.50 | 0 |
| Compound 111 + | 0.125 + 0.125 | 33 |
| 1-Amino-1-cyclopropane- | 0.125 + 0.25 | 73 |
| carboxylic acid (ACC) | 0.50 + 0.50 | 83 |

The results in Table GG demonstrate that compositions containing an ethylene releasing agent and a malonic acid derivative compound provide a synergistic effect on defoliation of snapbean plants.

EXAMPLE CXIX

Effect of Ethylene Gas and a Malonic Acid Derivative Compound on Abscission of Snapbean Plant Leaves Solutions of test compounds identified in Table T below were prepared by dissolving the compounds in acetone/water (60:40 volume/volume) containing 0.1 percent volume/volume of Triton X-100 surfactant commercially available from Rohm and Haas Company, Philadelphia, Pa.

In a manner similar to the procedure described in Example XXVIII, the solutions of test compounds were applied as a foliar spray to snapbean plants at a concentration of 125 parts per million of active ingredient or 250 parts per million of active ingredient. Prior to treatment, the snapbean plants with an expanded trifoliolate leaf were topped leaving two fully expanded primary leaves. After a period of 24 hours following treatment, the snapbean plants were placed in 10.3 liter desiccators and exposed to ethylene gas at a concentration of 0.1 part per million (ppm). A carbon dioxide trap (2 milliliters of 40 percent potassium hydroxide) was included in each desiccator. The sealed desiccators were then placed in a dark environment. After a period of 48 hours and 96 hours in which the treated snapbean plants were exposed to ethylene gas, percent abscission was determined by visual observation of abscised leaves. The plants were also rated at 96 hours (48 hours after termination of ethylene gas exposure). The percent abscission values are reported in Table FF as the average of three replications.

TABLE HH

Effect of Ethylene Gas and a Malonic Acid
Derivative Compound on Abscission of
Snapbean Plant Leaves

| Compound/<br>Composition<br>Identification | Concentration<br>(ppm) | Percent Abscission | |
| --- | --- | --- | --- |
|  |  | 48<br>Hours | 96<br>Hours |
| Control | — | 0 | 0 |
| Ethylene Gas | 0.1 | 0 | 0 |
| Compound 111 | 125 | 0 | 17 |
| Compound 111 + Ethylene Gas | 125 + 0.1 | 33 | 100 |
| Compound 111 | 250 | 33 | 50 |

TABLE HH-continued

Effect of Ethylene Gas and a Malonic Acid
Derivative Compound on Abscission of
Snapbean Plant Leaves

| Compound/<br>Composition<br>Identification | Concentration<br>(ppm) | Percent Abscission | |
| --- | --- | --- | --- |
|  |  | 48<br>Hours | 96<br>Hours |
| Compound 111 + Ethylene Gas | 250 + 0.1 | 83 | 100 |

The results in Table HH demonstrate that a combination of ethylene gas and a malonic acid derivative compound provide a synergistic effect on abscission of snapbean plant leaves.

EXAMPLE CXX

Effect of Representative Synergistic Compositions on Leaf Ripening of Snapbeans

Stock solutions containing 2 milligrams/milliliter of the test compounds identified in Table U below were prepared by dissolving appropriate amounts of ethephon in water and appropriate amounts of Compound 75 in acetone/water (50:50 volume/volume). The test solutions identified in Table U were made by dilution with water.

Into 7.6 centimeter diameter paper pots containing a potting soil (one-third perlite, one-third peat-lite and one-third sandy loan farm soil (volume:volume:volume)) were sown three snapbean seeds (*Phaseolus vulgaris* var. Cranberry). Five to seven days after planting, the plants were thinned to one plant per pot. Twelve days following treatment, 10 disks (9 millimeter diameter) were punched from the primary leaves of each bean plant. Each set of 10 disks was placed in a petri dish containing 20 milliliters of the appropriate test solutions prepared above. As a control, a water-acetone solution containing no test compound was also used. Each petri dish was then placed in a dark environment for a period of 48 hours at a temperature of 28° C. Upon removal from the dark environment, each set of disks was visually rated for ripening activity. Visual indications of leaf ripening were observed and recorded employing a system of numerical ratings.

Numerical ratings from "0" to "10" were used to designate the degree of leaf ripening observed in comparison with the untreated control. A "0" rating indicates no visible response and a "10" rating indicates a maximum response, i.e., bright yellow. The results are reported in Table II and are the average of 3 repetitions.

TABLE II

Effect of Representative Synergistic
Compositions on Leaf Ripening of Snapbeans

| Compound<br>No. | Concentration<br>(ppm) | Leaf<br>Ripening<br>Rating |
| --- | --- | --- |
| Control | 0 | 0 |
| Ethephon | 50 | 1 |
|  | 100 | 4.7 |
| Compound 75 | 100 | 0 |
|  | 200 | 0 |
|  | 500 | 1 |
| Ethephon + Compound 75 | 50 + 100 | 2.3 |
|  | 50 + 200 | 3 |
|  | 50 + 500 | 5 |
|  | 100 + 100 | 7 |
|  | 100 + 200 | 9 |

TABLE II-continued
Effect of Representative Synergistic Compositions on Leaf Ripening of Snapbeans

| Compound No. | Concentration (ppm) | Leaf Ripening Rating |
|---|---|---|
| | 100 + 500 | 10 |

The results in Table II demonstrate that compositions containing an ethylene releasing agent and a malonic acid derivative compound provide a synergistic effect on ripening of snapbeans.

EXAMPLE CXXI

Effect of Representative Synergistic Compositions on Plant Chlorophyll Content-Ripening A stock solution of ethephon containing 2 milligrams/milliliter was prepared by dissolving an appropriate amount in water. A stock solution of Compound 75 was prepared by mixing 150 milligrams of Compound 75 with 0.5 milliliters of Triton X-100 surfactant, 1 milliliter of gamma-butyrolactone and 500 milliliters of water. The test solutions identified in Table V below were made by dilution with water. Triton X-100 surfactant is commercially available from Rohm and Haas Company, Philadelphia, Pa.

Into 7.6 centimeter diameter paper pots containing a potting soil (one-third perlite, one-third peat-lite and one-third sandy loam farm soil (volume:volume:volume)) were sown three snapbean seeds (*Phaseolus vulgaris* var. Cranberry). Five to seven days after planting, the plants were thinned to one plant per pot. Twelve days following treatment, 10 disks (12 millimeter diameter) were punched from the primary leaves of each bean plant. Each set of 10 disks was placed in a petri dish containing 20 milliliters of the appropriate test solutions prepared above. As a control, a water-acetone solution containing no test compound was also used. Each petri dish was then placed in a dark environment for a period of 48 hours at a temperature of 28° C. Upon removal from the dark environment, each set of disks was blotted fry and placed in a test tube on ice.

Each set of disks were then homogenized in a Waring blender with 20 milliliters of a solution containing 80 percent acetone/20 percent water (volume/volume). The resulting suspensions were centrifuged at a temperature of 0° C.-2° C. at 12,000×g (g=980 cm sec$^{-2}$) for a period of 5 minutes. The supernatant containing the chlorophyll was saved and the absorbance of light of the solutions at 645 nanometers (nm) and 663 nanometers (nm) was determined by spectrophotometric analysis. Total chlorophyll (milligrams chlorophyll/grams leaf tissue) was calculated according to the following equation:

$$\frac{\text{milligrams of chlorophyll}}{\text{grams of leaf tissue}} = \frac{(20.2)(\text{absorbance at 645 nm}) + (8.02)(\text{absorbance at 663 nm})}{\text{weight of leaf disks (grams)}}$$

Each value for the control and test solutions identified in Table JJ is the average of two repetitions.

TABLE JJ
Effect of Representative Synergistic Compositions on Plant Chlorophyll Content - Ripening

| Compound No. | Concentration (ppm) | Chlorophyll Content (milligrams chlorophyll/ grams leaf tissue) | Chlorophyll (% of Control) |
|---|---|---|---|
| Control | — | 41.40 | 100 |
| Ethephon | 75 | 33.54 | 81.0 |
| Compound 75 | 150 | 36.90 | 89.1 |
| Ethephon + Compound 75 | 75 + 150 | 26.77 | 64.7 |

The results in Table JJ demonstrate that compositions containing an ethylene releasing agent and a malonic acid derivative compound provide a synergistic effect on ripening of snapbeans.

We claim:

1. A plant growth regulator composition comprising an effective amount of (i) an ethylene response or ethylene-type response inducing agent consisting of 2-chloroethylphosphonic acid and (ii) a malonic acid derivative compound having a formula:

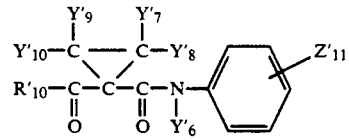

wherein:

Z'$_{11}$ is the same or different and is one or more hydrogen, halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy, alkenyl or —CH=CHCH=CH—; and in which the alkyl, alkoxy, acyl or alkenyl moiety is lower alkyl, lower alkoxy, lower acyl or lower alkenyl and the aryl or aroyl moiety is hydrocarbyl aryl or hydrocarbyl aroyl;

Y'$_6$ is hydrogen or lower alkyl;

Y'$_7$, R'$_8$, Y'$_9$ and Y'$_{10}$ are each independently hydrogen, halogen or lower alkyl; and R'$_{10}$ is R''$_{10}$Y'$_{41}$ in which R''$_{10}$ is hydrogen, a derivative salt or an unsubstituted or substituted lower alkyl and Y'$_{41}$ is O, S, NH or N (lower alkyl);

and in which the amount of compound (ii) used with agent 2-chloroethylphosphonic acid (i) results in a mixture having a greater plant growth regulating effect than the sum total plant growth regulating effect of agent 2-chloroethylphosphonic acid (i) and compound (ii) each used alone.

2. The plant growth regulator composition of claim 1 having the malonic acid derivative compound in which R''$_{10}$ is hydrogen or a derivative salt.

3. The plant growth regulator composition of claim 2 in which the derivative salt is an alkali metal, an alkaline earth metal, ammonium, alkylammonium, polyalkylammonium, hydroxyalkylammonium, or poly(hydroxyalkyl)ammonium or mixtures thereof; and in which the alkyl moiety is lower alkyl.

4. A method for regulating plant growth which comprises applying to the plant an effective amount of a synergistic plant growth regulator composition comprising (i) an ethylene response or ethylene-type response inducing agent consisting of 2-chloroethylphosphonic acid (ethephon) and (ii) a malonic acid derivative compound having a formula

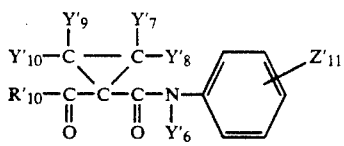

wherein:

$Z'_{11}$ is the same or different and is one or more hydrogen, halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy, alkenyl or CH=CHCH=CH—; and in which the alkyl, alkoxy, acyl or alkenyl moiety is lower alkyl, lower alkoxy, lower acyl or lower alkenyl and the aryl or aroyl moiety is hydrocarbyl aryl or hydrocarbyl aroyl;

$Y'_6$ is hydrogen or lower alkyl;

$Y'_7$, $Y'_8$, $Y'_9$ and $Y'_{10}$ are each independently hydrogen, halogen or lower alkyl; and $R'_{10}$ is $R''_{10}Y'_{41}$ in which $R''_{10}$ is hydrogen, a derivative salt or an unsubstituted or substituted lower alkyl and $Y'_{41}$ is O, S, NJ or N (lower alkyl).

5. The method for regulating plant growth of claim 4 which involved an ethylene response or ethylene-type response.

6. The method for regulating plant growth of claim 4 which involves increasing yields.

7. The method for regulating plant growth of claim 4 which involves the enhancement of auxin activity.

8. The method for regulating plant growth of claim 4 which involves inhibition of terminal growth.

9. The method for regulating plant growth of claim 4 which involves control of apical dominance.

10. The method for regulating plant growth of claim 4 which involves an increase in branching.

11. The method for regulating plant growth of claim 4 which involves an increase in tillering.

12. The method for regulating plant growth of claim 4 which involves changing the biochemical composition of the plant.

13. The method for regulating plant growth of claim 4 which involves abscission of foliage, flowers and fruit or stimulation of separation of an abscission zone.

14. The method for regulating plant growth of claim 4 which involves hastening ripening and color promotion in fruit.

15. The method for regulating plant growth of claim 4 which involves an increase in flowering and fruiting and causing flower induction.

16. The method for regulating plant growth of claim 4 which involves abortion or inhibition of flowering and seed development.

17. The method for regulating plant growth of claim 4 which involves prevention of lodging.

18. The method for regulating plant growth of claim 4 which involves stimulation of seed germination and breaking of dormancy.

19. The method for regulating plant growth of claim 4 which involves promotion of resistance to freeze injury.

20. The method for regulating plant growth of claim 4 which involves inducing of hormone or epinasty effects.

21. The method for regulating plant growth of claim 4 which involves defoliation and regrowth inhibition.

22. The plant growth regulator composition of claim 1 in which the effective amount is a weight proportion of the 2-chloroethylphosphonic acid ethylene response or ethylene-type response inducing agent to the malonic acid derivative compound from about 0.1:1000 to about 1000:0.1.

23. The plant growth regulator composition of claim 22 in which the weight proportion of the 2-chloroethylphosphonic acid ethylene response or ethylene-type response inducing agent to the malonic acid derivative compound is from about 1:500 to about 500:1.

24. The method for regulating plant growth of claim 4 in which the effective amount is a weight proportion of the 2-chloroethylphosphonic acid ethylene response or ethylene-type response inducing agent to the malonic acid derivative compound from about 0.1:1000 to about 1000:0.1.

25. The method for regulating plant growth of claim 24 in which the weight proportion of the 2-chloroethylphosphonic acid ethylene response or ethylene-type response inducing agent to the malonic acid derivative compound is from about 1:500 to about 500:1.

26. The method for regulating plant growth of claim 4 in which the synergistic plant growth regulator composition is applied to the plant at a rate of from 0.001 pounds per acre to 100 pounds per acre.

27. The method for regulating plant growth of claim 26 in which the synergistic plant growth regulator composition is applied to the plant at a rate of from 0.01 pounds per acre to 15 pounds per acre.

28. The method for regulating plant growth of claim 27 in which the synergistic plant growth regulator composition is applied to the plant at a rate of from 0.1 pounds per acre to 5 pounds per acre.

29. The method for regulating plant growth of claim 4 having the malonic acid derivative compound in which $R''_{10}$ is hydrogen or a derivative salt and $Y'_{41}$ is 0.

30. The method for regulating plant growth of claim 29 in which the derivative salt is an alkali metal, an alkaline earth metal, ammonium, alkylammonium, polyalkylammonium, hydroxyalkylammonium, or poly(hydroxyalkyl)ammonium or mixtures thereof; and in which the alkyl moiety is lower alkyl.

31. The method for regulating plant growth of claim 4 which comprises a combination composition of the 2-chloroethylphosphonic acid ethylene response or ethylene-type response inducing agent and the malonic acid derivative compound.

32. The method for regulating plant growth of claim 4 which comprises a sequential application of the 2-chloroethylphosphonic acid ethylene response or ethylene-type response inducing agent and the malonic acid derivative compound.

33. The method for regulating plant growth of claim 32 wherein the malonic acid derivative compound is applied to the plant prior to the 2-chloroethylphosphonic acid ethylene response or ethylene-type response inducing agent.

34. The plant growth regulator composition of claim 1, wherein:

R″$_{10}$ is hydrogen, ammonium, alkylammonium, polyalkylammonium, hydroxyalkylammonium, poly(hydroxyalkyl)ammonium, an alkali metal or alkaline earth metal, alkyl, hydroxyalkyl, alkoxyalkyl, alkoxycarbonylalkyl, alkylaminoalkyl, dialkylaminoalkyl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonyloxyalkyl, alkoxycarbonylthioalkyl, aminosulfonylalkyl, alkylaminosulfonylalkyl or dialkylaminosulfonylalkyl; and in which the alkyl, alkoxy, acyl or alkenyl moiety is lower alkyl, lower alkoxy, lower acyl or lower alkenyl and the aryl or aroyl moiety is hydrocarbyl aryl or hydrocarbyl aroyl.

35. The plant growth regulator composition of claim 34 wherein:

R″$_{10}$ is hydrogen, ammonium, alkylammonium, polyalkylammonium, hydroxyalkylammonium, poly(hydroxyalkly)-ammonium, an alkali metal or alkaline earth metal, alkyl, hydroxyalkyl, alkoxyalkyl, alkoxycarbonylalkyl, alkylamino-alkyl, dialkylaminoalkyl, alkylsulfonylalkyl, acylalkyl, hydroxyalkylsulfonylalkyl, poly(oxyalkylene)alkyl, cyanoalkyl or carbamoylalkyl.

36. The plant growth regulator composition of claim 35 wherein:

Y″$_6$ is hydrogen;

Y′$_7$, Y′$_8$, Y′$_9$ and Y′$_{10}$ are each independently hydrogen; and

Y′$_{41}$ is 0.

37. The plant growth regulator composition of claim 1, wherein:

Z′$_{11}$ is the same or different and is one or more hydrogen, halogen, haloalkyl, polyhaloalkyl, polyhaloalkoxy, alkyl, alkoxy or cyano.

38. The plant growth regulator composition of claim 37, wherein:

R″$_{10}$ is hydrogen, ammonium, alkylammonium, polyalkylammonium, hydroxyalkylammonium, poly(hydroxyalkyl)-ammonium, an alkali metal or alkaline earth metal, alkyl, hydroxyalkyl, alkoxyalkyl, alkoxycarbonylalkyl, alkylaminoalkyl, dialkylaminoalkyl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, alkoxycarbonlyoxyalkyl, alkoxycarbonylthioalkyl, aminosulfonylalkyl, alkylaminosulfonylalkyl or dialkylaminosulfonylalkyl; and in which the alkyl, alkoxy, acyl or alkenyl moiety is lower alkyl, lower alkoxy, lower acyl or lower alkenyl and the aryl or aroyl moiety is hydrocarbyl aryl or hydrocarbyl aroyl.

39. The plant growth regulator composition of claim 34 wherein:

R″$_{10}$ is hydrogen, ammonium, alkylammonium, polyalkylammonium, hydroxyalkylammonium, poly(hydroxyalkyl)-ammonium, an alkali metal or alkaline earth metal, alkyl, hydroxyalkyl, alkoxyalkyl, alkoxycarbonylalkyl, alkylamino-alkyl, dialkylaminoalkyl, alkylsulfonylalkyl, acylalkyl, hydroxyalkylsulfonylalkyl, poly(oxyalkylene)alkyl, cyanoalkyl or carbamoylalkyl.

40. The plant growth regulator composition of claim 39, wherein:

Y′$_6$ is hydrogen;

Y′$_7$, Y′$_8$, Y′$_9$ and Y′$_{10}$ are each independently hydrogen; and

Y′$_{41}$ is 0.

41. The plant growth regulator composition of claim 1, wherein:

Y′$_6$ is hydrogen;

Y′$_7$, Y′$_8$, Y′$_9$ and Y′$_{10}$ are each independently hydrogen; and

Y′$_{41}$ is 0.

42. The plant growth regulator composition of claim 41, wherein:

Z′$_{11}$ is the same or different and is one or more hydrogen, halogen, haloalkyl, polyhaloalkyl, polyhaloalkoxy, alkyl, alkoxy or cyano.

43. The plant growth regulator composition of claim 1 wherein:

R′$_{10}$ is R″$_{10}$Y′$_{41}$ in which R″$_{10}$ is hydrogen, a derivative salt or unsubstituted lower alkyl and Y′$_{41}$ ia oxygen;

Y′$_6$ is hydrogen;

Y′$_7$, Y′$_8$, Y′$_9$, and Y′$_{10}$ are each hydrogen; and

Z′$_{11}$ is 2-CH$_3$-4-CL-5-CL, 2-CH$_3$-4-Br, 2-Cl-4-Cl, 2-F-4-Cl, 4-Cl, 4-Br, 2-Br-4-Br, 2-Cl-4-Br, 2-Br-4-Cl, 2-F-4-Cl, 4-CF$_3$, 4-OCF$_3$ or 2-Cl-4-OCF$_3$.

44. The plant growth regulator composition of claim 43, wherein for the malonic acid derivative compound Z′$_{11}$ is 2-CH$_3$-4-Cl-5-Cl.

45. The plant growth regulator composition of claim 43, wherein for the malonic acid derivative compound Z′$_{11}$ is 2-CH$_3$-4-Br.

46. The plant growth regulator composition of claim 43, wherein for the malonic acid derivative compound Z′$_{11}$ is 2-Cl-4-Cl.

47. The plant growth regulator composition of claim 43, wherein for the malonic acid derivative compound Z′$_{11}$ is 2-F4-Cl.

48. The plant growth regulator composition of claim 43, wherein for the malonic acid derivative compound Z′$_{11}$ is 4-Cl.

49. The plant growth regulator composition of claim 43, wherein for the malonic acid derivative compound Z′$_{11}$ is 4-Br.

50. The plant growth regulator composition of claim 43, wherein for the malonic acid derivative compound Z′$_{11}$ is 2-Br-4-Br.

51. The plant growth regulator composition of claim 43, wherein for the malonic acid derivative compound Z′$_{11}$ is 2-Cl-4-Br.

52. The plant growth regulator composition of claim 43, wherein for the malonic acid derivative compound Z′$_{11}$ is 2-Br-4-Cl.

53. The plant growth regulator composition of claim 43, wherein for the malonic acid derivative compound $Z'_{11}$ is 2-F4-Br.

54. The plant growth regulator composition of claim 43, wherein for the malonic acid derivative compound $Z'_{11}$ is 4-CF$_3$.

55. The plant growth regulator composition of claim 43, wherein for the malonic acid derivative compound $Z'_{11}$ is 4-OCF$_3$.

56. The plant growth regulator composition of claim 43, wherein for the malonic acid derivative compound $Z'_{11}$ is 2-Cl-4-OCF$_3$.

57. The plant growth regulator composition of claim 23, in which the weight proportion of 2-chloroethylphosphonic acid to the malonic acid derivative compound is from about 1:4 to about 4:1.

58. The method for regulating plant growth of claim 4 wherein:
   $R'_{10}$ is $R''_{10}Y'_{41}$ in which $R''_{10}$ is hydrogen, a derivative salt or unsubstituted lower alkyl and $Y'_{41}$ is oxygen;
   $Y'_6$ is hydrogen;
   $Y'_7$, $Y'_8$, $Y'_9$, and $Y'_{10}$ are each hydrogen; and
   $Z'_{11}$ is 2-CH$_3$-4-Cl-5-Cl, 2-CH$_3$-4-Br, 2-Cl-4-Cl, 2-F-4-Cl, 4-Cl, 4-Br, 2-Br-4-Br, 2-Cl-4-Br, 2-Br-4-Cl, 2-F-4-Br, 4-CF$_3$, 4-OCF$_3$ or 2-Cl-4-OCF$_3$.

59. The method for regulating plant growth of claim 58, wherein for the malonic acid derivative compound $Z'_{11}$ is 2-CH$_3$-4-Cl-5-Cl.

60. The method for regulating plant growth of claim 58, wherein for the malonic acid derivative compound $Z'_{11}$ is 2-CH$_3$-4-Br.

61. The method for regulating plant growth of claim 58, wherein for the malonic acid derivative compound $Z'_{11}$ is 2-Cl-4-Cl.

62. The method for regulating plant growth of claim 58, wherein for the malonic acid derivative compound $Z'_{11}$ is 2-F-4-Cl.

63. The method for regulating plant growth of claim 58, wherein for the malonic acid derivative compound $Z'_{11}$ is 4-Cl.

64. The method for regulating plant growth of claim 58, wherein for the malonic acid derivative compound $Z'_{11}$ is 4-Br.

65. The method for regulating plant growth of claim 58, wherein for the malonic acid derivative compound $Z'_{11}$ is 2-Br-4-Br.

66. The method for regulating plant growth of claim 58, wherein for the malonic acid derivative compound $Z'_{11}$ is 2-Cl-4-Br.

67. The method for regulating plant growth of claim 58, wherein for the malonic acid derivative compound $Z'_{11}$ is 2-Br-4-Cl.

68. The method for regulating plant growth of claim 58, wherein for the malonic acid derivative compound $Z'_{11}$ is 2-F-4-Br.

69. The method for regulating plant growth of claim 58, wherein for the malonic acid derivative compound $Z'_{11}$ is 4-CF$_3$.

70. The method for regulating plant growth of claim 58, wherein for the malonic acid derivative compound $Z'_{11}$ is 4-OCF$_3$.

71. The method for regulating plant growth of claim 58, wherein for the malonic acid derivative compound $Z'_{11}$ is 2-Cl-4-OCF$_3$.

72. The method for regulating plant growth of claim 25, in which the weight proportion of 2-chloroethylphosphonic acid to the malonic acid derivative compound is from about 1:4 to about 4:1.

* * * * *